(12) United States Patent
Knaus et al.

(10) Patent No.: US 11,963,979 B2
(45) Date of Patent: Apr. 23, 2024

(54) PROCESS FOR T CELL EXPANSION

(71) Applicants: AlloVir, Inc., Waltham, MA (US); Baylor College of Medicine, Houston, TX (US); Wilson Wolf Manufacturing Corporation, New Brighton, MN (US)

(72) Inventors: Rainer Ludwig Knaus, London (GB); Katy Rebecca Newton, London (GB); Juan Vera, Houston, TX (US); Ann Leen, Houston, TX (US); Cliona Rooney, Bellaire, TX (US); John R. Wilson, New Brighton, MN (US)

(73) Assignees: AlloVir, Inc., Waltham, MA (US); Baylor College of Medicine, Houston, TX (US); Wilson Wolf Manufacturing Corporation, New Brighton, MN (US)

( * ) Notice: Subject to any disclaimer, the term of this patent is extended or adjusted under 35 U.S.C. 154(b) by 0 days.

(21) Appl. No.: 16/016,305

(22) Filed: Jun. 22, 2018

(65) Prior Publication Data
US 2019/0134092 A1   May 9, 2019

Related U.S. Application Data

(63) Continuation of application No. 14/364,621, filed as application No. PCT/GB2012/053113 on Dec. 12, 2012, now abandoned.

(30) Foreign Application Priority Data

Dec. 12, 2011  (GB) ..................... 1121308

(51) Int. Cl.
| | | |
|---|---|---|
| A61K 35/17 | (2015.01) | |
| A61K 39/12 | (2006.01) | |
| A61K 39/235 | (2006.01) | |
| A61K 39/245 | (2006.01) | |
| C12M 1/04 | (2006.01) | |
| C12N 5/0783 | (2010.01) | |
| C12N 7/00 | (2006.01) | |
| A61K 39/00 | (2006.01) | |

(52) U.S. Cl.
CPC ............ *A61K 35/17* (2013.01); *A61K 39/12* (2013.01); *A61K 39/235* (2013.01); *A61K 39/245* (2013.01); *C12M 23/24* (2013.01); *C12N 5/0636* (2013.01); *C12N 7/00* (2013.01); *A61K 2039/5158* (2013.01); *A61K 2039/55527* (2013.01); *C12N 2501/2304* (2013.01); *C12N 2501/2307* (2013.01); *C12N 2506/11* (2013.01); *C12N 2710/10034* (2013.01); *C12N 2710/16134* (2013.01); *C12N 2710/18034* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,641,628 A | 6/1997 | Bianchi | |
| 5,843,405 A | 12/1998 | Mideldorp | |
| 5,869,453 A | 2/1999 | Moss et al. | |
| 5,962,318 A | 10/1999 | Rooney et al. | |
| 6,040,177 A | 3/2000 | Riddell et al. | |
| 6,143,865 A | 11/2000 | Middeldorp | |
| 6,274,378 B1 | 8/2001 | Steinman et al. | |
| 6,451,305 B1 | 9/2002 | Boussiotis et al. | |
| 6,455,299 B1 | 9/2002 | Steinman et al. | |
| 6,528,307 B1 | 3/2003 | Herlyn | |
| 6,699,477 B2 | 3/2004 | Khanna et al. | |
| 6,713,053 B1 | 3/2004 | Bach et al. | |
| 6,723,695 B1 | 4/2004 | Burrows et al. | |
| 6,821,778 B1 | 11/2004 | Engelman et al. | |
| 6,828,147 B1 | 12/2004 | Santoli et al. | |
| 7,005,131 B1 | 2/2006 | Steinman et al. | |
| 7,638,325 B2 | 12/2009 | June et al. | |
| 7,723,107 B2 | 5/2010 | Kirkin et al. | |
| 7,745,140 B2 | 6/2010 | June et al. | |
| 7,785,806 B2 | 8/2010 | Warren et al. | |
| 7,785,875 B2 | 8/2010 | Hwang et al. | |
| 7,811,581 B2 | 10/2010 | Middeldorp | |
| 7,846,446 B2 | 12/2010 | Cannon et al. | |
| 7,951,383 B2 | 5/2011 | Murphy et al. | |

(Continued)

FOREIGN PATENT DOCUMENTS

| | | |
|---|---|---|
| CA | 2673432 A1 | 7/2008 |
| CN | 1877336 A | 12/2006 |

(Continued)

OTHER PUBLICATIONS

International Search Report and Written Opinion issued by the International Searching Authority for Application No. PCT/GB2012/053113, dated Mar. 26, 2013, 9 pages.

Anthony et al., "Flow cytometry using annexin V can detect early apoptosis in peripheral blood stem cell harvests from patients with leukemia and lymphoma," Bone Marrow Transplant 21:441-446, 1998.

Ben-Sasson et al., IL-1 acts directly on CD4 T cells to enhance their antigen-driven expansion and differentiation, PNAS 106(17)7119-7124 (2009).

(Continued)

*Primary Examiner* — Michail A Belyavskyi
(74) *Attorney, Agent, or Firm* — Cooley LLP

(57) ABSTRACT

An in vitro expansion process for rapid expansion of antigen specific T cells, such as allogeneic antigen specific T cells comprising the steps culturing in a gas permeable vessel a population of PBMCs (such as allogeneic PBMCs) in the presence of antigen, for example a peptide or peptide mix relevant to a target antigen(s), in the presence of an exogenous cytokine characterized in that the expansion to provide the desired population of T cells is 14 days or less, for example 9, 10, 11 or 12 days, such as 10 days. The disclosure also extends to T cell populations generated by and obtained from the method and the use of same in therapy.

28 Claims, 13 Drawing Sheets
Specification includes a Sequence Listing.

(56) References Cited

U.S. PATENT DOCUMENTS

| | | |
|---|---|---|
| 8,138,314 B2 | 3/2012 | Exley et al. |
| 8,481,051 B2 | 7/2013 | Kuzushima et al. |
| 8,546,137 B2 | 10/2013 | Cannon et al. |
| 8,722,401 B2 | 5/2014 | Groux et al. |
| 8,741,642 B2 | 6/2014 | Manjili et al. |
| 9,115,402 B2 | 8/2015 | Hacohen et al. |
| 9,255,243 B2 | 2/2016 | Wilson et al. |
| 10,556,943 B2 | 2/2020 | Knutson et al. |
| 11,118,164 B2 | 9/2021 | Leen et al. |
| 11,155,784 B2 | 10/2021 | Rooney et al. |
| 11,167,024 B2 | 11/2021 | Leen et al. |
| 2002/0051784 A1 | 5/2002 | Boussiotis et al. |
| 2002/0119121 A1 | 8/2002 | Vitiello et al. |
| 2002/0155108 A1 | 10/2002 | Barbera-Guillem |
| 2003/0148982 A1 | 8/2003 | Brener et al. |
| 2003/0153073 A1 | 8/2003 | Rogers et al. |
| 2003/0219458 A1 | 11/2003 | Wang |
| 2004/0022761 A1 | 2/2004 | Banchereau et al. |
| 2004/0096457 A1 | 5/2004 | Huber et al. |
| 2004/0106159 A1 | 6/2004 | Kern et al. |
| 2005/0028505 A1 | 2/2005 | Schumacher |
| 2005/0106717 A1 | 5/2005 | Wilson et al. |
| 2005/0221481 A1 | 10/2005 | Migliaccio et al. |
| 2006/0045883 A1 | 3/2006 | Molldrem et al. |
| 2006/0073126 A1 | 4/2006 | Shiku et al. |
| 2006/0204509 A1 | 9/2006 | Harty et al. |
| 2006/0251664 A1 | 11/2006 | Kropshofer et al. |
| 2007/0003531 A1 | 1/2007 | Mukherji et al. |
| 2007/0048329 A1 | 3/2007 | Khanna et al. |
| 2007/0098734 A1 | 5/2007 | Cai et al. |
| 2008/0260701 A1 | 10/2008 | Hope |
| 2009/0098090 A1 | 4/2009 | Hart et al. |
| 2009/0305324 A1 | 12/2009 | Kuzushima et al. |
| 2009/0305408 A1 | 12/2009 | Chang |
| 2010/0035282 A1 | 2/2010 | Bonini et al. |
| 2010/0254958 A1 | 10/2010 | Letsch et al. |
| 2011/0059133 A1 | 3/2011 | Adhikary et al. |
| 2011/0136228 A1 | 6/2011 | Wolf |
| 2011/0182870 A1 | 7/2011 | Leen et al. |
| 2011/0236363 A1 | 9/2011 | Chang et al. |
| 2011/0262467 A1 | 10/2011 | Riley et al. |
| 2012/0100180 A1 | 4/2012 | Gao et al. |
| 2012/0244132 A1 | 9/2012 | Stauss et al. |
| 2013/0045491 A1 | 2/2013 | Unutmaz |
| 2013/0058909 A1 | 3/2013 | Szabolcs |
| 2013/0102075 A1 | 4/2013 | Vera et al. |
| 2013/0115617 A1 | 5/2013 | Wilson |
| 2013/0129713 A1 | 5/2013 | Rescigno et al. |
| 2013/0217122 A1 | 8/2013 | Kaplan |
| 2014/0212398 A1 | 7/2014 | Reisner et al. |
| 2015/0010519 A1 | 1/2015 | Leen et al. |
| 2015/0037297 A1 | 2/2015 | Terman |
| 2015/0044258 A1 | 2/2015 | Knaus et al. |
| 2015/0174966 A1 | 6/2015 | Todoroki |
| 2015/0175966 A1 | 6/2015 | Vera et al. |
| 2015/0337262 A1 | 11/2015 | Ethell |
| 2016/0208216 A1 | 7/2016 | Vera et al. |
| 2016/0215351 A1 | 7/2016 | Sahin et al. |
| 2016/0296563 A1 | 10/2016 | Sourdive et al. |
| 2016/0362658 A1 | 12/2016 | Leen et al. |
| 2017/0128565 A1 | 5/2017 | O'Reilly et al. |
| 2018/0187152 A1 | 7/2018 | Leen et al. |
| 2018/0250384 A1 | 9/2018 | Leen et al. |
| 2019/0134092 A1 | 5/2019 | Rainer et al. |
| 2019/0144826 A1 | 5/2019 | Leen et al. |
| 2019/0264176 A1 | 8/2019 | Leen et al. |
| 2020/0172864 A1 | 6/2020 | Chiang et al. |
| 2021/0348127 A1 | 11/2021 | Leen |
| 2022/0001005 A1 | 1/2022 | Leen et al. |
| 2022/0152111 A1 | 5/2022 | Knaus et al. |
| 2022/0169986 A1 | 5/2022 | Leen et al. |
| 2022/0251508 A1 | 8/2022 | Leen et al. |
| 2022/0257654 A1 | 8/2022 | Juan et al. |
| 2022/0282218 A1 | 9/2022 | Leen et al. |
| 2022/0288119 A1 | 9/2022 | Vera et al. |
| 2023/0028788 A1 | 1/2023 | Leung et al. |

FOREIGN PATENT DOCUMENTS

| | | |
|---|---|---|
| WO | WO 1994/002156 | 2/1994 |
| WO | WO 1995/24217 A1 | 9/1995 |
| WO | WO 1995/027722 | 10/1995 |
| WO | WO 1995/31208 A1 | 11/1995 |
| WO | WO 1998/033888 | 8/1998 |
| WO | WO 2000/50569 A1 | 8/2000 |
| WO | WO-02077030 A2 | 10/2002 |
| WO | WO 2005/028505 A2 | 3/2005 |
| WO | WO 2005/035728 A2 | 4/2005 |
| WO | WO-2007097820 A2 | 8/2007 |
| WO | WO-2007099341 A1 | 9/2007 |
| WO | WO 2007/121276 A2 | 10/2007 |
| WO | WO 2008025992 | 3/2008 |
| WO | WO 2008/073312 A2 | 6/2008 |
| WO | WO 2008/073313 A2 | 6/2008 |
| WO | WO 2009/053109 A1 | 4/2009 |
| WO | WO 2011/024482 | 3/2011 |
| WO | WO 2011/028531 A1 | 3/2011 |
| WO | WO 2011/146473 A1 | 11/2011 |
| WO | WO-2012062831 A1 | 5/2012 |
| WO | WO 2013/088114 A1 | 6/2013 |
| WO | WO 2013/088147 A1 | 6/2013 |
| WO | WO-2013088148 A2 | 6/2013 |
| WO | WO 2013/119947 A1 | 8/2013 |
| WO | WO 2015/110397 A2 | 7/2015 |
| WO | WO-2016073550 A1 | 5/2016 |
| WO | WO 2016/073595 A1 | 6/2016 |
| WO | WO 2016/073595 A8 | 6/2016 |
| WO | WO-2016154112 A1 | 9/2016 |
| WO | WO 2017/049291 A1 | 3/2017 |
| WO | WO 2017/203368 A1 | 11/2017 |
| WO | WO 2018/055191 A1 | 3/2018 |
| WO | WO-2018052947 A1 | 3/2018 |
| WO | WO 2018/232467 A1 | 12/2018 |
| WO | WO 2019/050958 A2 | 3/2019 |
| WO | WO-2020198366 A1 | 10/2020 |
| WO | WO-2020227546 A1 | 11/2020 |
| WO | WO-2020255063 A1 | 12/2020 |
| WO | WO 2021/034674 A1 | 2/2021 |
| WO | WO-2021021937 A1 | 2/2021 |
| WO | WO-2021133667 A1 | 7/2021 |
| WO | WO-2021189084 A1 | 9/2021 |
| WO | WO-2022025984 A1 | 2/2022 |
| WO | WO-2022064042 A1 | 3/2022 |
| WO | WO-2023159088 A1 | 8/2023 |

OTHER PUBLICATIONS

Boer et al., "Extensive early apoptosis in frozen thawed CD34+ stem cells decreases threshold doses for haematological recovery after autologous peripheral blood progenitor cell transplant," Bone marrow Transplant 29:249-255, 2002.

Bollard et al., "The generation and characterization of LMP2-specific CTL for use as adoptive transfer from patients with relapsed EBV-positive Hodgkin disease," J. Immunother. Jul.-Aug. 2004; 27(4):317-27.

Burkett et al., "IL-15R expression on CD8+ T cells is dispensable for T cell memory", PNAS, 15 Apr. 15, 2003, 100(8):4724-9. Epub Apr. 1, 2003.

Cha et al., "IL-7 + IL-15 are superior to IL-2 for the ex vivo expansion of 4T1 mammary carcinoma-specific T cells with greater efficacy against tumors in vivo," Breast Cancer Res Treat. Jul. 2010, pp. 1-22.

Cornish et al., "Differential regulation of T-cell growth by IL-2 and IL-15", Blood, Jul. 15, 2006, 108(2):600-8_ Epub 006 Mar. 28.

Dienz and Rincon, "The Effects of IL-6 on CD4 T Cell Responses," Clin Immunol. Jan. 2009; 130(1): 27-33.

Dunne et al. Selective Expansion and Partial Activation of Human NK Cells and NK Receptor-Positive T Cells by IL-2 and IL-15. The Journal of Immunology, 2001, 167: 3129-3138.

(56) References Cited

OTHER PUBLICATIONS

Gerdemann et al., "Cytotoxic T lymphocytes simultaneously targeting multiple tumor-associated antigens to treat EBV negative lymphoma," Molecular Therapy, Nature Publishing Group, GB, 19(12): 2258-2268 (2011).
Gerdemann et al., Generation of Multivirus-specific T Cells to Prevent/treat Viral Infections after Allogeneic Hematopoietic Stem Cell Transplant, Journal of Visualized Experiments, No. 51, (2011), pp. 1-6.
Gerdemann, Ulrike, "Nucleofection of DCs to Generate Multivirus specific T Cells for Prevention or Treatment of Viral Infections in the Immunocompromised Host," Molecular Therapy 17(9):1616-1625 (2009).
Gerdemann, Ulrike, "Rapidly Generated Multivirus-specific Cytotoxic T Lymphocytes for the Prophylaxis and Treatment of Viral Infections," Molecular Therapy 20(8):1622-1632 (2012).
Hemmer et al., "Minimal peptide length requirements for CD4+ T cell clones-implications for molecular mimicry and T cell survival," International Immunology, vol. 12, No. 3, pp. 375-383 (2000).
Hobeika et al. Detailed analysis of cytomegalovirus (CMV)-specific T cells expanded for adoptive immunotherapy of CMV infection following allogeneic stem cell transplantation for malignant disease. Cytotherapy (2008) vol. 10, No. 3, 289-302.
Il-Kang et al., Human bone marrow as a source of multifunctional CMV-specific CD4+T cells for adoptive cell therapy11, Blood, American Society of Hematology, US, vol. 110, No. 11 Part I, Nov. 16, 2007 (Nov. 16, 2007), p. 873A, 2 pages.
Jennes et al. Enhanced ELISPOT detection of antigen-specific T cell responses from cryopreserved specimens with addition of both IL-7 and IL-15—the Amplispot assay. Journal of Immunological Methods 270 (2002) 99-108.
Keirman et al., "PepMix™ Peptide Pools for Clinical Applications: T Cell Therapy for Viral Infections after Hematopoietic Stem Cell Transplant," JPT Peptide Technologies (2012), 2 pages.
Kelly-Rogers et al. Activation-Induced Expression of CD56 by T Cells Is Associated With a Reprogramming of Cytolytic Activity and Cytokine Secretion Profile In Vitro. Human Immunology 67, 863-873 (2006).
Koch CP, Perna AM, Pillong M, Todoroff NK, Wrede P, et al. (2013) Scrutinizing MHC-1 Binding Peptides and Their Limits of Variation. PLoS Comput Biol 9(6): el 003088, 9 pages.
Lapteva et al. OptimizationManufacture of Virus- and Tumor-Specific T Cells. Stem Cells Int. 2011;2011:434392. Epub Sep. 11, 2011.
Leen et al., "Contact-activated monocytes: efficient antigen presenting cells for the stimulation of antigen-specific T cells," J Immunother. Jan. 2007:30(1): 96-107.
Liu et al., "IL-15 mimics T cell receptor crosslinking in the induction of cellular proliferation, gene expression and pytotoxicity in CD8+ memory T cells", Proc Natl Acad Sci US A., Apr. 30, 2002, 99(9):6192-7_ Epub Apr. 23, 2002.
Mielcarek et al., "Suppression of Alloantigen-lnduced T-Cell Proliferation by CD14+ Cells Derived From Granulocyte Colony-Stimulating Factor-Mobilized Peripheral Blood Mononuclear Cells," Blood, vol. 89, No. 5 Mar. 1, 1997: pp. 1629-1634.
Montes et al. Optimum in vitro expansion of human antigen-specific CD8+ T cells for adoptive transfer therapy. Clin Exp Immunol. Nov. 2005; 142(2): 292-302.
Montfoort et al. Antigen storage compartments in mature dendritic cells facilitate prolonged cytotoxic T lymphocyte cross-priming capacity. PNAS. 2009. 106:166730-6735.
Nawa et al., "G-CSF reduces IFN-g and IL-4 production by T cells after allogeneic stimulation by indirectly modulating monocyte function," Bone Marrow Transplantation (2000) 25, 1035-1040.
Professor Kronenberg Declaration filed in EP 12815750 Opposition on May 15, 2019, 75 pages.
Redchenko and Rickinson, "Accessing Epstein-Bar Virus-Specific T-Cell Memory with Peptide-Loaded Dendritic Cells," Journal of Virology Jan. 1999, vol. 73, No. 1, p. 334-342.
Reyes et al., "Granulocyte colony-stimulating factor (G-CSF) transiently suppresses mitogen-stimulated T-cell proliferative response," British Journal of Cancer (1999) 80(1/2):229-235 (1999).
Rooney and Leen, "Moving Successful Virus-specific T-cell Therapy for Hematopoietic Stem Cell Recipients to Late Phase Clinical Trials," Molecular Therapy-Nucleic Acids (2012) I, e55, 4 pages.
Schmid et al., "Dead Cell Discrimination with 7-aminoactinomycin Din Combination with Dual Colour Immunofluorescence in Single Laser Flow Cytometry," Cytometry 13:204-208 (1992).
Shantaram et al., "Decreased immune functions of blood cells following mobilization with granulocyte colony-stimulating factor: association with donor characteristics," Blood 98(6):1963-1970 (2001).
Sili et al., "Large-scale expansion of dendritic cell-primed polyclonal human cytotoxic T-lymphocyte lines using lymphoblastoid cells for adoptive immunotherapy," J. Immuother. May-Jun. 2003: 26(3):241-56.
Tan et al, "A re-evaluation of the frequency of CD8+ T cells specific for EBV in healthy virus carriers", Journal of mmunology, Feb. 1, 1999;162(3):1827-35.
Teague et al., "Interleukin-IS rescues tolerant cos+ T cells for use in adoptive immunotherapy of established tumors," Nature Medicine 12(3):335-341 (2006).
Trivedi et al. Generation of CMV-specific T lymphocytes using protein-spanning pools of pp65-derived overlapping pentadecapeptides for adoptive immunotherapy. Blood. Apr. 1, 2005;105(7):2793-801. Epub Oct. 28, 2004.
Tung et al., "Modern Flow Cytometry: A Practical Approach," Clin Lab Med 27(3):453 (2007), 15 pages.
Vella et al. Cytokine-induced survival of activated T cells in vitro and in vivo. Proc Natl Acad Sci US A. Mar. 31, 1998;95(7):3810-5.
Vera et al., "Accelerated Production of Antigen-specific T Cells for Preclinical and Clinical Applications Using Gas-permeable Rapid Expansion Cultureware (G-Rex)," Journal of Immunotherapy 33(3):305-315 (2010).
Wing et al., "An Improved Method for the Detection of Cell Surface Antigens in Samples of Low Viability using Flow Cytometry," J Immunol Methods 126: 21-27 1990.
Zhou et al., Either IL-2 or IL-12 Is Sufficient to Direct Thl Differentiation by Nonobese Diabetic T Cells[1], The Journal of Immunology, 2003, 170:735-740.
Adamowicz et al., 2019, Interferon-Gamma Elispot Assay: Unique Challenges of Validating Immune Monitoring Assays in a Regulated Environment celerion Translating Science to Medicine pp. 1-4.
Aguayo-Hiraldo et al., "Characterizing the Cellular Immune Response to Parainfluenza Virus 3," The Journal of Infectious Diseases 216:153-161 (2017).
Amary et al, "Detection of SS18-SSX fusion transcripts in formalin-fixed paraffin-embedded neoplasms: analysis of conventional RT-PCR, qRT-PCR and dual color FISH as diagnostic tools for synovial sarcoma," Modern Patholoty 20:482-496 (2007).
Ando et al., "Towards Phase 213 Trials for Epstein-Barr Virus (EBV)-Associated Malignancies," Blood (ASH Annual Meeting Abstracts) 118, Abstract 4043, 2 pgs., 2011.
Arons et al., "Prame Expression in Hair Cell leukemia," Leukemia Research, New York, NY US 32(9):1400-1406 (2008).
Bensussan et al. "Detection of membrane-bound HLA-G translated products with a specific monoclonal antibody", Proc. Natl. Acad. Sci. USA, 92:10292-10296, 1995.
Binggeli et al., "Polyomavirus BK—Specific Cellular Immune Response to VP1 and Large T-Antigen in Kidney Transplant Recipients," American Journal of Transplantation, 2007, vol. 7, pp. 1131-1139.
Blyth et al., "BK Vims-Specific T Cells for Use in Cellular Therapy Show Specificity to Multiple Antigens and Polyfunctional Cy1okine Responses", Transplantation, 92(10):1077-1084, 2011.
Blyth et al., "Bk Virus Specific T Cells Expanded Ex Vivo for Use in Cellular Therapy Show Multiple Antigen Specificity and Polyfunctional THI Responses", abstract #164, S215, 1 page.
Britten et al., "The use of HLA-A*0201-transfected K562 as standard antigen-presenting cells for CD8+ T lymphocytes in IFN-gamma ELISPOT assays," J. Immunol. Methods 259, 95-110, 2002.

(56) References Cited

OTHER PUBLICATIONS

Calarota et al. "Detection of Epstein-Barr virus-specific memory CD4+T cells using a peptide-based cultured enzyme-linked immunospot assay", Immunology, 2013: 139: 533-544.

Can and Karahuseyinoglu, "Concise review: human umbilical cord stroma with regard to the source of fetus-derived stem cells", Stem Cells, 25:2886-2895, 2007.

Carpenter et al., "A side-by-side comparison of T cell reactivity to fifty-nine Mycobacterium tuberculosis antigens in Diverse populations from five continents", Tuberculosis 95(6)713-721 (2015).

Carrasco et al., "Vaccination of a Melanoma Patient with Mature Dendritic Cells Pulsed with MAGE-3 Peptides Triggers the Activity of Nonvaccine Anti-Tumor Cells," The Journal of Immunology 180(5):3585-3593 (2008).

Chakera et al., "Antigen-specific T cell responses to BK polyomavirus antigens identify functional antiviral immunity and may help to guide immunosuppression following renal transplantation," Clin Exp. Immunol (3):401-409 (2011).

Chia, Whay-Kuang, et al.; Adoptive T-Cell Transfer and Chemotherapy in the First-Line Treatment of Metastic and/or Locally Recurrent Nasopharyngeal Carcinoma; The Am. Society of Gene & Cell Therapy, Molecular Therapy; pp. 1-8; Jul. 29, 2013.

Dasari et al., "Prophylactic and therapeutic adenoviral vector-based multivims-specific Tcell immunotherapy for transplant patients", Mol. Ther., 3:16058, 2016, 9 pages.

Decaussin et al., "Expression of BARF1 Gene encoded by Epstein Barr Virus in Nasopharyngeal Carcinoma Biopsies," Cancer Res. 60, 5584-5588 (2000).

Foster et al., "Autologous Designer Antigen-presenting Cells by Gene Modification of T Lymphocytes Blasts With IL-7 and IL-12," J. Immunother. 30, 506-16, 2007.

Fujita et al.,"Exploiting cytokine secretion to rapidly produce multivirus-specific T cells for adoptive immunotherapy," J Immunother. 31(7):665-674 (2008).

Fujiwara et al., "Identification and in vitro expansion of CD4+ and CD8+ T cells specific for human neutrophil elastase," Blood 103(8):3076-3083 (2004).

Gaundar et al., "The Generation of Clinical Grade Aspergillus Fumigatus (AF) Specific Immune Cells for Adoptive immunotherapy", abstract #168, S216, 1 page.

Gerdemann et al., "Immunotherapeutic strategies to prevent and treat human herpesvirus 6 reactivation after allogeneic stem cell transplantation", BLOOD, Jan. 3, 2013, vol. 121, No. 1, p. 207-218.

Gerdemann et al., "Safety and clinical efficacy of rapidly-generated trivirus-directed T cells as treatment for adenovirus, EBY, and CMV infections after allogeneic hematopoietic stem cell transplant", Molecular Therapy 2(11):2112-2121 (2013).

Gerdemann, et al.; "Multivirus-Specific CTL for Adaptive Transfer Using In Vitro Pepmix Stimulation", Biology Blood Marrow Transplant, online Jan. 28, 2011, p. S216.

Geyeregger et al. "Short-Term In-Vitro Expansion Improves Monitoring and Allows Affordable Generation of Virus-Specific T-Cells against Several Viruses for a Broad Clinical Application" PLoS One, 2013, 8(4): e59592.

Goon et al., "Human T Cell Lymphotropic Virus (HTLV) Type-1—Specific CD8+ Cells: Frequency and Immunodominance Hierarchy", The Journal of infectious Diseases, Jun. 15, 2004;189: 2294-2298.

Goon et al., "Human T Cell Lymphotropic Virus Type I (HTLV-1)—Specific CD4+ T Cells: immunodominance Hierarchy and Preferential Infection with HTLV-11", The Journal of Immunology, 2004, 172: 1735-1743.

Halawi et al., "Identification of novel CD8+ T cell epitopes in human herpesvirus 68 U11 and U90", Immunity, inflammation and Disease 2015; 3(2): 1 18-131.

Herd et al., "Major Histocompatibility Complex Class I Cytotoxic T Lymphocyte Immunity to Human Metapneumovirus hMPV) in individuals with Previous hMPV Infection and Respiratory Disease", The Journal of infectious Diseases, Feb. 15, 2008;197:584-92.

Hunder et al., "Treatment of Metastatic Melanoma with Autologous CD4+t Cells Against NY-ESO-1," New England Journal of Medicine 358(25):2698-2703 (2008).

Huye et al., "Combing mTor Inhibitors With Raparnycin-resistant T Cells: A Two-pronged Approach to Tumor Elimination," Mol. Ther. 19, 2239-48, 2011.

International Preliminary Report on Patentability issued by the International Searching Authority for Application No. PCT/US2013/025342, dated Aug. 12, 2014, 6 pages.

International Preliminary Report on Patentability issued by the International Searching Authority for Application No. PCT/US2016/052487, dated Mar. 20, 2018, 9 pages.

International Preliminary Report on Patentability issued in International Application No. PCT/US2010/025209, dated Sep. 9, 2011.

International Search Report and Written Opinion issued by the International Searching Authority for Application No. PCT/US20/46389, dated Nov. 13, 2020, 10 pages.

International Search Report and Written Opinion issued by the International Searching Authority for Application No. PCT/US2020044080, dated Jul. 29, 2020, 26 pages.

International Search Report and Written Opinion issued in International Application No. PCT/US2010/46505, dated Oct. 14, 2010, 6 pages.

International Search Report and Written Opinion issued in International Application No. PCT/US2013/025342, dated Apr. 11, 2013, 7 pages.

International Search Report and Written Opinion issued in International Application No. PCT/US2016/052487, dated Dec. 19, 2016, 11 pages.

International Search Report and Written Opinion issued in International Application No. PCT/US2020/024726, dated Jun. 19, 2020, 15 pages.

International Search Report issued in International Application No. PCT/US2010/025209 , dated Jul. 14, 2010, 8 pages.

Jacobs et al., "Lab. Investigation—Human/Animal Tissue Selective Cancer-Germline Gene Expression in Pediatric Brain Tumors," J Neurooncol, pp. 273-280 (2008).

Janetzki et al., Guidelines for the automated evaluation of Elispot assays, 2015 Nature Protocols 10(7): 1098-1115 (2015).

Jeffes III et al. "Therapy of recurrent high grade gliomas with surgery, and autologous mitogen activated IL-2 stimulated killer {MAK} Lymphocytes: I. Enchancement of MAK lytic activity and cytokine production by PHA and clinical use of PHA" Journal of Neuro-Oncology, 1993, vol. 15, pp. 141-155.

Jeras et al., "Induction/Engineering, Detection, Selection, and Expansion of Clinical-Grade Human Antigen-Specific CDS+ Cytotoxic T Cell Clones for Adoptive Immunotherapy," Journal of Biomedicine and Biotechnology, vol. 2010, Article ID 705215, 2010, 15 pages.

Kedl et al; "T Cells Compete for Antigen-bearing Antigen presenting Cells"; J.P. Med.—The Rockfeller University Press vol. 192, No. 8, Oct. 16, 2002.

Kedl et al; "T Cells Down-Modulate Peptide-MHC Complexes on APCs in vivo"; Published online: Dec. 3, 2001, DOI: 10.1 038/ni/742; 2002 Nature Publishing Group.

Khan et al., "T Cell Recognition Patterns of Immunodominant Cytomegalovirus Antigens in Primary and Persistent infection", The Journal of Immunology, 2007, 178: 4455-4465.

Khanna et al., "Generation of a multipathogen-specific T-cell product for adoptive immunotherapy based on activation-dependent expression of CD154,"Blood, Jul. 2011, vol. 118, No. 4, pp. 1121-1131.

Kim et al., "The ABCs of artificial antigen presentation", Nature Biotechnology, 22(4):403-410 (2004).

Kindt et al., "Protective Role of the Inhibitor of Apoptosis Protein, Survivin, in Toxin-Induced Acute Renal Failure," The FASEB Journal, Federation of American Societies for Experimental Biology, US 22(2):510-521 (2008).

Lee et al, HLA A2.I—restricted Cytotoxic T cells Recognizing a Range of Epstein-Barr Virus Isolates through a Defined Epitope in Latent Membrane Protein LMP2, Journal of Virology, Dec. 1993, p. 7428-7435.

(56) References Cited

OTHER PUBLICATIONS

Leen et al. "Multicenter study of banked third-party virus-specific Tcells to treat severe viral infection after hematopoietic stem cell trans plantation," Blood 121(26):5113-5123 (2013).

Leen et al., "Cytotoxic lymphocyte (CTL) therapy for the treatment of EBV negative tumors," Abstract, International Society for Cell and Gene Therapy of Cancer Annual Meeting held in Cork, Ireland, presented Sep. 4, 2009, 1 page.

Leen et al., "Identification of hexon-specific CD4 and CDS T-cell epitopes for vaccine and immunotherapy," Journal of Virology, 82(1):546-554, 2008.

Leen et al., "Monoculture-derived T lymphocytes specific for multiple viruses expand and produce clinically relevant effects in immunocompromised individuals," Nature Medicine, 2006, vol. 12, No. 10, pp. 1160-1166.

Leen et al., "Overcoming antigenic competition to produce multispecific cytotoxic T lymphocyte lines for adoptive transfer", American Society for Blood and Marrow Transplantation, Feb. 2009, No. 374, p. 134.

Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Nov. 2008, 1 page.

Liao et al., "Transfection of RNA encoding tumor antigens following maturation of dendritic cells leads to prolonged presentation of antigen and the generation of high-affinity tumorreactive cytotoxic T lymphocytes," Molecular Therapy 9(5):757-764 (2004).

Lim et al., "Identification of HLA-A*2402-restricted HCMV immediate early-1 (IE-1) epitopes as targets for CD8+ HCMV-specific cytotoxic T lymphocytes," Journal of Translational Medicine 7(72), pp. 1-11 (2009).

Maecker et al., "Use of overlapping peptide mixtures as antigens for cytokine flow cytometry," Journal of Immunological Methods, 2001, vol. 255 (1-2), pp. 27-40.

Meij et al., "dentification and prevalence of CD8+ T-cell responses directed against Epstein-Barr virus-encoded latent membrane protein 1 and latent membrane protein 2," Int. J. Cancer 99:93-99 (2002).

Merlo et al., "The interplay between Epstein-Barr virus and the immune system: a rationale for adoptive cell therapy of EBY-related disorders," Haematologica 95, 1769-77, 2010.

Merrick et al., "Autologous versus allogeneic peptide-pulsed dendritic cells for anti-tumour vaccination: expression of allogeneic MHC supports activation of antigen specific T cells but impairs early naive cytotoxic priming and anti-tumor therapy," Cancer Immunol. Immunother. 57, 897-906, 2008.

Morandi et al.,"Tumor mRNA—Transfected Dendritic Cells Stimulate the Generation of CTL That Recognize Neuroblastoma Associated Antigens, Kill Tumor Cells: Immunotherapeutic Implications," NEOPLASIA 8(10):833-842 (2006).

Muftuoglu et al., "Use of Expanded Allogeneic Third Party BK Vims Specific Cytotoxic C6. T Cells to Target Progressive Multifocal Leukoencephalopathy",Am. Soc. Hematol., abstract #98495, 128(22):3365, 2016.

Na et al., "Human Bone Marrow as a Source of Multifunctional CMV-Specific CD4+ T Cells for Adoptive Cell Therapy" Blood, 2007, vol. 110, p. 2973.

Nair et al., "Induction of tumor-specific cytotoxic T lymphocytes in cancer patients by autologous tumor RNA transfected dendritic cells," Annals of Surgery 235(4):540-549 (2002).

Olson et al., "Efficacy of Third Party BK Vims {BKV) Specific Cytotoxic T-Lymphocytes Generated By Ex Vivo Expansion for the Treatment of BKV Infection in Stem Cell Transplant Recipients, a Phase 2 Trial", Am. Soc. Hematol., Abstract, 128(22):504, 2016.

Paul et al Development and validation of a broad scheme for prediction of HLA class II restricted T cell epitopes Journal of Immunological Methods 422 (2015) 28-34.

PepMix™ Peptide Pools retrieved on Mar. 1, 2021 from https://www.jpt.com/products/pepmix-peptide-pools. pp. 1-14.

PepTivator® CMV pp65—premium grade, MACS and Peptivator, Miltenyi Biotech GmbH 2013, 4 pages.

Peripheral blood mononuclear cell—Wikipedia; pp. 1-3; Retrieved on Mar. 3, 2021 from https://en.wikipedia.org/wiki/Peripheral_blood_mononuclear_cell.

Quintarelli et al., "Cytotoxic T lymphocytes directed to the preferentially expressed antigen of melanoma {PRAME) Target chronic myeloid leukemia", Blood, 112(5), pp. 1876-1885 (2008).

Ramaswami et al., "The Polyomavirus BK Large T-Antigen-Derived Peptide Elicits an HLA-DR Promiscuous and Polyfunctional CD4 T-Cell Response," Clin Vaccine Immunol 18(5):815-824 (2011).

Ray et al., "Role of Individual Glycoproteins of Human Parainfluenza Virus Type 3 in the Induction of a Protective immune Response", Journal of Virology, Mar. 1988, vol. 62, No. 3, pp. 783-787.

Rudolf et al., "Potent costimulation of human CD8 T cells by anti-4-1BB and anti-CD28 on synthetic artificial antigen presenting cells," Cancer Immunol. Immunother. 57, 175-183 (2007).

Schnittger et al., in Blood, CBL Mutations Are Correlated with CMML, Frequently Associated with RUNX1 but Mutually Exclusive of JAK2V617F Mutations, BLOOD 114(22):962, 2 pages (Nov. 20, 2009).

Sieg et al., Infection and Immunoregulation of T Lymphocytes by Parainfluenza Virus Type 3. Proceedings of the National Academy of Sciences of the U. S. A. 91(14):6293-6297 (1994).

Song et al., "Detection of MAGE and SSX Gene Expressions by RT-nested PCR Using Common Primers in Head and Neck Cancer," Clinical and Experimental Otorhinolaryngology 1(2):97-102 (2008).

Suhoski et al., "Engineering artificial antigen-presenting cells to express a diverse array of co-stimulatory molecules," Mol. Ther. 15, 981-88, 2007.

Suneetha et al., "Effect of peptide pools on effector functions of antigen-specific CD8+ T cells," Journal of Immunological Methods, 342:(1-2)33-48 (2009).

Taylor et al., "Mechanisms of immune suppression by interleukin-10 and transforming growth factor—β: the role of T regulatory cells," Immunology 117, 433-42, 2006.

Tekkatte, Chandana, et al;""Humanized" Stem Cell Culture Techniques: The Animal Serum Controversy," Stem Cells Int'l, vol. 2011; Article ID 504723; 14 pgs; Nov. 9, 2010.

Testa et al: "MHC Class I—Presented T Cell Epitopes Identified by Immunoproteomics Analysis Are Targets for a :ross Reactive Influenza-Specific T Cell Response", PLOS One 7(11):48484 (2012), 11 pages.

Turtle & Riddell, "Artificial antigen presenting cells for use in adoptive immunotherapy," Cancer J. 16, 374-81, 2010.

Tzannou et al. ""Mini" bank of only 8 donors supplies CMV-directed T cells to diverse recipients," Blood Advances 3(17):2571-2580 (2019).

Tzannou et al., "Immunologic Profiling of Human Metapneumovirus for the Development of Targeted Immunotherapy," Journal of Infectious Diseases 216:678-687 (2017).

Tzannou et al., "Preventing Stem Cell Transplantation-associated Viral Infections using T-cell Therapy," Immunotherapy. 7(7):793-810 (2015).

Withers et al. "Establishment and Operation of a Third-Party Virus-Specific T Cell Bank within an Allogeneic Stem Cell Transplant Program," Biology of Blood and Marrow Transplantation, 24:2433-2442 (2018).

Ye et al., In Vitro expansion and Characterization of Dendritic Cells Derived from Human Bone Marrow CD34+Cells; Bone Marrow Transplant, 1996, v 18. 997-1008.

Zhu et al.,"Generation of cytotoxic T-cell lines using overlapping pentadecapeptides drived from conserved regions of the adenovirus hexon protein," Journal of General Virology 1577-1589 (2010).

Ahmed et al, "Preliminary Identification of Potential Vaccine Targets for the COVID-19 Coronavirus (SARS-CoV-2) Based on SARS-CoV Immunological Studies," Viruses 12(3):254, pp. 1-15 (2020).

Diao et al., "Reduction and Functional Exhaustion of T Cells in Patients with Coronavirus Disease 2019," Front. Immunol. 11:827, pp. 1-7 (2020).

Fast et al., "Potential T-cell and B-cell Epiotpes of 2019-nCOV," BIOrXIV, pp. 1-9 (2020).

(56) References Cited

OTHER PUBLICATIONS

Gerdeman et al., Blood, 2009, v.114, Abstract 4083, 2 pages.
Grifoni et al., "A Sequence Homology and Bioinformatic Approach Can Predict Candidate Targets for Immune Responses to SARS CoV-2," Cell Host & Microbe 27(40):671-680 (2020).
Kumar et al., "Structural, glycosylation and antigenic variation between 2019 novel coronavirus (2019-nCoV) and SARS coronavirus (SARS-CoV)," Virusdisease 31(1):13-21 (2020).
Li et al, "T Cell Responses to Whole SARS Coronavirus in Humans," The Journal of Immunology 181(8):5490-5500 (2008).
Itoh et al., Specific Immunity Against Human Epithelial Cancer, Nishinihon Journal of Urology 60:185-190 (1998).
Thevarajan et al., "Breadth of concomitant immune responsesprior to patient recovery: a case report of non-severe COVID-19," Nature Medicine 26(4):453-455 (2020).
Vasileiou et al., "Allogeneic, Off-the-Shelf, Sars-Cov-2-Specific T Cells to Treat High-Risk Patients with COVID-19," Transplantation and Cellular Therapy 27, 3S, S1-S488, 3 pages (2021).
Zerlik et al., Blood, 2006, v.1 08 pp. 3865-3870.
Leen et al., "Differential Immunogenicity of Epstein-Barr Virus Latent-Cycle Proteins for Human CD4+ T-Helper 1 Responses," Journal of Virology, The American Society for Microbiology 75(18):8649-8659 (2001).
Tedcastle et al., The Characterization of Monoclonal Antibodies to Human Metapneumovirus and the Detection of Multiple Forms of the Virus Nucleoprotein and Phosphoprotein Journal of Medical Virology 84:1061-1070 (2012).
AlloVir Announces Positive Final Results in Phase 2 Posoleucel Multi-Virus Prevention Study in Oral Presentation at the 64th ASH Annual Meeting and Exposition, Business Wire, Sonia Choi, AlloVir, Dec. 10, 2022, 3 pages.
Anonymous: "AlloVir", "2 Posoleucel (Viralym-M, ALVR105): A multi-virus specific T cell Therapy (VST) targeting five devastating viral pathogens," Jan. 18, 2022 (Jan. 18, 2022), XP093010987, Retrieved from the Internet: URL:https://web.archive.org/web/20220118102I42/https://www.a11ovir.com/products/a1vr105 [retrieved on Jan. 2, 2023] , 6 pages.
Arasaratnam et al. Dynamics of virus-specific T cell immunity in pediatric liver transplant recipients. Am J Transplant 18(9): 2238-2249 (Sep. 2018).
Baugh et al. Infusion of cytotoxic T lymphocytes for the treatment of viral infections in hematopoietic stem cell transplant patients. Curr Opin Infect Dis. 31(4): 292-300 (Aug. 2018).
Heslop and Leen. T-cell therapy for viral infections; American Society of Hematology 2013:342-347 (2013).
Jenkins et al., "In Vivo Activation of Antigen-Specific CD4 T Cells," Annu. Rev. Immunol. 19:23-45 (2001).
Nelson et al., "Virus-specific T-cell therapy to treat BK polyomavirus infection in bone marrow and solid organ transplant recipients," Blood advances, pp. 5745-5754 (Nov. 20, 2020).
Ngo "Towards Phase 2/3 Trials for Epstein-Barr Virus (EBV)-Associated Malignancies," 2011 Graduate Student Symposium of the Graduate School of Biomedical Sciences at Baylor College of Medicine, p. 231, 2011, 3 pages.
Papadopoulou et al. Activity of broad-spectrum T-cells as treatment for AdV, EBV, CMV, BKV, and HHV6 infections after HSCT; Sci Transl Med. 6(242), pp. 1-23 (2014).
Sanjeet et al., "Posoleucel (ALVR105), an Off-the-Shelf, Multivirus-Specific T-Cell Therapy, for the Prevention of Viral Infections Post-Allogeneic Hematopoietic Cell Transplantation (allo-HCT): Results from an Open-Label Cohort of a Phase 2 Trial", Transplantation and Cellular Therapy, Elsevier, Amsterdam, NL, vol. 28, No. 3, Nov. 5, 2021 (Nov. 5, 2021), 2 pages.
Tzannou and Leen; Accelerating immune resconstitution after hematopoietic stem cell transplantation: Clinical & Translational Immunology 3 e11, pp. 1-10 (2014).
Tzannou, I., et al., "Off-the-Shelf Virus-Specific T Cells to Treat BK Virus, Human Herpesvirus 6, Cytomegalovirus, Epstein-Barr Virus, and Adenovirus Infections After Allogeneic Hematopoietic Stem-Cell Transplantation," Journal of Clinical Oncology 35(31), pp. 3547-3557 (Nov. 1, 2017).
Vasileiou et al., Rapid Generation of multivirus-specific T lymphocytes for the prevention and treatment of respiratory viral infection., Haematologica; 105(1):235-243 (2020).
Extended European Search Report issued by the European Patent Office for Application No. 10814245.6, dated Feb. 7, 2013, 5 pages.
Extended European Search Report issued by the European Patent Office for Application No. 13746524.1, dated Jul. 20, 2015, 7 pages.
Extended European Search Report issued by the European Patent Office for Application No. 16180607.0, dated Sep. 27, 2016, 7 pages.
Extended European Search Report issued by the European Patent Office for Application No. 16847545.7, dated Mar. 20, 2019, 9 pages.
Extended European Search Report issued by the European Patent Office for Application No. 19178235.8, dated Oct. 16, 2019, 7 pages.
Extended European Search Report issued by the European Patent Office for U.S. Appl. No. 21/160,943, dated May 21, 2021, 7 pages.
Extended European Search Report issued by the European Patent Office for U.S. Appl. No. 22/166,731, dated Oct. 10, 2022, 6 pages.
International Preliminary Report on Patentability issued by the International Searching Authority for Application No. PCT/GB2012/053113, dated Feb. 10, 2014, 15 pages.
International Search Report dated Aug. 10, 2012 in PCT/GB2012/050896, 11 pages.
International Search Report issued in International Application No. PCT/US2021/016266 , dated Jun. 4, 2021, 18 pages.
International Search Report issued in International Application No. PCT/US2021/070291, dated Jun. 29, 2021, 21 pages.
Leung et al. "Evaluation of cyclin A 1-specific T cells as a potential treatment for acute myeloid leukemia," Blood Adv, Jan. 28, 2020 (Jan. 28, 2020), vol. 4, pp. 387-397.
Mitchell et al., "Determination of Optimal Target Antigen and Immune Modulatory Approaches to Improve and Standardize Epstein-Barr Virus-Specific Adoptive T Cell Therapy", Blood, American Society of Hematology, US 124(21):p. 5817, 3 pages, Nov. 14, 2014.
Pfeiffer et al., "Posoleucel, an Allogeneic, Off-the-Shelf Multivirus-Specific T-Cell Therapy, for the Treatment of Refractory Viral Infections in the Post-HCT Setting," Cliical Cancer Research 324-330 (2023).
Blyth et al., "Donor-derived CMV-specific T cells reduce the requirement for CMV-directed pharmacotherapy after allogeneic stem cell transplantation," Blood. 121:18:3745-3758. May 2, 2013, Pre-published online Feb. 22, 2013.
Blyth et al., in Blood, {Nov. 20, 2009) vol. 114, No. 22, pp. 962, Meeting Info.: 51st Annual Meeting of the American-sociely-of-Hematology, New Orleans, LA, USA. Dec. 5-8, 2009, Amer Soc Hematol.
Carrum et al., "Targeting Lymphomas Using Non-Engineered, Multi-Antigen Specific T Cells", Blood, American Society of Hematology US, vol. 132, Nov. 29, 2018 (Nov. 29, 2018), p. 1685.
Caruso et al., "Flow cytometric analysis of activation markers on stimulated T cells and their correlation with cell proliferation,". Cytometry. Jan. 1, 1997;27(1):71-76.
Clancy et al., "Cytomegalovirus (CMV) PP65 Specific T Cells Expanded from Mobilised Peripheral Blood Stem Cell PBSC) Collections for Prophylactic Adoptive Immunotherapy," Biology of Blood and Marrow Transplantation, 2011. 2, vol. 17, No. 2, Supplement, p. S212, No. 160, 1 page.
Clinical Trials NCT01948180, dated Sep. 23, 2013, 8 pages. Retrieved May 23, 2023, from https://clinicaltrials.gov/ct2/show/NCT01948180.
ClinicalTrial_NCT02108522, Anonymous: "Multivirus-specific T Cells for the Treatment of Virus Infections After Stem Cell Transplant (Charms)", Study Record—ClinicalTrials.gov, 21 pages, retrieved on Aug. 1, 2023 from https://www.clinicaltrials.gov/search?term=NCT02108522.

(56) References Cited

OTHER PUBLICATIONS

"CMD-003", dated 2015, Retrieved from the Internet Sep. 22, 2015, The Wayback Machine—https://web.archive.org/web/20150906200237/http://www.cellmedica.co.uk:80/clinical-research/cmd-003/, 1 page.

Curotto De Lafaille et al., "CD25-T Cells Generate CD25+Foxp3+ Regulatory T Cells by Peripheral Expansion," The Journal of Immunology, vol. 173, No. 12:7259-7268, Dec. 15, 2004.

Dadwal, Poster Abstract 471, "Posoleucel (ALVR105), an Off-the-Shelf, Multivirus-Specific T-Cell Therapy, for the Prevention of Viral Infections Post-Allogeneic Hematopoietic Cell Transplantation (allo-HCT): Results from an Open-Label Cohort of a Phase 2 Trial," Abstracts/Transplant Cellular Therapy, 28, S369-370, Nov. 2021, 2 pgs.

Dadwal, Sanjeet et al., "Posoleucel (ALVR105), an Off-the-Shelf, Multivirus-Specific T-Cell Therapy, for the prevention of Viral Infections Post-Allogeneic Hematopoietic Cell Transplantation (Allo-HCT): Results from an Open-Label Cohort of a Phase 2 Trial," 16 pages. Retrieved from https://docs.publicnow.com/viewDoc?hash_primary=174944531E2578BE2113C21656B176A3520CC307.

Dadwal, Sanjeet et al., Posoleucel (ALVR105), an Off-the-Shelf, Multivirus-Specific T-CeLL Therapy, for the Prevention of Viral Infections Post-Allogeneic Hematopoietic Cell Transplantation (allo-HCT): Results from an Open-Label Cohort of a Phase 2 Trial, Blood, vol. 138, Supplement 1, Nov. 23, 2021, pp. 1760-1762, 3 pages. (Poster Abstracts).

Extended European Search Report issued by the European Patent Office for Application No. 20777790.5, dated Apr. 4, 2023, 7 pages.

Extended European Search Report issued by the European Patent Office for Application No. 20847823, dated Jul. 24, 2023, 12 pages.

Feuchtinger et al. Safe adoptive transfer of virus-specific T-cell immunity for the treatment of systemic adenovirus infection after allogeneic stem cell transplantation. 2006. British Journal of Haematology, 134, 64-76.

Gottlieb et al., "Prophylactic antigen-specific T-cells targeting seven viral and fungal pathogens after allogeneic haemopoietic stem cell transplant," Clinical & Translational Immunology 10: e1249, pp. 1-18 (2021). Accepted Jan. 12, 2021.

Hanley et al. "Expansion of T cells targeting multiple antigens of cytomegalovirus, Epstein-Barr virus and adenovirus o provide broad antiviral specificity after stem cell transplantation," Biology of Blood and Marrow Transplantation, 2011, 02, vol. 17, No. 2, Supplement, p. S212 No. 159, 1 page.

Hasskari et al, "Induction of graft versus malignancy effect after unrelated allogeneic PBSCT using donor lymphocyle infusions derived from frozen aliquots of the original graft", Bone Marrow Transplantation, vol. 47, No. 2, Apr. 4, 2011, pp. 277-282.

Herd, K., et al., "Cytotoxic T-Lymphocyte Epitope Vaccination Protects against Human Metapneumovirus Infection and Disease in Mice", Journal of Virology, 2006, vol. 80, No. 4, p. 2034-2044.

Ifigeneia et al., "Off-the-Shelf Virus-Specific T Cells to Treat BK Virus, Human Herpesvirus 6, Cytomegalovirus, Epstein-Barr Virus, and Adenovirus Infections After Allogeneic Hematopoietic Stem-Cell Transplantation," Journal of Clinical Oncology. 3547-3557 (Aug. 7, 2017).

International Preliminary Report on Patentability for Application No. PCT/US2020/044080, dated Feb. 1, 2022, 17 pages.

International Preliminary Report on Patentability issued in International Application No. dated Jun. 17, 2014 in PCT/GB2012/050896, 8 pages.

International Preliminary Report on Patentability issued in International Application No. PCT/US2020/065968, dated Jun. 28, 2022, 17 pages.

International Preliminary Report on Patentability issued in International Application No. PCT/GB2012/053114, dated Jun. 17, 2014, 5 pages.

International Preliminary Report on Patentability issued in International Application No. PCT/US2020/024726, dated Sep. 28, 2021, 8 pages.

International Preliminary Report on Patentability issued in International Application No. PCT/US2021/016266, dated Jan. 31, 2023, 9 pages.

International Search Report and Written Opinion for International Application No. PCT/IB2022/061291 dated Mar. 29, 2023, 18 pages.

International Search Report dated Mar. 23, 2021 issued during examination of International Application No. PCT/US2020/065968 and Written Opinion, 19 pages.

International Search Report issued in International Application No. PCT/GB2012/053114, dated Jul. 15, 2013, 8 pages.

Joshi, Shantaram et al., "Decreased immune functions of blood cells following mobilization with granulocyte colony-stimulating factor: association with donor characteristics," Blood 98(6):1963-1970 (2001).

Kikuta; Hideaki, "Human metapneumovirus," Uirusu . Dec. 2006;56(2):173-81. doi: 10.2222/jsv.56.173.

Korbling et al., "Donor lymphocyte apheresis for adoptive immunotherapy compared with blood stem cell apheresis," J Clin Apher. 2001;16(2):82-7.

Micklethwaite et al., "Ex Vivo Expansion and Prophylactic Infusion of CMV-pp65 Peptide-Specific Cytotoxic T-Lymphocytes following Allogeneic Hematopoietic Stem Cell Transplantation," Biology of Blood and Marrow Transplantation 13:707-714 (2007).

Olson et al., "Third-Party BK Virus-Specific Cytotoxic T Lymphocyte Therapy for Hemorrhagic Cystitis Following Allotransplantation," J Clin Oncol 39:2710-2719 (2021).

Parks et al., "Flow Cytometry and Fluorescence-Activated Cell Sorting (FACS)," Handbook of Experimental Immunology, Chapter 29, DM Weir (ed), Blackwell Scientific Publications, MA, 1986, 23 pages.

Peggs et al. "Directly Selected Cytomegalovirus-Reactive Donor T Cells Confer Rapid and Safe Systemic Reconstitution of Virus-Specific Immunity Following Stem Cell Transplantation", Clinical Infectious Diseases, vol. 52, No. 1, pp. 49-57, Jan. 1, 2011.

Samuel et al., "CMV-reactive T cells can be isolated from G-CSF mobilised peripheral blood Apheresates", Blood, vol. 116, No. 21, Nov. 19, 2010, 1276, 5 pages.

Samuel et al., "Successful isolation and expansion of CMV-reactive T cells from G-CSF mobilized donors that retain a strong cytotoxic effector function", British Journal of Haematology, vol. 160, No. 1, Oct. 9, 2012, pp. 87-100.

Vasileiou et al., "Rapid Generation of Multivirus-Specific T Lymphocytes for the Prevention and Treatment of Respiratory Viral Infections," Blood, vol. 132, No. Suppl. 1, 3332, Nov. 29, 2018 (Nov. 29, 2018), 3 pages.

Vasileiou et al., "Rapid Generation of Multivirus-Specific T Lymphocytes for the Prevention and Treatment of Respiratory Viral Infections," Biology of Blood and Marrow Transplantation, vol. 25, No. 3, 544, Mar. 2019 (Mar. 2019), p. S363.

International Search Report and Written Opinion for International Application No. PCT/US2023/062689 dated May 11, 2023, 23 Pages.

Figure 1   Diagrammatic Representation of A Wilson Wolf Device
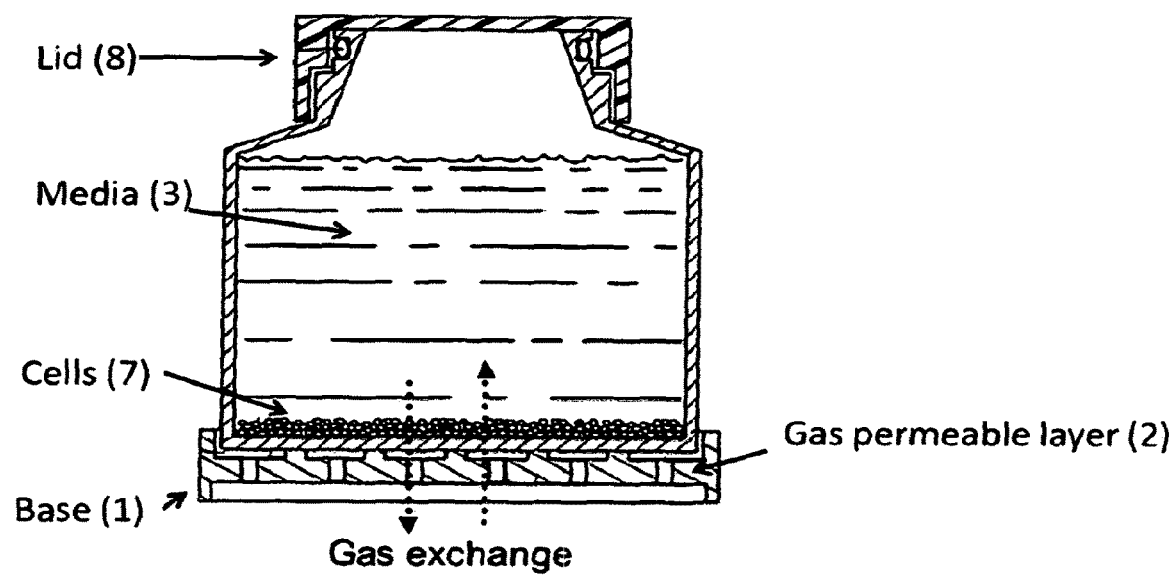

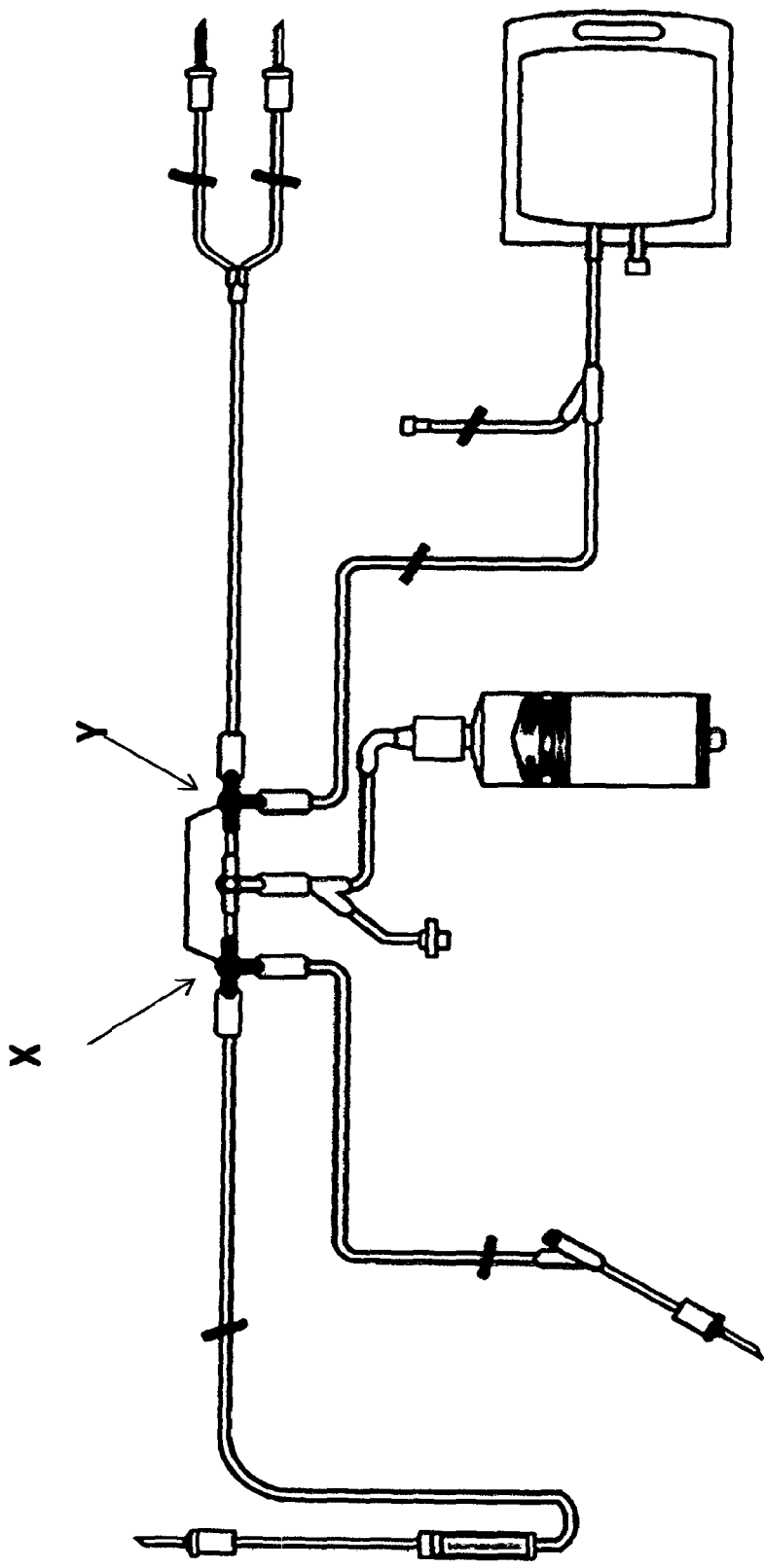
FIGURE 2  Diagrammatic Representation of Apparatus Employed in Example 3

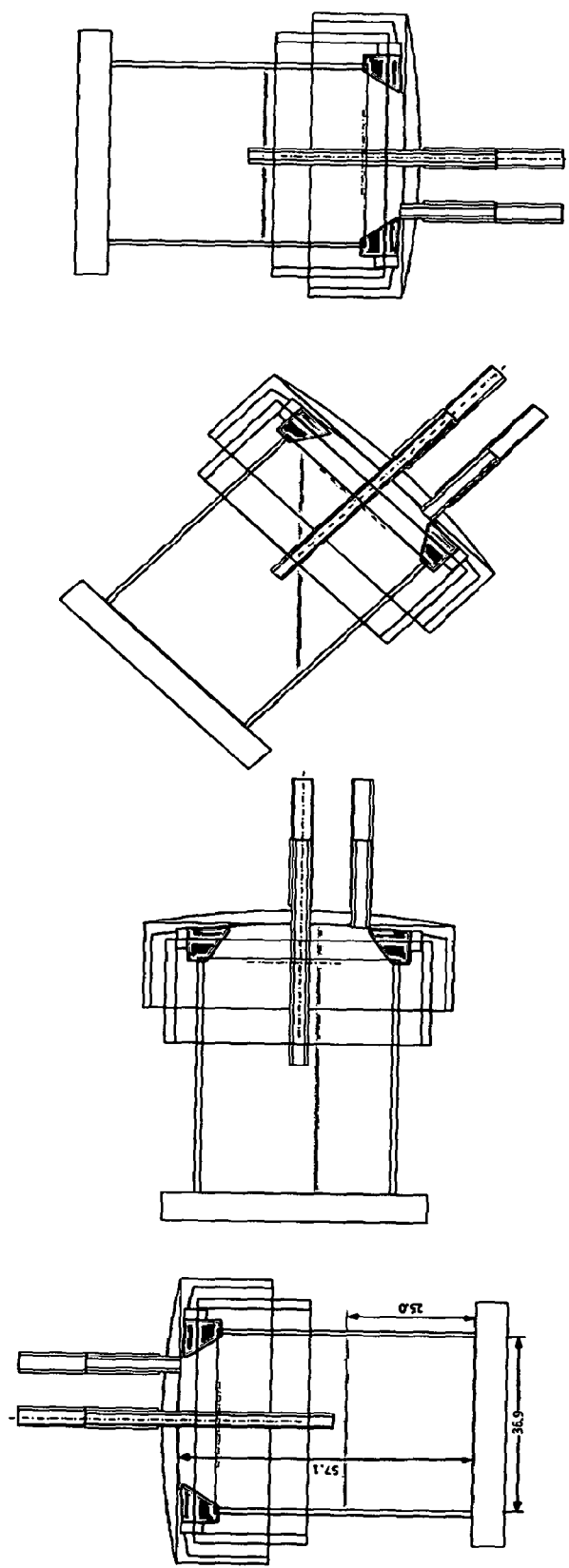

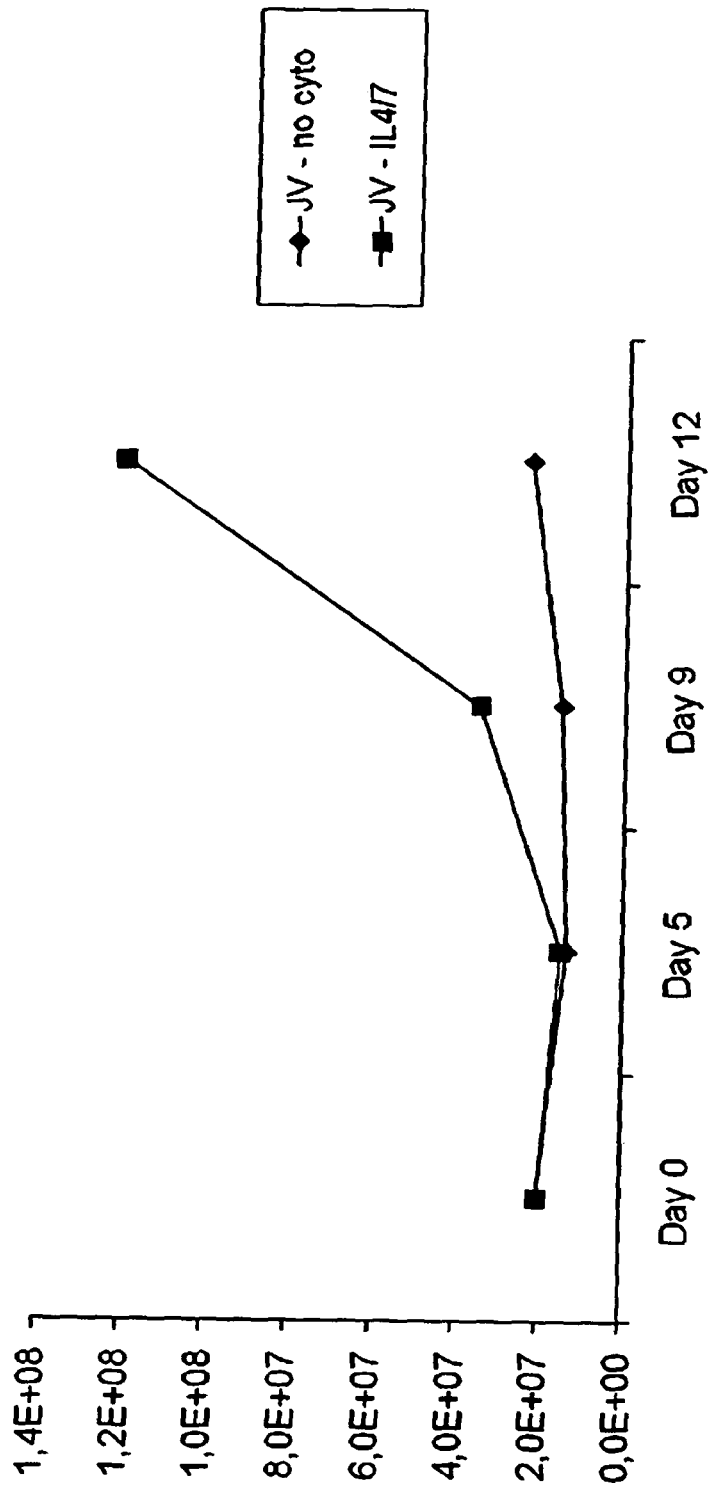
Figure 4A  Expansion of cytolytic T lymphocytes from donor III in the presence of IL4 and IL7 and in the absence of said cytokines

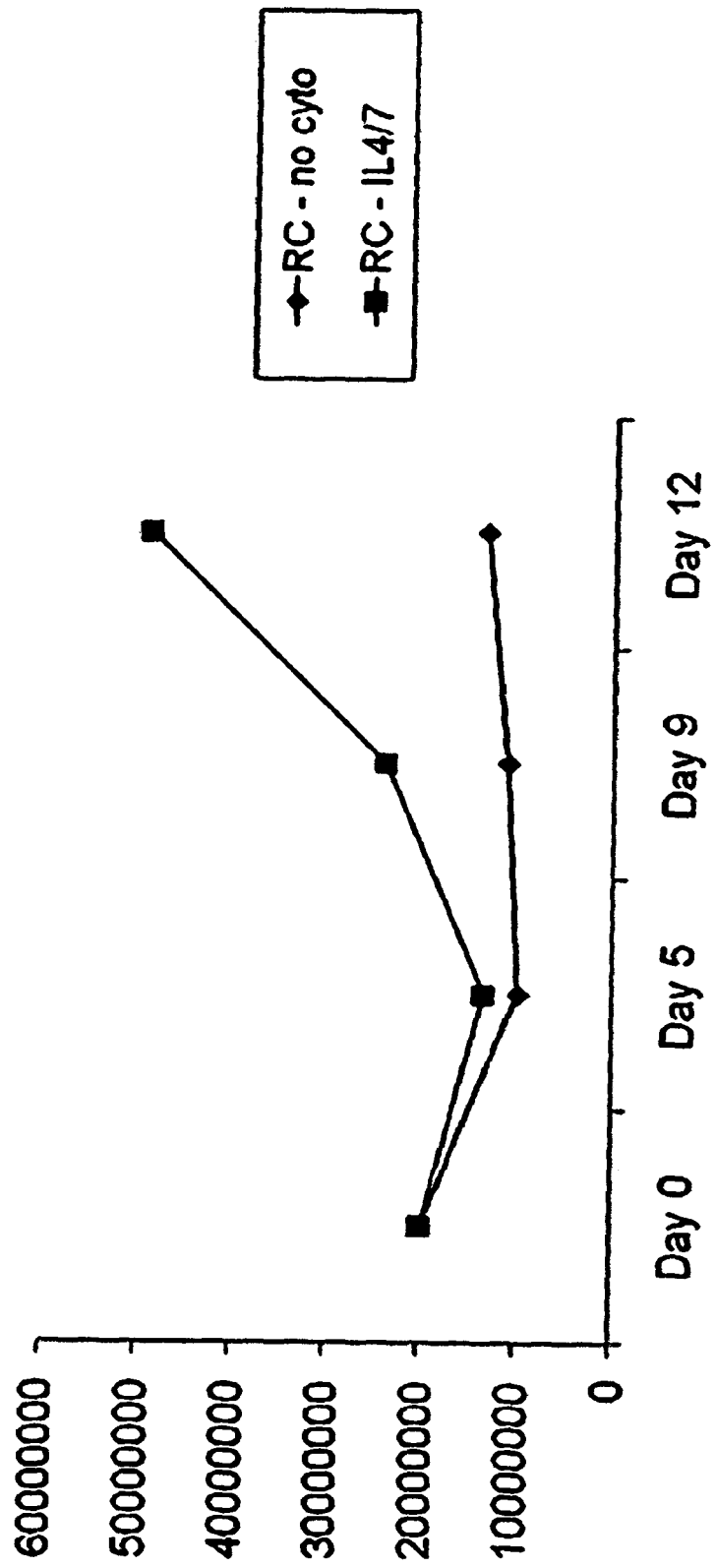
Figure 4B  Expansion of cytolytic T lymphocytes from donor III in the presence of IL4 and IL7 and in the absence of said cytokines

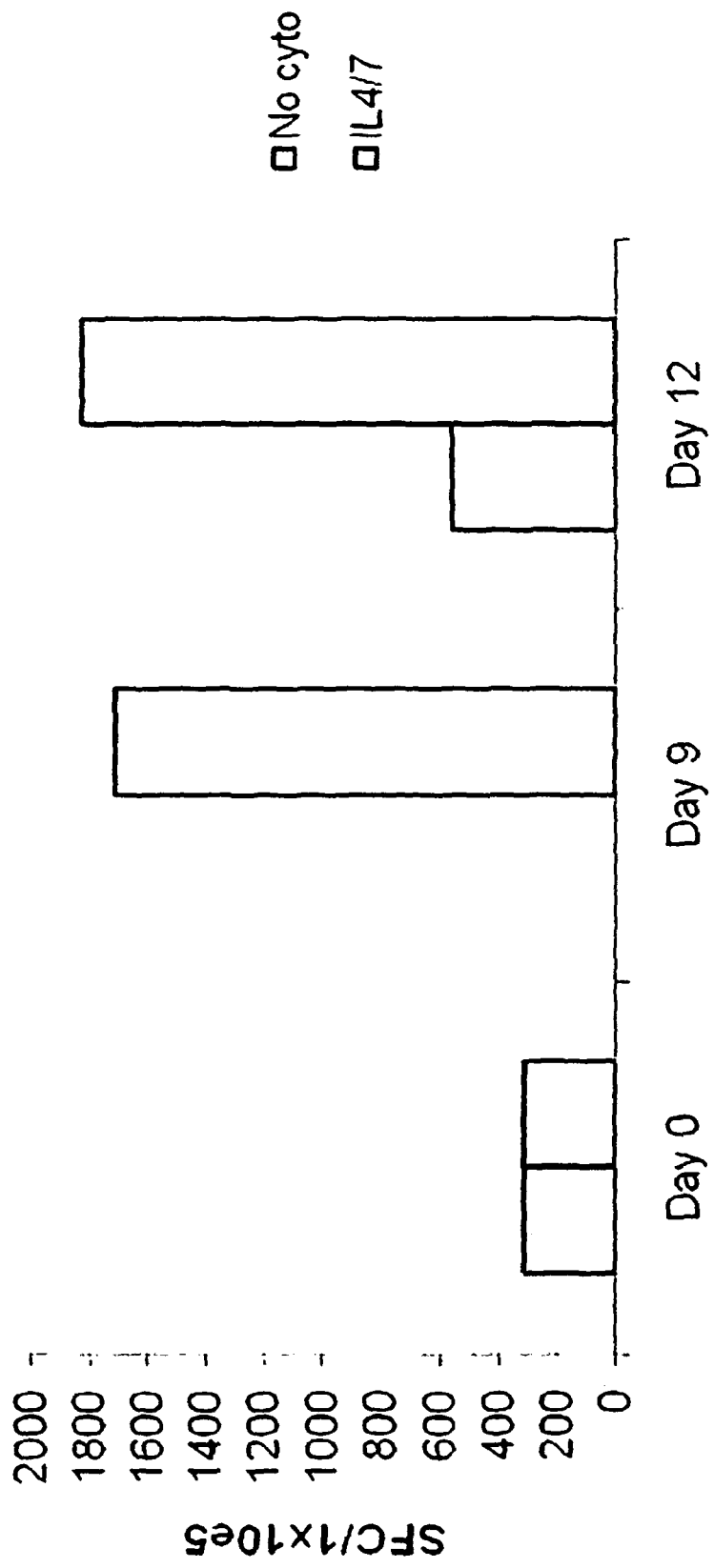
Figure 5A shows the spot forming cells in a cytokine specific assay for expanded cells from donor III which were cultured in the presence of CMV peptide pp65, IL4 and IL7 or in the absence of cytokine

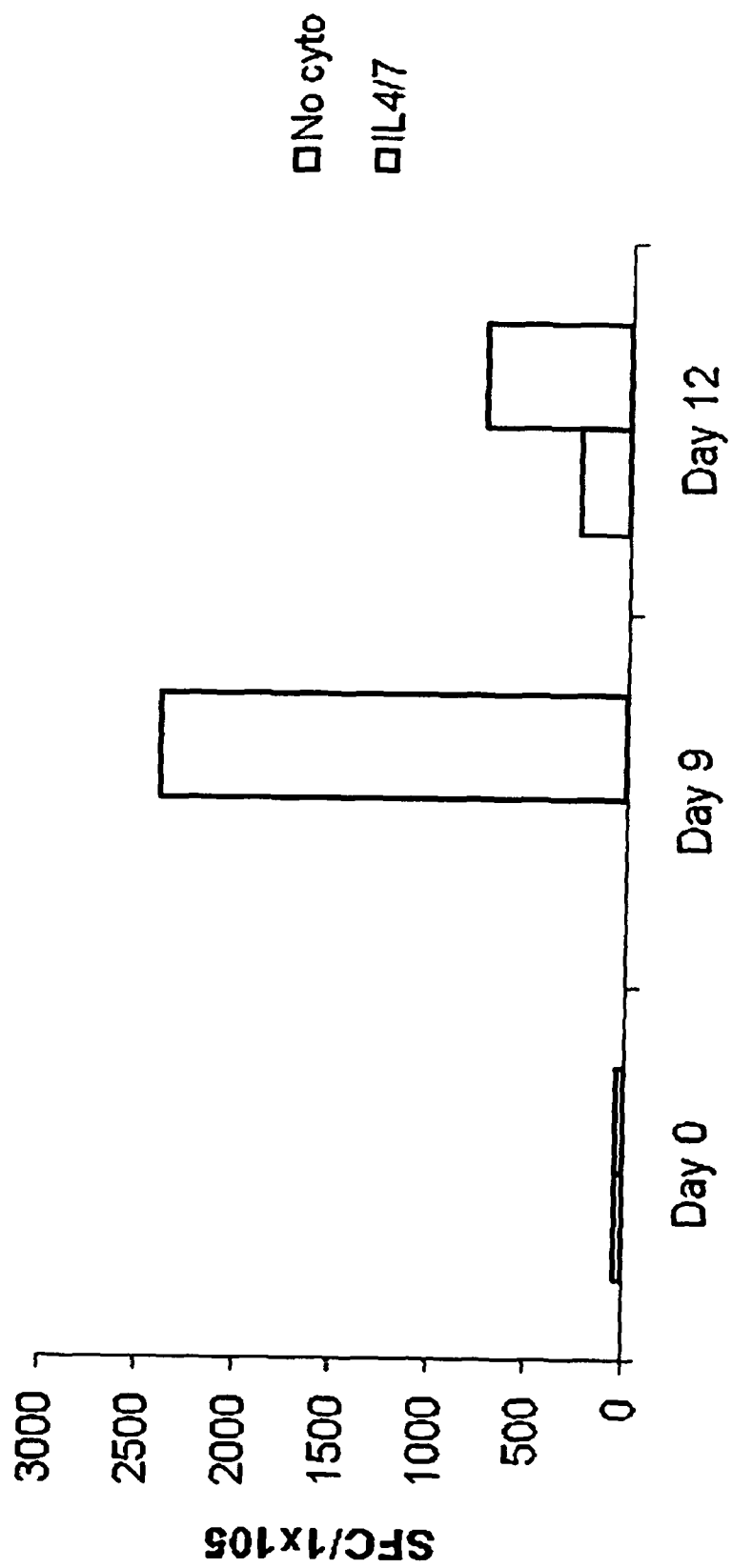
Figure 5B shows the spot forming cells in a cytokine specific assay for expanded cells from donor II which were cultured in the presence of CMV peptide pp65, IL4 and IL7 or in the absence of cytokines

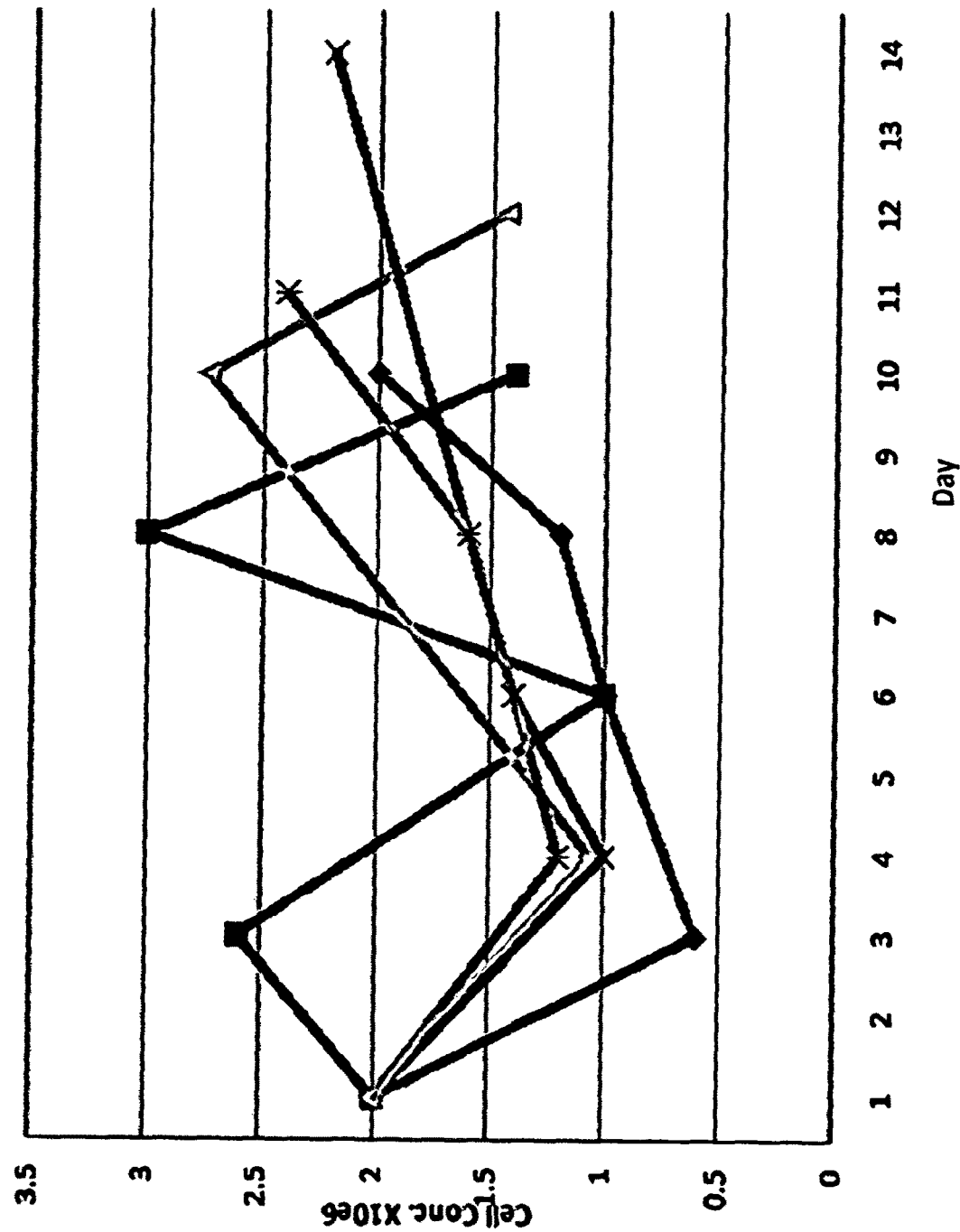
Figure 6A   Shows the Cell Growth Rates for CMV Specific Expanded Populations

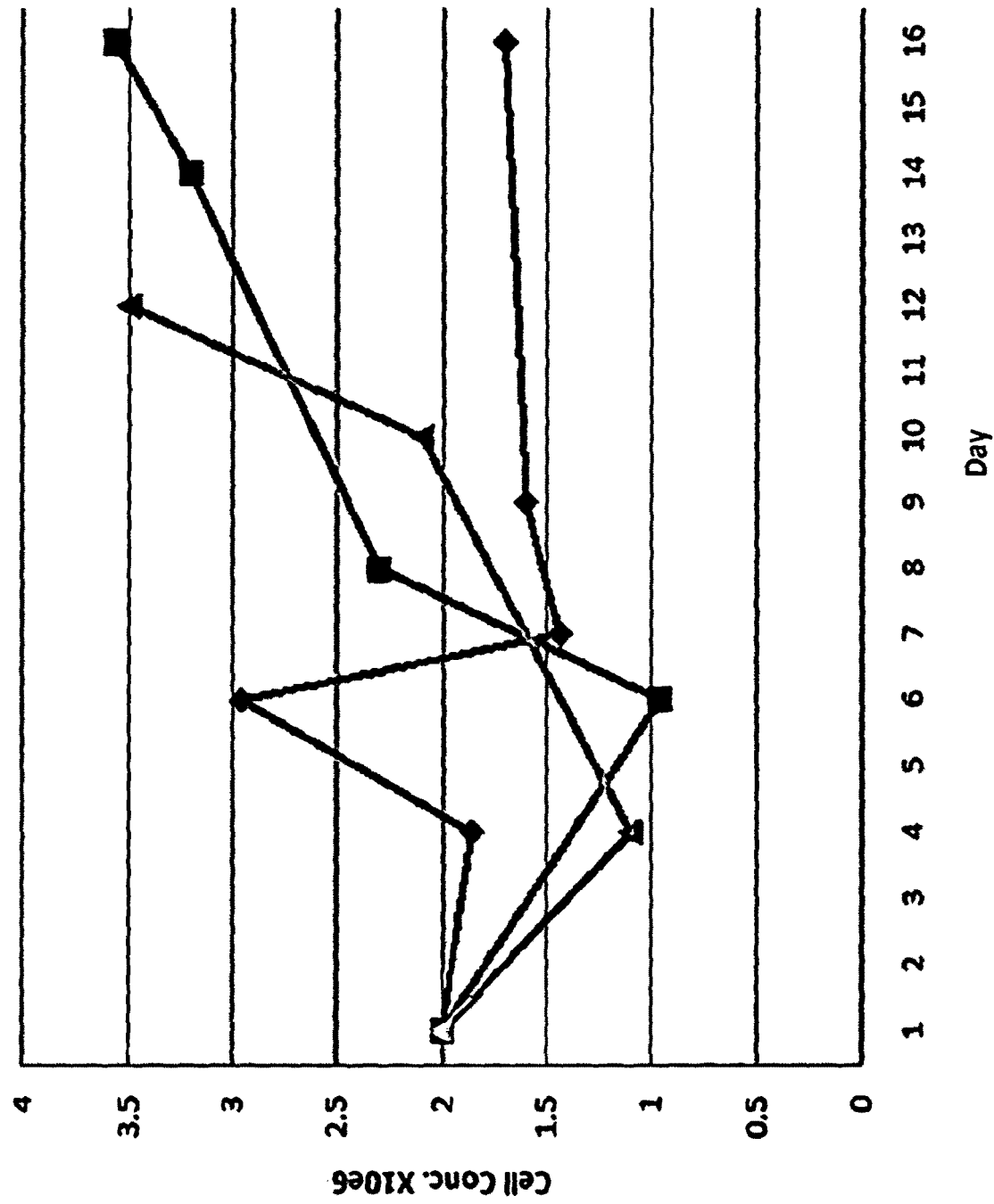

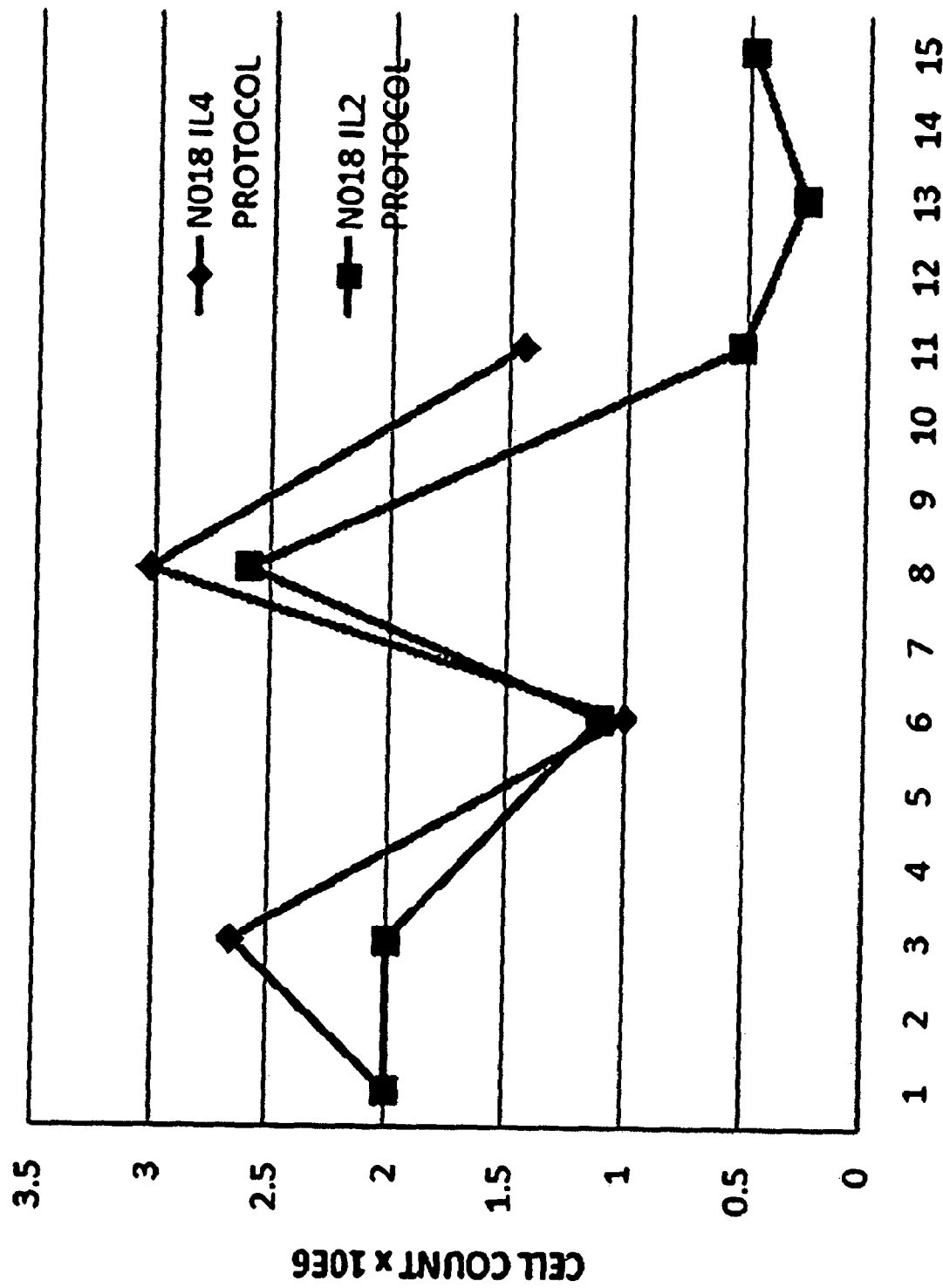
Figure 8  IL4 Expansion Protocol vs IL2 Expansion Protocol

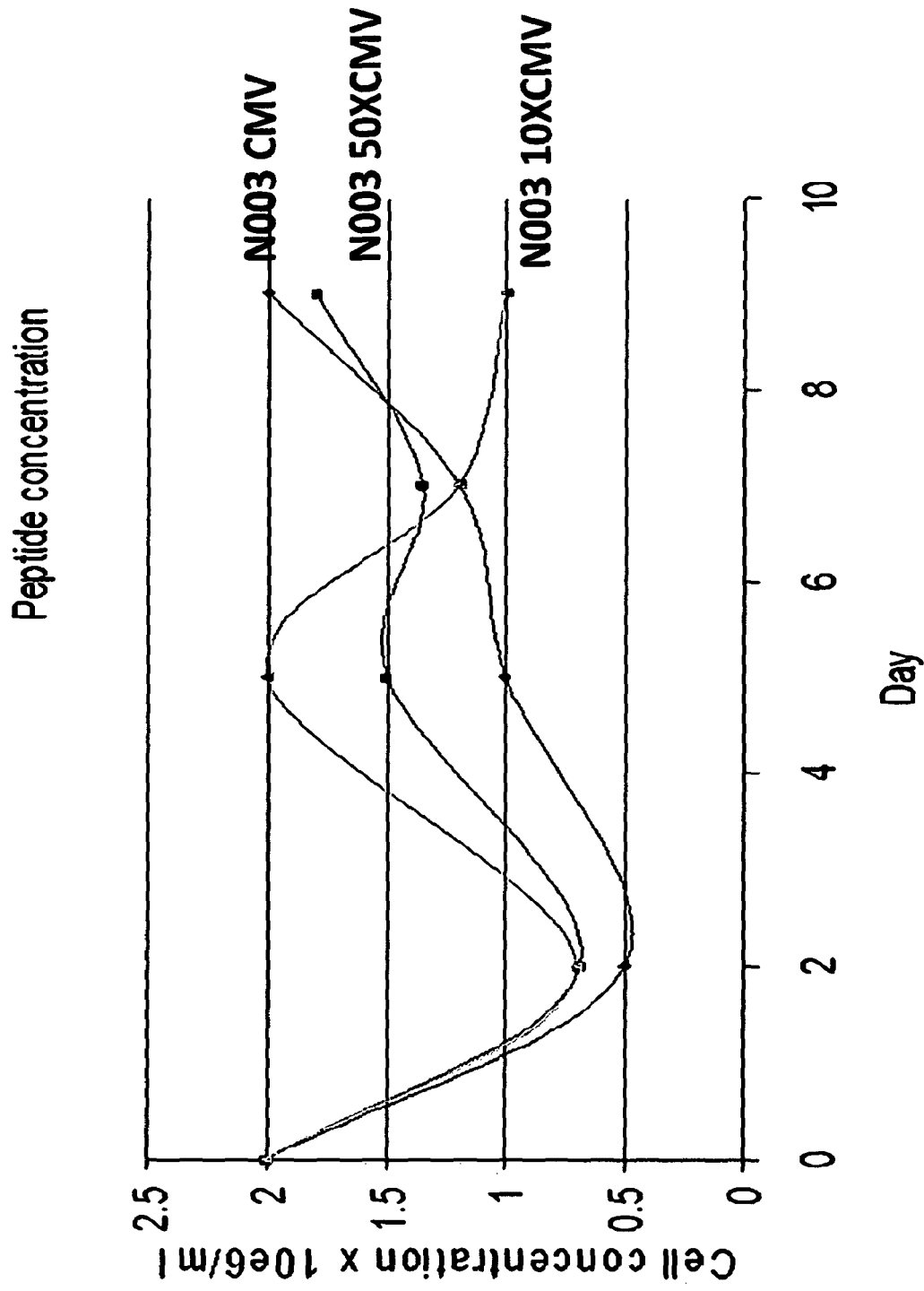
Figure 9  Culture with Peptide Concentrations of 5ng/Ml (CMV), 50ng/mL (10XCMV) or 250ng/Ml (50XCMV)

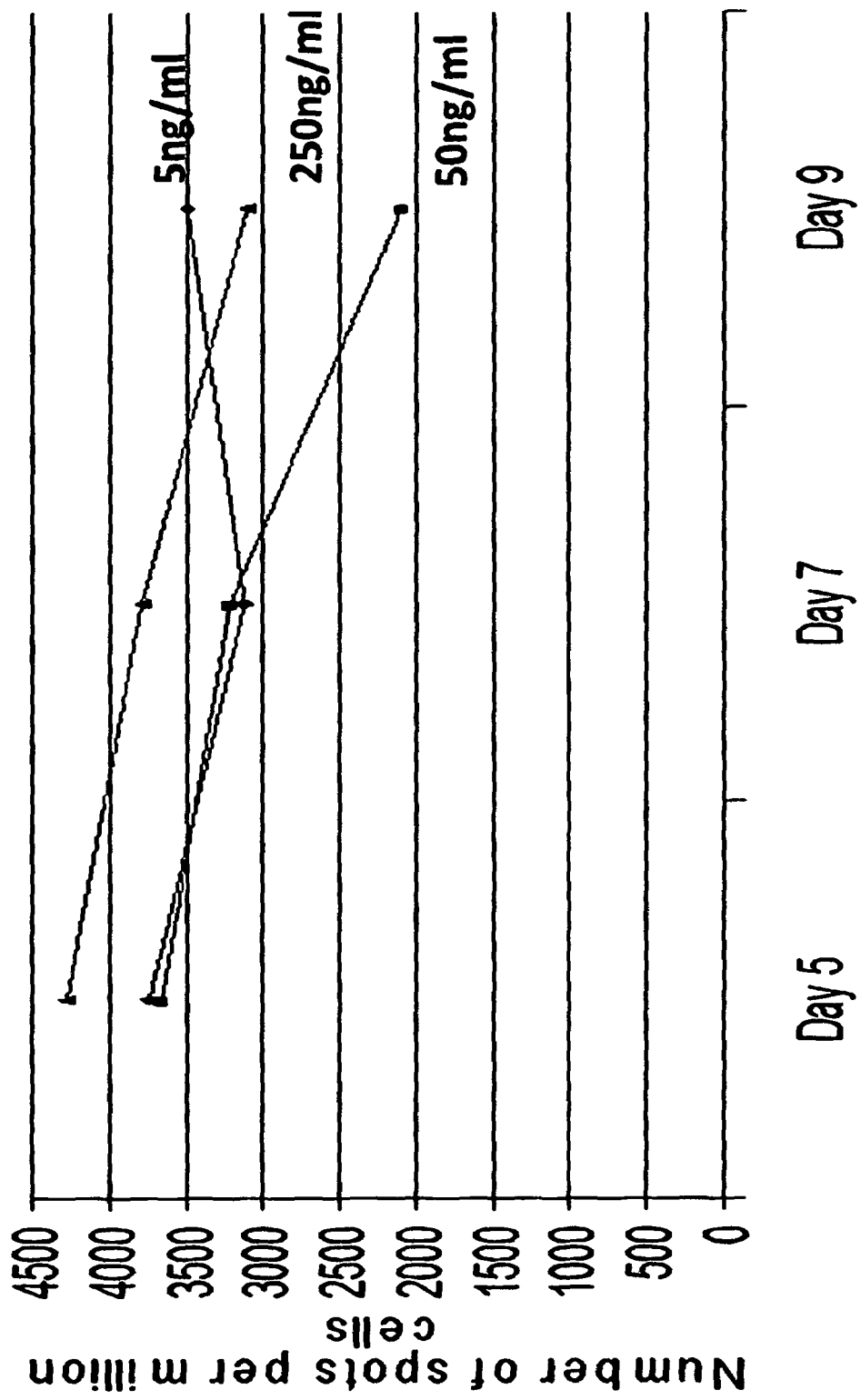
Figure 10  IFNg Productions at different peptide concentrations

PROCESS FOR T CELL EXPANSION

CROSS-REFERENCE TO RELATED APPLICATIONS

The present application is a continuation of U.S. patent application Ser. No. 14/364,621 filed Jun. 11, 2014 (now abandoned), which is filed under 35 U.S.C. § 371 as the U.S. national phase of International Application No. PCT/GB2012/053113, filed Dec. 12, 2012, which claims priority from GB patent application serial number 1121308.9 filed Dec. 12, 2011, which is hereby incorporated by reference in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Jun. 22, 2018, is named 370908-3001US2_SequenceListing.txt and is 87 kilobytes in size.

The present invention relates to a novel process for expanding T cells, in particular antigen specific T cells, such as allogeneic T cells, cell populations therefrom, pharmaceutical compositions comprising the said cell populations and use of the cells and compositions for treatment, particular the treatment or prophylaxis of virus infection, especially in immune compromised patients.

BACKGROUND

Immune compromised patients are susceptible to opportunistic virus infection. This is a huge problem in bone marrow transplant patients because their immune cells are routinely depleted as part of the bone marrow transplant procedure and other times rendered non-functional due to steroid treatment for Graft versus Host Disease (GvHD) which is a common complication of bone marrow transplantation. Latent viruses such as Cytomegalovirus (CMV) and Adenoviruses (ADV) become re-activated and the body is unable to fight the infection. The term bone marrow transplantation as used herein describes all forms of allogeneic haematopoietic stem cell transplantation (allo-HSCT) including procedures involving stem cell donation from related or unrelated donors or from cord blood.

A practice of immune reconstitution has developed and this involves the transplant (adoptive transfer) into the transplant patient of immune cells from a matched HLA donor, usually the same donor who provided the bone marrow. These cells appear to engraft in the patient to provide long-term immunity to pathogens or at least interim assistance in fighting infection until the patient's own immune system is fully reconstituted through the engraftment of the donor's haematopoietic stem cells which will then develop into a diverse array of blood cells and immune cells.

Years of clinical research into the adoptive transfer of donor immune cells to achieve immune reconstitution in a patient following a bone marrow transplant has illustrated the benefits of this approach as well as the challenges of optimising the approach to ensure a consistently efficacious an safe result. In some cases, the number of donor immune cells which are necessary to effect immune reconstitution against a specific pathogen cannot be obtained through simple mechanical selection systems. In such cases, the minimum dosing of the therapeutic immune cells, in particular antigen-specific T cells which demonstrate an adaptive memory immune response against the target pathogen, can be obtained by expanding the desired donor T cell population on an ex vivo basis using a cell culture system. Prior art indicates that the process of expansion of the cells from the donor sample generally takes about 21 days and the focus has been to expand the specific cells in order to obtain the highest possible number (yield) of the relevant cell populations as well as the highest possible purity of the relevant cell populations, so for example to obtain a population which is as close to 100 percent pure for the target cells. This obviously takes long periods of expansion and repeated antigen stimulation to ensure the cells keep expanding, through cell culture. Whilst not wishing to be bound by theory, it is likely that the thinking behind this was two-fold, firstly the larger the number of relevant cells the more effective the treatment will be and secondly by ensuring a highly purified target population toxicities and unwanted effects from contaminating cell products are avoided. Exogenous IL-2 has traditionally been employed in the culture since this cytokine has been characterised as a T cell growth factor. Generally, the source of exogenous of IL-2 is required once or twice a week during the expansion process.

The inventors have established a rapid process for the expansion of antigen-specific T cells that provides one or more of the following advantages in that it is:

1) efficient, robust, viable, and/or economically cost-effective for producing the cell product
2) provides a therapeutic dose (yield) of the antigen-specific T cells within a minimum period of culture time
3) minimises contamination from other cells which may cause unwanted toxicities in the patient, in particular Graft vs Host Disease in a clinically relevant context
4) ensures compliance with GMP production requirements through the development of new and inventive technological adaptions to existing technology which does not conform to GMP requirements
5) provides the option to omit the addition of exogenous IL-2
6) allows expansion from a donor blood sample which is considered mobilised as defined by the donor having received G-CSF prior to making the bone marrow (haematopoietic stem cell) donation
7) provides a product with equivalent or improved characteristics over the prior art by optimising a desirable balance be reached between the adequate expansion of antigen-specific T cell populations and the presence of potentially harmful contaminating cell populations, and
8) allows expansion from a small donor sample in the range 50-100 mls.

This will be explained in more detail below.

In addition to these practical improvements the present inventors have reason to believe that the prior art methods of culturing cells for prolonged periods particularly in the presence of IL-2 may result in T cell populations which demonstrate a certain degree of exhaustion or anergy. That is to say there may be a large number of the desired cells present in the population but many of these may not be functioning or may be functioning sub-optimally, for example hyporesponsive in one more or more functional aspects.

SUMMARY OF THE INVENTION

The present inventors have devised an in vitro expansion process for rapid expansion of antigen specific T cells, such as allogeneic antigen specific T cells comprising the steps culturing, in a vessel comprising a gas permeable culture surface, a population of PBMCs (in particular allogeneic PBMCs) in the presence of a peptide or peptide mix relevant to a target antigen(s), and in the presence of at least one exogenous cytokine characterised in that the at least one cytokine is other than exogenous IL-2. There is also provided an in vitro expansion process for rapid expansion of allogeneic antigen-specific T cells comprising the steps of culturing, in a vessel comprising a gas permeable culture surface, a population of allogeneic PBMCs in the presence of a peptide or peptide mix relevant to a target antigen(s), in the presence of at least one exogenous cytokine characterised in that the expansion to provide the desired population of antigen specific T cells is performed for 14 days or less. The process of the present disclosure has many advantages in that it reduces the time and resources required to expand the antigen-specific T cells, it is robust and minimises the risk of contamination and these aspects are of huge practical significance because the process can be made GMP compliant and will make the therapy accessible to a larger number of patients in need thereof.

BRIEF DESCRIPTION OF THE DRAWINGS

FIG. 1 is a diagrammatic representation of the GRex system available from Wilson Wolf FIG. 2 is a diagrammatic representation of apparatus employed in FIG. 3

FIG. 3 is a diagrammatic representation of a modified GRex system suitable for use as a closed system FIGS. 4A & B is a graph of two samples showing that 50-100 ml of blood draw is sufficient to generate a sufficient dose of adenovirus specific T cells grown using IL-4/7 but not without.

FIGS. 5A & B shows the spot forming cells in a cytokine specific assay for expanded cells from donor II and III which were cultured in the presence of CMV peptide pp65, IL4 and IL7 or in the absence of cytokines FIGS. 6A & 6B Shows the cell growth rates for CMV and adeno specific expanded populations FIG. 7 Shows adenovirus and CMV specific cytokine production using Elispot FIG. 8 IL4 expansion protocol vs IL2 expansion protocol FIG. 9 Culture with peptide concentrations of 5 ng/ml (CMV), 50 ng/ml (10XCMV) or 250 ng/ml (50XCMV)

FIG. 10 Shows IFNg productions at different peptide concentrations

DETAILED DESCRIPTION OF THE INVENTION

Figure 7:
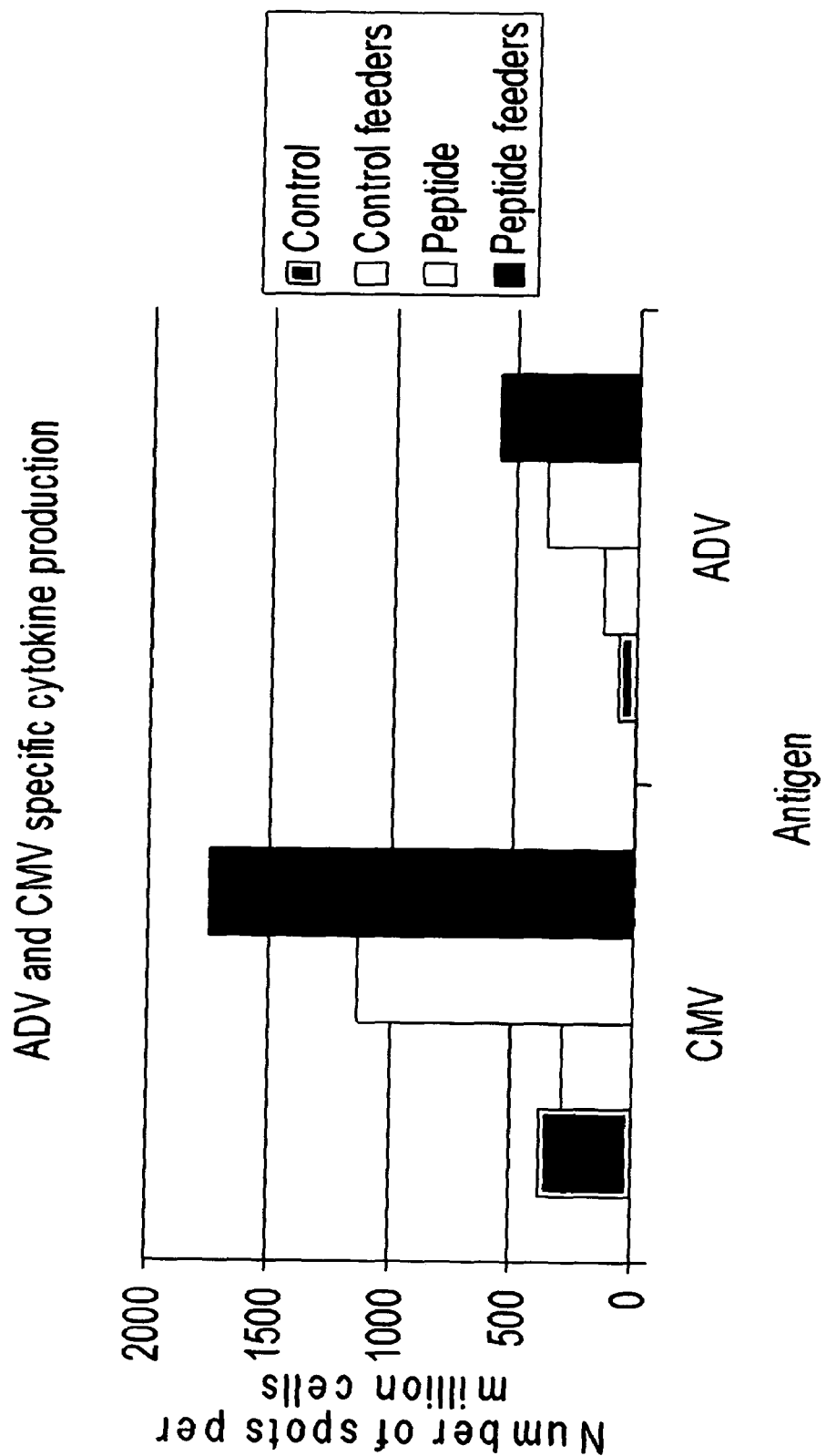

Rapid expansion as employed herein refers to a process in a therapeutic product is obtained within less than 18 days, such as 7-10 days.

The antigen specific T cell population obtained from the process is at least equivalent to the product obtained in the prior art methods but may in a number of respects may have improved properties, for example they may exhibit less or zero anergy or exhaustion in comparison to cells prepared by prior art processes.

The activation of T cells is tightly controlled by many positive and negative regulatory processes. This allows the body to provide immunity to pathogens whilst minimising autoimmunity. Activation of T cells occurs when specific molecules on the surface of professional antigen presenting cells such as dendritic cells bind the T cell receptor and also provide a co-stimulatory factor.

It is documented that anergy or hyporesponsiveness can occur, for example when antigen on antigen presenting cells engages the T cell receptor in the absence of a co-stimulatory signal. This hyporesponsiveness may be manifest by reduced levels of cytokine secretion, for example lower levels of interferon-gamma secretion and/or lower levels of IL-13 secretion.

The lack of anergy, for example may be illustrated in that cells prepared by the present process on average (mean) secrete more interferon gamma than cells prepared by the prior art process, when the secretion of the population as whole is measured and then divided by the number of cells in the relevant population to provide the mean.

In vitro at least certain types of anergy are reversible, for example by the addition of IL-2. In vitro it is not known how anergic cells respond in the case of adoptive transfer of cells to a patient whether anergic cells can be revived to perform their natural functions.

Whilst not wishing to be bound by theory when preparing therapeutic antigen specific T cell populations, the absolute number of cells for dosing may not be the most definitive factor in providing an effective product. Rather the functionality of the cells administered may be more relevant. That is to say administering cells wherein the number of hyporesponsive cells are minimised.

The present process optimises the amount of functional cells in that the culturing of the cells is for a relatively short period, generally 14 days or less. Thus the cells are not artificially activated to the point where they start to become unviable or hyporesponsive.

In one embodiment the cells are expanded in the absence of exogenous IL-2 and instead in the presence of only endogenous IL-2. Although IL-2 is known to be a T cell stimulator, the empirical observation when employed in the present method is that it seems to drive proliferation too fast and may result in a some disadvantages.

In one embodiment a small amount of exogenous IL-2 is employed, e.g. 10 units or less per ml.

An exogenous factor is one that is not present in the culture of PBMCs without addition or where the naturally occurring amounts present in the cell culture are augmented by addition of exogenous amounts of the factor.

Expanding the cells for a reduced period of time and/or without the addition of exogenous IL-2 means that the artificial conditions (for example sustained periods of expansion and/or high levels of stimulation) of the prior art process are avoided and thus anergy/exhaustion resulting from the same may be minimised.

The current process balances generating a sufficient population of antigen-specific T cells whilst minimising but not necessarily eliminating the non-target populations of cells.

Generally the expanded cell population obtained from the current process does not contain more than 80% of the target antigen specific T cell population and this is a marked departure from the established wisdom of the field.

Whilst not wishing to be bound by theory it is believed that the population of antigen-specific T cells generated is sufficient to continue expanding in vivo. This may be in part because the cells produced are not anergic/exhausted.

The cells administered to the patient by infusion are intended to continue expanding in vivo. It is believed that antigen-specific T cells generated by the process described herein are suitable for the intended therapeutic purpose.

Other cell populations in the expanded product according to the present disclosure are at least not harmful and may in fact be beneficial, for example because the overall population of cells infused into the patient may be more representative of the natural environment in vivo and thus more compatible therewith.

Anergy in the context of the present specification is intended to refer to a T cells' functional unresponsiveness in one or more ways in the presence of antigen, for example failure to undergo antigen-specific expansion and/or failure to secrete cytokines such as TNF-α or interferon-gamma. Populations, as employed herein comprise a number of individual cells. The relevant population will not be considered anergic to the extent that at least 80% of the population are not anergic in any respect, for example 85, 90, 95 or 100% of the relevant cells are not anergic. Of course anergy is not a binary analysis but should be viewed within a range of the quality of T cell responses as measured by one or more functional assays.

As described above anergy in the context of the present specifications is intended to be a generic term that refers to reduced cell function in one or more relevant ways. The term includes cell exhaustion, for example where the cells are no longer able to divide. The cell is then referred to as senescent. Cells stop dividing because the telomeres, protective lengths of DNA on the end of a chromosome required for replication, shorten with each cell division, eventually being reduced to a point which through biological mechanisms limits further cell division.

In one embodiment the anergy is hyporesponsiveness.

In one embodiment anergy may be reversible in vitro by addition of IL-2. This feature may be employed as an assay for certain types of anergy.

There are certain cell surface markers that are exhibited by anergic cells, for example PD-1 (programmed cell death protein 1 Uniprot 015116) or PD-1 ligand. In one embodiment 10% or less such as 9, 8, 7, 6, 5, 4, 3, 2 or 1% of the expanded antigen specific T cell population express PD-1 on their surface. Blimp-1 may be another cell surface marker of anergy.

In another embodiment, PD-1 is not permanently expressed on the T cells and expression is reversible Markers for cells that may apoptotic may include down regulation of one or more of CD4, CD8, HSA, CD45RB or a combination of the same and/or upregulation of one or more CD3/TCR, CD69 and CD25). "T cell" is a term commonly employed in the art and intended to include all CD3+ cells including thymocytes, immature T lymphocytes, mature T lymphocytes, resting T lymphocytes or activated T lymphocytes. A T cell can be a T helper (Th) cell, for example a T helper 1 (Th1) or a T helper 2 (Th2) cell, although other grouping of T cell populations are being discovered based on intensive research. The T cell can be a CD4+ T cell, CD8+ T cell, CD4+CD8+ T cell, CD4-CD8- T cell or any other subset of T cells.

The distinguishing feature of the T cells which are the product of the current process is that the T cell has a CD3+ associated T cell receptor (TCR) which provides the antigen-specificity which is a key aspect of the efficacy and safety of the cells for the intended purpose of reconstituting immunity on a pathogen-specific basis in the patient. The target population of cells can be selected employing this marker.

In one embodiment the target antigen specific T cell population is biased towards a CD4+ population. That is to say the antigen specific response is focused in the CD4+ cells. In one embodiment the populations contains more CD4+ cells than, for example CD8+ cells.

Antigen specific T cell population as employed herein refers to T cells which are specific for the antigen which they target. Specific refers to the ability of the relevant T cells to discriminate against antigen targets and other entities to which they are not specific.

The vessel comprising a gas permeable culture surface is a significant part of the process because it allows efficient expansion in the presence of all the required nutrients (T cell expansion media), without the need to change the media or provide additional factors. Thus the vessel can support the volume of media required whilst allowing the gas exchange with the environment to ensure oxygen levels are sufficient for cell growth.

The process of the present disclosure suitably is performed in a vessel comprising a gas-permeable culture surface. Vessel as employed herein is intended to refer to any type of container suitable for retaining the cells, media etc, for example a bag, such as an infusion type bag (provided with a gas permeable portion) or a rigid vessel, such as the GRex™ system see FIG. 1. The gas permeable culture surface facilitates rapid expansion of cells and minimizes the number of media changes required. This allows the manufacture of the expanded cells in a so-called one touch process, wherein all the components for the process are inserted at the one time and can be left without interference until the expansion is complete. The only step that remains is the harvest the expanded cells. WO 2005/035728 incorporated herein by reference describes how to prepare a gas permeable vessel (i.e. a vessel comprising a gas permeable culture surface). In one embodiment silicone gas permeable material is employed.

In one embodiment the system employed is a GRex™ system from Wilson Wolf. The system allows the cells to be expanded in 20 days or less, for example 14, 13, 12, 11, 10 days or less, such as 14 days or 10 days.

Rapid expansion as employed herein is expansion for about 18 days or less, such as 17, 16, 15, 14, 13, 12, 11, 10, 9, 8 or 7, such as 14, 13, 12, 11, 10, 9, 8 or 7 days. 9 or 10 days seems optimal in most cases. This rapid expansion allows all the nutrients and media for the culture to be added, for example at the beginning of the process and the cells can grow and divide without any further intervention. This is advantageous because it minimizes contamination and potential for errors and also minimizes human resource required to expand the cells.

The system can also be adapted to render it a closed systems to allow the product to be manufactured aseptically, for example a described in U.S. provisional application Ser. No. 61/550,246, incorporated herein by reference. In one embodiment the system is a modified system as described in PCT/GB2012/052587 incorporated herein by reference.

Thus in one embodiment the system is a closed system suitable for the aseptic culturing therapeutic cells comprising:
(i) a vessel comprising:
  a gas permeable portion suitable for supporting cell growth and allowing delivery of gases to the cells during culturing, and
  at least one wall adjoined to a base,
  wherein said vessel defines an internal volume and said vessel is adapted to contain a requisite volume of medium to support a cell culture,
(ii) a vent comprising a conduit defining an interior orifice and an exterior orifice distal therefrom in fluid communication with each other, wherein the conduit extends from the exterior of the closed systems through a structural feature of the system and extends into the internal volume of the vessel and terminates therein with the interior orifice, wherein the interior orifice is arranged such that during filling and emptying of liquid medium it is not susceptible to blockage by liquid, wherein the exterior orifice is adapted to connect to an aseptic filter thereby allowing passage of gases through the filter into the vessel or out of the vessel, as required to achieve the entry and exit of fluids and cells into the vessel, (iii) a port or ports adapted to allow introduction of fluids and cells aseptically into the vessel, a port or ports adapted to allow fluids to exit the system without exposing the system to the external environment and adapted such that cells grown therein may exit the system under gravity when the system is orientated to put the cells in fluid communication with the exit port and the latter is opened.

A system of this arrangement is show in FIG. 3, by way of example.

In one embodiment the whole expansion process is performed aseptically in a closed system.

In one embodiment the system is seeded with about 0.5 to 2 million cells per cm$^2$ of surface area. In a GRex-10 with a surface area of 10 cm$^2$, a minimum of 5 million and up to 20 million cells would be seeded.

In one embodiment the system is seeded with about 20 million effector cells which equated to about 10 cm$^2$ of cells.

The present invention relates to ex vivo processing of cells and the T cell products obtained therefrom. Usually the present invention does not include the step of obtaining the sample from the patient.

The step of obtaining a suitable sample from the donor is a routine technique, which involves taking a blood sample. This process presents little risk to donors and does not need to be performed by a doctor but can be performed by appropriately trained support staff. In one embodiment the sample derived from the patient is approximately 200 ml of blood, or less, for example 50-100 ml.

Surprisingly sufficient numbers of antigen specific T cells can be generated using this small amount of blood.

Surprisingly the inventors have found that PBMCs from a mobilised blood sample may be employed in the expansion process. A mobilised sample is one where the donor has received G-CSF (granulocyte colony-stimulatory factor) and other factors which stimulate bone marrow to produce stem cells and then release them into the blood. Blood samples taken at this time have not been employed for later use in immune reconstitution therapy of the patient, simply because it was considered not suitable. Nawa et al in Bone Marrow Transplantation (2000) 25, 1035-1040, for example suggest that G-CSF results in reduced ability to secrete interferon gamma, IL-4 and also reduces proliferative responses. Shantaram et al in Blood, 15 Sep. 2001, Vol 98, number 6 also suggest that there is decreased immune functions of blood cells after mobilization with G-CSF. Other research has suggested that G-CSF may skew the T cell population to the Th2 group, which may be less effective in controlling an intracellular viral infection.

However, it is inconvenient to require donors to return to hospital after haematopoietic stem cell donation to obtain further biological samples. In contrast it is very convenient to take a sample of blood for expansion to produce an immune reconstitution product at the time the as the stem cell sample for transplantation is taken from the donor.

Thus employing mobilised blood for expansion provides a practical advantage to health care workers and donors.

Mobilised blood as employed herein refers to a blood sample from a donor who has been mobilised by treatment with agent such as G-CSF. The process of mobilisation increases the number of stems cells in the peripheral blood.

Mobilised apheresis as employed herein refers to a sample from a donor who has been mobilised by treatment with agent such as G-CSF. The process of mobilisation increases the number of stems cells in the peripheral blood.

Typically the PBMCs for T cell expansion are obtained from the blood or apheresis product by Ficoll density gradient separation known to those skilled in the art.

As is known to the skilled person expansion of T cells is generally performed in a suitable T cell expansion media. T cell expansion media generally comprises serum, media and any cytokines employed in the expansion step, for example as specified in the consistory clause or claims, as appropriate.

In one embodiment the media is Advanced RPMI media or RPMI media 1640, available from Life Technologies. Advance RPMI media contains animal derived products and is usually employed with about 2% human serum. In contrast RPMI media 1640 does not contain animal derived products and is usually employed with 10% human serum. The RPMI media 1640 is generally more convenient for use in the present method.

Alternative serum free media is available from AQIX RS-I for lymphocyte culture.

In one embodiment the medium comprises 45% advanced RPMI, 45% EHAA, 10% FCs and 200 mM L-glutamine.

In one embodiment the cell expansion medium comprises 10% Human AB serum, 200 mM L-glutamine, 45% Earle's Ham's amino acids (EHAA or Click's medium) and 45% advanced RPMI or RPMI-1640.

In one embodiment the cytokines employed are discussed below.

In one embodiment the T cell expansion medium employed is not changed or supplemented during the expansion process.

Cell expansion as employed herein refers to increasing the number of the target cells in a population of cells as a result of cell division.

T cell expansion may be evaluated by counting viable CD3+ cells (i.e. the target population of cells is CD3+).

Viable cells can be tested by cell staining with Trypan blue (and light microscopy) or 7-aminoactinomycin D, vital dye emitting at 670 nm (or ViaProbe a commercial ready-to-use solution of 7AAD) and flow cytometry, employing a technique known to those skilled in the art. Where the stain penetrates into the cells the cells are considered not viable. Cells which do not take up dye are considered viable. An exemplary method may employ about 5 μL of 7AAD and about 5 μL of Annexin-V (a phospholipid-binding protein which binds to external phospholipid phosphatidylserine exposed during apotosis) per approximate 100 μL of cells suspension. This mixture may be incubated at ambient temperature for about 15 minutes the absence of light. The analysis may then be performed employing flow cytometry. See for example MG Wing, AMP Montgomery, S. Songsivilai and JV Watson. An Improved Method for the Detection of Cell Surface Antigens in Samples of Low Viability using Flow Cytometry. J Immunol Methods 126: 21-27 1990.

An alternative stain is TO-PRO-3 which is a carbocyanine monomer nucleic acid stain with far-red fluorescence similar to Alexa Fluor 647 or Cy 5 dyes. It is useful as a nuclear counterstain and dead cell indicator, and is among the highest-sensitivity probes for nucleic acid detection.

Viruses against which antigen specific T cell populations can be expanded include cytomegalovirus, adenovirus, varicella zoster virus, BK virus, human papillomavirus, hepatitis B virus, hepatitis C virus, Epstein-Barr virus, Kaposi's sarcoma-associated herpes virus and human T-lymphotropic virus, such as cytomegalovirus or adenovirus.

Antigen employed in the process includes full-length polypeptides, fragments of polypeptides or peptides.

Peptide as employed herein is intended to refer to short polymers of amino acids linked by peptide bonds, wherein the peptides contain at least 2 but generally not more than 50 amino acids.

The peptides employed are sufficiently long to present one or more linear epitopes, for example are on average 7, 8, 9, 10, 11, 12, 13, 14, 15, 16, 17, 18, 19 or 20 amino acids long.

In one embodiment some of the peptides of the mixture overlap (in relation to the sequence of a single antigen), that is to say that they are from a single antigen and are arranged such that portions of the fragments and certain sequence of amino acids from the parent sequence occur in more than one peptide fragment of the mix.

In one embodiment 1, 2, 3, 4, 5, 6, 7, 8, 9, 10, 11, 12, 13, 14 or 15 amino acids overlap in each peptide.

In one embodiment the peptide libraries for each protein are 15 amino acids long and overlap by 11 amino acids so that all potential epitopes can be presented from a protein. The peptides can be longer, for example 20 amino acids overlapping by 15 or 30 amino acids overlapping by 25.

In one embodiment the target virus is CMV and, for example the antigen employed to the target the virus is pp65. The sequence for human cytomegalovirus (strain AD169) is in the UniProt database under number P06725. The recombinant protein can be purchased from Miltenyi Biotech. The latter company also provide PepTivator® CMV pp65 which is a peptide pool that consists mainly of 15-mer peptides with 11-amino acid (aa) overlap, covering the complete sequence of the pp65 protein of human cytomegalovirus. further target antigens for CMV include pp50 and IE-1 (also known as UL123). Target EBV antigens include EBNA1, LMP1, LM P2 and BARF1. Examples of suitable peptides sequences for these antigens include those in sequence ID NO: 1 to 335 disclosed in the associated sequence listing. Included with the present application is sequence listing comprising 340 sequences of antigens. For adenovirus target antigens include the hexon and penton.

For BK virus target antigens include large T antigen and small t-antigen.

In one embodiment the peptide mix comprises or consists of 2-1000 peptides, more specifically 2-500, for example 2-400, 2-300, 2-200 or 2-100 such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 peptides.

In one embodiment 5 to 500 ng of peptide or each peptide library are employed per ml of culture, such as 5, 50, 100, 150, 200, 250, 300, 350, 400 or 450 ng/ml, in particular 5 ng/ml. Alternatively 1, 2, 3 or 4 ng/ml of peptide may be employed.

Advantageously, peptides employed at a concentration of about 5 ng/ml (such as 4, 5, 6, 7, 8, 9 or 10 ng/ml) may result in an expanded antigen specific T cell population that at day 9 or day 10 secrete interferon gamma at levels equivalent or higher to cells expanded employing higher concentrations of peptides.

In one embodiment the peptides employed are GMP grade. That is to say they are manufactured using good manufacturing practice, which means they are suitable for use for the preparation of a therapeutic product.

Cytokines that may be employed in the process of the current disclosure include IL-1, IL-2, IL-4, IL-6 IL-7, IL-12 and IL-15.

A large amount of, as yet non-definitive, literature underlines how IL-2, IL-7 and IL-15 play non-redundant roles in shaping the representation of memory cells. IL-2 controls T-cell clonal expansion and contraction, and promotes lymphocyte differentiation. IL-2 and IL-15 can also support memory cell division and have been used in combination with antigen-driven stimulation, for the expansion of CTL. IL-7 regulates peripheral T-cell homeostasis, and contributes to the generation and long-term survival of both CD4 and CD8 memory T lymphocytes in vivo.

In one embodiment the cytokines employed in the process according to the present disclosure are independently selected from IL-4, IL-7 and IL-15, especially IL-4 and IL-7.

In one embodiment the cytokines employed are IL-4 and/or IL-7. Whilst not wishing to be bound by theory the inventors believe that these cytokines have a role to play in shaping the frequency, repertoire and expansion of viral antigen-specific T cells.

The repertoire of T cells may be determined by ELISPOT analysis after stimulation with peptide libraries aliquotted into pools such that each peptide is uniquely represented in two pools (Kern, F., N. Faulhaber, C. Frommel, E. Khatamzas, S. Prosch, C. Schonemann, I. Kretzschmar, R. Volkmer-Engert, H. D. Volk, and P. Reinke. 2000. Analysis of CD8 T cell reactivity to cytomegalovirus using protein-spanning pools of overlapping pentadecapeptides. Eur J Immunol. 30:1676-1682 and Straathof, K. C., A. M. Leen, E. L Buza, G. Taylor, M. H. Huls, H. F. Heslop, C. M. Rooney, and C. M. Bollard. 2005. Characterization of latent membrane protein 2 specificity in CTL lines from patients with EBV-positive nasopharyngeal carcinoma and lymphoma. J. Immunol. 175:4137-4147).

IL-4 is generally employed at a final concentration of 250 ng/ml of culture or less, such as 200 ng/ml or less.

IL-7 is generally employed at a final concentration of 50 ng/ml of culture or less, such as 20 ng/ml or less, in particular 10 ng/ml.

If IL-15 is employed a suitable final concentration is 50 ng/ml of culture or less, such as 20 ng/ml or less, in particular 10 ng/ml.

In one embodiment in about 20 mls per GRex-10 (for example 20×10$^6$ PBMCs) a further 10 mls medium containing IL-4 (1666 units per mL) and IL-7 (long per ml) is added.

IL-12 has a role in Th1 focussing and exogenous IL-12 may be omitted if a balanced Th1/Th2 is desired. In one embodiment the process of the present disclosure does not employ exogenous IL-12. However, in the context of the present T cell product a Th1 response in the CD4+ population is thought to be desirable.

In one embodiment when IL-4 is employed the in the expansion process of the present disclosure at day 10 or day 11 the number of expanded cells may be 10, 20, 30, 40 50, 60, 70, 80, 90, 100 or 200% higher than cells expanded employing a similar protocol replacing IL-4 with IL-2.

However, even where after about 9, 10 or 11 days the number of antigen specific T cells provided from the IL-2 and IL-4/7 protocols are the same in terms of number of specific gamma secreting cells the IL-2 cells are much less viable. Cell viability may be tested as described herein.

When exogenous IL-2 is employed in the rapid expansion system hyper-proliferation of T cells is generated. When this hyper-rapid expansion occurs then the balance of desirable T cells and the residual cells is suboptimal in that the expansion happens so rapidly that many that the residual cells have not died and thus remain present in the total cell population. Thus the present inventors have reconciled the inherently incompatible factors of rapid expansion with the selectivity of culturing the cells for a period of time and have found that the omission of IL-2 improves the ratio of desired cells to residual cells. What is more in the period 7 to 14 days such as 10 days the ratio of desired cells to residual cells is a cross-over point where the cultured product becomes suitable for use in therapy. This cross-over point is defined as when a sufficient minimum dose of therapeutic T cells is achieved within a dose formulation which falls within the safety threshold of no more than $5 \times 10^5$ CD3+ T cells per kg of patient body weight.

It is expected by the inventors that this safety threshold will become the gold standard within the context of the optimal dosing for an antigen-specific T cell product aimed at providing immune reconstitution following bone marrow transplantation.

Whilst each final expanded T cell product may vary in the exact composition due to inherent differences in the starting donor sample the safety profile of the product can be controlled by monitoring the proportion of antigen specific T cells to residual cells. Advantageously, the product obtained from the process of the present invention can be controlled to ensure it is safe, in a clinical context.

In one embodiment the expanded antigen-specific T cell population obtained is biased to producing a CD4+ cell population.

In one embodiment the process of the present disclosure is employed to provide a cell population comprising a CD4+ T cell population, for example a Th1 population. A Th1 population as employed herein is intended to refer to a CD4+ population wherein 5% of the cells or more, such as 10, 20, 30, 40, 50, 60, 70, 80, 90% or more are classified as Th1.

Memory T cells are a component of Th1 cells.

In one embodiment the population of cells obtained from the process comprises a sub-population of memory T cells, for example the memory T cells represent 10, 20, 30, 40, 50 or 60% of the expanded cells and will generally express effector memory markers including CD27, CD28, CD62L and CD45RO. This will be a significantly higher than the population of memory cells prior to expansion.

Target antigen as employed herein is intended to refer to the antigen which is employed to the generate specificity in the T cells to the therapeutic target, such as a particular virus, for example CMV, adenovirus, EBV or BK Virus. Thus the cells infected by target virus or cancer cells will usually express the target antigen and hence will themselves become a target for clearance by the immune system. The immune system has the extraordinary capability to remove (kill) an infected cell from the body while ensuring minimal escape opportunities for the pathogen infecting the cell in question.

Residual CD3−, CD56+, and NK cells in the final cell population are acceptable since these are potentially beneficial.

The cell populations expanded using the process of the present disclosure comprises the desired T cell population and generally will not consist only of the desired population. The final product administered to the patient will include a number of other cells that the process did not target the expansion of. In one embodiment the desired population of CD4+ and CD8+ cells comprises about 60% or less, 70% or less, or 80% or less of the total population of cells. Frequency of the cell populations may be measured employing a gamma-IFN Elispot assay which is known to persons skilled in the art.

In one embodiment the T cells population obtained from the process are diverse when analysed by spectratyping, and without the emergence of dominant clone. That is to say the T cell diversity in the starting sample is substantially represented in the expanded T cells, i.e. the expansion is not generally the expansion of a single clone.

In one embodiment the relevant population of T cells prepared has a T cell receptor on the surface. In one or more embodiments the cell populations according to the present disclosure have one or more advantageous properties in comparison to cells prepared by the prior art method.

In one embodiment the antigen specific T cells of the present disclosure have an average cell diameter which is 95% or less, for example 90% or less, such as 85% or less, more specifically 80% or less of the maximum cell diameter.

In one embodiment the average cell diameter of cells in the relevant T cell population is in the range 10 to 14 microns and the average cell diameter is about 10, 11, 12, 13 or 14 microns.

We believe sufficient cells even for the highest doses can be prepared employing the method of the present disclosure.

Release Criteria for the product includes:
Identity: Greater than 50% CD3+ of CD45+ cells
Viability: Greater than 70% of CD45+ cells
Safety: CD3+ Dose not exceed specified number of T cells
Virus Specific: Minimum 100 Virus specific Cells per Kg defined by specific IFNg production Advantageously the cells cultures of the present invention exhibit generally low toxicity, for example are associated with few toxicity intolerance responses, for example inflammatory responses, cell damage, flu like symptom, nausea, hair loss or the like.

In some embodiments the cell populations according to the present disclosure may also provide one or more the following advantageous properties, for example levels of interferon gamma secretion, in vivo proliferation, up-regulation of a T cell activation marker (for example T cell receptors) may be high relative to the total number of antigen specific T cells in the population.

In one embodiment gamma-capture may be used to select a target cell population.

High levels of interferon gamma secretion as employed herein are intended to refer to the fact that on average (for example expressed as a mean) cells in a populations prepared by the current method may secrete higher levels of interferon gamma than cells prepared by prior art methods. In assaying this attribute, it may be necessary to rest the cells for a period after expansion before measuring the level of interferon gamma secretion. Although this is can be measured at the population level—when measured at the single cell level it will reveal that a higher percentage of cells will be antigen specific—i.e. producing interferon-gamma compared with cells made using the prior art In one embodiment the cells of the present disclosure may show enhanced antigen specificity, for example in an assay disclosure herein, in comparison to cells prepared by a prior art method.

In one embodiment the cell populations of the present disclosure show comparable avidity (not significantly different) to cell populations prepared by a prior art method.

The therapeutic antigen-specific T cell population provided may technically be a sub-therapeutic dose in the composition of the invention. However, after infusion into the patient the cells expand further to assist in reconstituting the patients' immune repertoire. Thus if the cells transfused are exhausted or anergic then the effectiveness of the cells in vivo is likely to compromised or reduced in one or more respects.

Thus "potency" or "biological effectiveness" of the cells is a really important consideration in the reconstitution abilities of the target therapeutic T cells.

The present inventors believe that this insight will lead to a paradigm shift in the current thinking and approach to T cell therapy in the field.

In one embodiment the T cell populations provided by the present disclosure are effective in expanding in vivo to provide an appropriate immune response to cells infected by a target virus and/or cancer cells associated with a target virus.

The present invention also extends to compositions comprising the allogeneic antigen-specific T cell populations according to the invention. These compositions may comprise a diluent, carrier, stabilizer, surfactant, pH adjustment or any other pharmaceutically acceptable excipient added to the cell population after the main process steps. An excipient will generally have a function of stabilizing the formulation, prolonging half-life, rendering the composition more compatible with the in vivo system of the patient or the like.

In one embodiment a protein stabilizing agent is added to the cell culture after manufacturing, for example albumin, in particular human serum album, which may act as a stabilizing agent. The amounts albumin employed in the formulation may be 1 to 50% w/w, for example 10 to 50% w/w, such as about 2.25, 4.5 or 12.5% w/w.

In one embodiment the formulation also contains a cryopreservative, for example glycerol or DMSO. The quantity of DMSO is generally 12% or less such as about 10% w/w.

In one embodiment the process of the present invention comprises the further step of preparing a pharmaceutical formulation by adding a pharmaceutically acceptable excipient, in particular an excipient as described herein, for example diluent, stabilizer and/or preservative.

Excipient as employed herein is a generic term to cover all ingredients added to the T cell population that do not have a biological or physiological function.

In one aspect there is provided a pharmaceutical composition of an allogeneic expanded antigen specific T cell population for a patient, wherein the composition comprises:
  a population of CD3+ T cells, where in the total population of CD3+ does not exceed $5 \times 10^5$ cells per Kg of patient, and said population of CD3+ T cells comprises a therapeutic T cell population of CD4+ cells characterization as a Th1 population, for example with some CD8+ CTLs;
  optionally the population of non-CD3+ cells is 20 percent or less of the total cell population of the composition
characterised in that the relevant expanded antigen-specific T cell population is able to expand in vivo. In one embodiment there is provided a pharmaceutical composition expanded antigen-specific T cell population for a patient, wherein the composition comprises:
  a population of at least 70% CD3+ T cells and less than 30 percent of non CD3+ cells, where the total population of CD3+ cells does not exceed $5 \times 10^4$ cells (or alternatively $1 \times 10^5$) per Kg of patient, and said population of CD3+ T cells comprises a therapeutic T cell population of CD4+ cells which have a primary characterization as Th1,
characterised in that the relevant expanded antigen specific T cell population is able to expand in vivo Analysis of whether the antigen specific T cells are suitable for expanding in vivo may be tested employing in vitro systems, for example using a cell proliferation assay, for example the CFSE assay described herein.

In one embodiment the expanded antigen specific T cells are capable of further expansion in vitro and in vivo, significant levels expansion for example include 2, 3, 4, 5 fold expansion or more.

In one embodiment at least 70% of the relevant cells are viable as measured by dye exclusion or flow cytometry, for example 75%, 80%, 85% or more of the cells are viable.

In one embodiment the expanded antigen specific T cell population are capable of producing Th1 cytokines, for example biologically relevant levels thereof.

Cell proliferation may be assayed by labelling cells with fluorescent compound CFSE to monitor division to a given stimulus. In short cells are labelled with CFSE and antigen is added which stimulates some cells to divide. These cells can be monitored as when they divide the amount of dye in each daughter cell is halved thus halving the brightness of the cell as detected by flow cytometry. Therefore the number of divisions the cell population has undergone can be determined.

Once the final formulation has been prepared it will be filled into a suitable container, for example an infusion bag or cryovial.

In one embodiment the process according to the present disclosure comprises the further step of filling the T cell population or pharmaceutical formulation thereof into a suitable container, such as an infusion bag and sealing the same.

In one embodiment the container filled with the T cell population of the present disclosure or a pharmaceutical composition comprising the same is frozen for storage and transport, for example is store at about −135° C.

In one embodiment the process of the present disclosure comprises the further step of freezing the T cell population of the present disclosure or a pharmaceutical composition comprising the same. In one embodiment the "product" is frozen by reducing the temperature by 1° C. per minute to ensure the crystals formed do not disrupt the cell structure. This process may be continued until the sample has reached about −100° C.

A product according to the present disclosure is intended to refer to a cultured cell population of the present disclosure or a pharmaceutical composition comprising the same.

In one embodiment the product is transferred, shipped, transported in a frozen form to the patient's location.

In one embodiment the product according to the present disclosure is provided in a form suitable for parenteral administration, for example, infusion, slow injection or bolus injection. In one embodiment the formulation is provided in a form suitable for intravenous infusion.

In one aspect the present disclosure provides a method of transport a product according to the present disclosure, from the place of manufacture, or a convenient collection point to the vicinity of the intended patient, for example where the T cell product is stored at or below 0° C. during transit, such as below −100° C.

In one embodiment the temperature fluctuations of the T cell product are monitored during storage and/or transport.

In one embodiment there is provided a product of the present disclosure for use in treatment, for example in the treatment of a viral pathogen such as adenovirus, CMV, EBV, human polyoma virus, herpes simplex virus, varicella zoster virus, hepatitis, rotavirus or similar.

In one embodiment the treatment is of an immunosuppressed patient.

In one embodiment there is a provided a method of treating a patient with a product according to the present disclosure comprising the step of administering a therapeutically effective amount of product defined herein.

Therapeutically effective amount does not necessarily mean an amount that is immediately therapeutically effective but includes a dose which is suitable for expansion in vivo (after administration) to provide a therapeutic effect.

It is envisaged that more than one embodiment described herein may be combined, as technically appropriate.

In the context of this specification "comprising" is to be interpreted as "including".

Aspects of the disclosure comprising certain elements are also intended to extend to alternative embodiments "consisting" or "consisting essentially" of the relevant elements.

All references referred to herein are specifically incorporated by reference.

Sili U et al Large-scale expansion of dendritic cell-primed polyclonal human cytotoxic T-lymphocyte lines using lymphoblastoid cells for adoptive immunotherapy. J. Immuother. 2003 May-June: 26(3): 241-56

Leen A M et al Contact-activated monocytes: efficient antigen presenting cells for the stimulation of antigen-specific T cells. J Immunother. 2007 January: 30(1): 96-107.

Bollard C M et al The generation and characterization of LMP2-specific CTL for use as adoptive transfer from patients with relapsed EBV-positive Hodgkin disease J. Immunother.

M G Wing, et al An Improved Method for the Detection of Cell Surface Antigens in Samples of Low Viability using Flow Cytometry. J Immunol Methods 126:21-27, 1990

D R Parks, et al Chapter 29 Flow Cytometry and Fluorescence-Activated Cell Sorting (FACS). Handbook of Experimental Immunology, DM Weir (ed), Blackwell Scientific Publications, M A, 1986

I Schmid et al Dead Cell Discrimination with 7-aminoactinomycin D in Combination with Dual Colour Immunofluorescence in Single Laser Flow Cytometry. Cytometry 13:204, 1992

F deBoer et al Extensive early apoptosis in frozen thawed CD34+ stem cells decreases threshold doses for haematological recovery after autologous peripheral blood progenitor cell transplant. Bone marrow Transplant 29:249-255, 2002

R S Anthony, et al. Flow cytometry using annexin V can detect early apoptosis in peripheral blood stem cell harvests from patients with leukemia and lymphoma. Bone Marrow Transplant 21:441-446, 1998.

James W Tung, et al. Modern Flow Cytometry: A Practical Approach. Clin Lab Med 27(3):453, 2007 (September)

EXAMPLES

Expansion of the Antigen Specific T Cell Product

Reagents

This procedure describes the production and cryopreservation of an adoptive cellular therapy, produced using a Wilson Wolfe GRex system

| Reagents | Manufacturer | Catalogue No. |
| --- | --- | --- |
| RPMI 1640 | Invitrogen Ltd | 61870 |
| Human AB serum | | |
| DMSO | Wak chemie | WAK-DMSO-70 |
| Lymphoprep | AxisSheild | 11114445 |
| Human Serum Albumin (HSA), 4.5% | BPL | PL08801/0006 |
| IL-4 | CellGenix | 1003 |
| IL-7 | CellGenix | 1010 |
| AdV-5 | Miltenyi | 76106 |
| WFI | Gibco | A12873 |

A peptide or peptide mix from the target virus such as CMV pp65 or PepTivator®

| EQUIPMENT | Manufacturer | Specifications |
| --- | --- | --- |
| Centrifuge Rotina 46R | Not Specified | 300 × 'g' |
| Digital Balance | Not specified | Weight |
| Plasma Press | Baxter | N/A |
| $CO_2$ Incubator | Not specified | 37 ± 2° C., 5 ± 1° C., |
| Heat Sealer | Baxter | N/A |
| Sterile Welder | Terumo | N/A |
| Class II Biological safety cabinet | Not specified | N/A |
| Kryo 560-16 | Planer | TBC |
| Vacuum chamber | Multivac | N/A |
| Sepax Blood Processor | Biosafe | N/A |
| Micropipettes | Gilson | N/A |

Incoming Blood Product Receipt:

All donors must be screened for Markers of Infectious Diseases (Hepatitis B surface antigen, Hepatitis C, Syphilis, HTLV I and II and HIV markers) within 30 days of the donor blood product extraction. Should a donor have tested positive for any infectious disease, the product collection will not be carried out and the processing cancelled.

IL-4

Dilute a 50 µg vial of IL-4 with 250 µl of Water For Injection, producing a 200 µg/ml stock solution. 20 µl of diluted sample is added per culture when required. The remaining sample is aliquoted into 50 µl aliquots in 1.8 ml Nunc Cryovials. If using a frozen batch of IL-4 ensure the material is fully thawed before use.

IL-7

Dilute 50 µg vial of IL-7 with 200 µl of Water For Injection (WFI), The solution is further diluted 1:25, by adding 240 µl of WFI to produce a 10 µg/ml working stock. 20 µl of this is then used per culture. The remaining sample is aliquoted into 50 µl aliquots in 1.8 ml Nunc Cryovials. If using a frozen batch of IL-7 ensure the material is fully thawed before use Peptide The peptide is reconstituted by adding 2 ml of WFI into the 100 µg/peptide vial. 100 µl of the reconstituted peptide is removed and further diluted in 900 µl of WFI. 20 µL of the diluted peptide is then added to each culture. 50 µl aliquots of the reconstituted peptide are dispensed into Nunc cryovials. The remaining 1500 µl of concentrated peptide (50 µg/ml) is released for use in the QC assays.

RPMI For Washing

Spike a 5 L bag of RPMI the coupler from a 600 ml transfer pack. Place the transfer pack onto a tared balance and transfer approximately 500 ml (500 g) of RPMI. Once all the buffer has been transferred heat seal the line three times. Label as 'Patient Identifier, 500 ml for washing and leave at 2-8° C. until required for use.

RPMI For Inoculation

Weld on a fresh 600 ml transfer pack onto the remaining tubing connected to the 5 L bag of RPMI, using a tared balance transfer approximately 100 ml of RPMI into the bag.

Lymphoprep

Spike a bottle of Lymphoprep with the coupler from a 1000 ml bag. Spike the Lymphoprep with two air inlets and transfer 100 ml of into the bag. Label as 'Patient Identifier, 100 ml Lymphoprep.

Mononuclear Cells Preparation-Day 0

PBMC are prepared by density gradient centrifugation on the sepax device, a protocol known to those skilled in the art.

Example 1 Process for 226 CMV

Day –0

Buffer Preparation

IL-4

A 50 µg vial of IL-4 (USP grade, CellGenix cat 1003-050) was diluted with 250 µL of WFI (USP Grade Invitrogen Cat A12873) to produce a 200 µg/ml stock solution. The stock solution was stored at –80° C. with an aliquot being left for use in the pot inoculation

IL-7

A 50 µg vial of IL-4 (GMP, Cellgenix cat 1010-050) was diluted with 200 µL of WFI (USP Grade Invitrogen Cat A12873) to produce a stock. The stock was diluted 1:25 with WFI to produce a working stock, which was then stored at –80° C. with an aliquot being left for use in the pot inoculation.

CMV PepTivator Peptide

A 60 nmol/peptide peptide (GMP PepTivator pp65) was reconstituted in 2 ml of WFI (USP Grade Invitrogen Cat A12873). 100 µl of the reconstituted peptide was removed and further diluted in 900 µl of WFI. 20 µL of the diluted peptide was retained for pot inoculation with the remaining volume aliquoted and stored at –80° C.

RPMI

A 5 L bag of RPMI+ Glutamax (Invitrogen Cat 61870) was connected to a 600 ml transfer pack and 500 ml of RPMI transferred (product washing). The RPMI was welded onto a $2^{nd}$ 600 ml transfer pack and a further 100 ml transferred (pot inoculation), Lymphoprep 100 ml of Lymphoprep (Axis Shield Cat 1114740) was drained into a 1000 ml transfer pack and set aside for use within the DGBS (Density gradient based separation) cycle Cell Manipulation 100 ml of non-mobilised aphaeresis arrived on site, after a temperature monitored shipment at 2-8° C., from a matched donor. A 3 ml sample (STA) of the cell product was removed and 1 ml inoculated into a set of Bactecs. The following QC and in-process testing was also performed on the remaining starting material with the results displayed in the table below.

Cell Count, performed on automated cell counter
Absolute T cell Enumeration via Trucount (CD3-FITC, CD8-PE, CD45-PerCP)
Viability Stain (CD3-FITC, CD45-PE, CD8-PerCP)

| WBC Count | $34.4 \times 10^6$/ml |
|---|---|
| Lymphocyte % | 80.5% |
| Absolute CD3 Conc | $21.6 \times 10^6$ |
| Viability | 98.87% |
| Haematocrit | 1.6% |

The 500 ml bag of RPMI and 100 ml of Lymphoprep were connected to the CS900.02 along with the remaining contents of the incoming whole blood materials (97 ml). The V128 DGBS cycle was selected on the Sepax and the kit installed. On completion of the cycle 42 ml of PBMC's were eluted and the following testing performed.

A 1 ml sample of removed from the elution bag and the following tests were performed Cell Count, performed on automated cell counter
Absolute T cell Enumeration via Trucount (CD3-FITC, CD8-PE, CD45-PerCP)
Viability Stain (CD3-FITC, Cd45-PE, CD8-PerCP)

| WBC Count | $48.0 \times 10^6$/ml |
|---|---|
| Lymphocyte % | 79.2% |
| Absolute CD3 Conc | $20.66 \times 10^6$/ml |
| Viability | 97.58% |

$20 \times 10^6$ WBC's (410 µl of cell suspension) were inoculated into the Wilson Wolfe Biopot (GP-40 Bioreactor) along with 2 ml of Human AB serum (GMP German Blood Service) and 20 µl of the IL-4/IL-7 and peptide. The total volume is made up to 20 ml using RPMI (19.6 ml).

The pot was then incubated for 10 days in a 37±2° C., 5±1% $CO_2$, 95% humidity incubator.

Day –10

Cell Washing

On day 10 the pot is removed from the incubator and gently agitated to resuspend the cells from the base of the Wilson Wolfe biopot. A 2 ml sample is removed with 2×250 µL being using for *Mycoplasma* testing. The remaining sample is used in the following in process testing Manual cell count with Trypan Blue
T Cell Identity CD3-FITC, CD56-PE, CD45-PerCP

| Volume Recovered | 12.5 ml |
|---|---|
| WBC Cell Count | $3.6 \times 10^6$ |
| Viability | 73% |

A 230 ml bag of 4.5% HAS (BPL) was prepared and the remaining cell suspension was diluted before being spun at 300×'g' for 10 minutes. On completion of the spin the cell pack the supernatant is removed using a plasma press before the cells are resuspened and diluted in a further 230 ml of 4.5% HSA. The cells are given a final spin at 300×'g' for 10 minutes before the supernatant is again removed. The pellet is resuspended in fresh 4.5% HSA.

A 1 ml sample is removed and the following QC and in process testing performed

Intra-cellular gamma stain

| IFN-Gamma + T cells | 15.07% |
|---|---|

Freezing and Shipping 100 ml of 20% DMSO (Cryosure-DMSO, Wak-Chernie) solution IN 4.5% HSA (BPL) was prepared and chilled on ice packs The cell dose required is =3×10⁴ Tcells/kg
Patient Weight=16 kg
Therefore Cells Required=480,000 T cells
The following volumes were transferred into a suitably sized Cryocyte bag via a Cryocyte manifold set.

| Cell Suspension | 0.13 ml |
|---|---|
| 4.5% has | 9.87 ml |
| 20% DMSO in 4.5% HSA | 10.0 ml |

A 3 ml sample was removed from the Cryocyte bag with 2 ml being inoculated into one of each of a set of Bactecs. The remaining 1 ml of sample was stored at −80° C. and sent for Endotoxin testing. The Cryocyte bag containing the cell product was placed within a controlled rate freezer and the cells frozen at a rate of −1° C./min until −30° C. and then reduced at −2° C./min to −100° C. On completion of the freezing cycle the cells were placed with the vapour phase of a temperature monitored $LN_2$ Dewar. The following safety testing results were obtained prior to product release.

| Sterility | No growth detected |
|---|---|
| Mycoplasma | Negative |
| Endotoxin | ≤10 EU/ml |

Once requested by the patients physician the product was released by the QP before being shipped to the relevant stem cell labs within a validated, temperature monitored dry shipper. Upon arrival the cells were stored within the vapour phase of the stem cells labs dewars until infusion.

Example 2 Process for 226 ADV

Day −0
Buffer Preparation
IL-4
A 50 µg vial of IL-4 (USP grade, CellGenix cat 1003-050) was diluted with 250 µL of WFI (USP Grade Invitrogen Cat A12873) to produce a 200 µg/ml stock solution. The stock solution was stored at −80° C. with an aliquot being left for use in the pot inoculation
IL-7
A 50 µg vial of IL-4 (GMP, Cellgenix cat 1010-050) was diluted with 200 µL of WFI (USP Grade Invitrogen Cat A12873) to produce a stock. The stock was diluted 1:25 with WFI to produce a working stock, which was then stored at −80° C. with an aliquot being left for use in the pot inoculation.
ADV PepTivator Peptide
A 60 nmol/peptide peptide (GMP PepTivator hexon V) was reconstituted in 2 ml of WFI (USP Grade Invitrogen Cat A12873). 100 µl of the reconstituted peptide was removed and further diluted in 900 µl of WFI. 20 µL of the diluted peptide was retained for pot inoculation with the remaining volume aliquoted and stored at −80° C.
RPMI
A 5 L bag of RPMI+ Glutamax (Invitrogen Cat 61870) was connected to a 600 ml transfer pack and 500 ml of RPMI transferred (product washing). The RPMI was welded onto a $2^{nd}$ 600 ml transfer pack and a further 100 ml transferred (pot inoculation),
Lymphoprep
100 ml of Lymphoprep (Axis Shield Cat 1114740) was drained into a 1000 ml transfer pack and set aside for use within the DGBS (Density gradient based separation) cycle Cell Manipulation
100 ml of non-mobilised aphaeresis arrived on site, after a temperature monitored shipment at 2-8° C., from a matched donor. A 3 ml sample (STA) of the cell product was removed and 1 ml inoculated into a set of Bactecs. The following QC and in-process testing was also performed on the remaining starting material with the results displayed in the table below.
Cell Count, performed on automated cell counter
Absolute T cell Enumeration via Trucount (CD3-FITC, CD8-PE, CD45-PerCP)
Viability Stain (CD3-FITC, CD45-PE, CD8-PerCP)

| WBC Count | 34.4 × 10⁶/ml |
|---|---|
| Lymphocyte % | 80.5% |
| Absolute CD3 Conc | 21.6 × 10⁶ |
| Viability | 98.87% |
| Haematocrit | 1.6% |

The 500 ml bag of RPMI and 100 ml of Lymphoprep were connected to the CS900.02 along with the remaining contents of the incoming whole blood materials (97 ml). The V128 DGBS cycle was selected on the Sepax and the kit installed. On completion of the cycle 42 ml of PBMC's were eluted and the following testing performed.
A 1 ml sample of removed from the elution bag and the following tests were performed
Cell Count, performed on automated cell counter
Absolute T cell Enumeration via Trucount (CD3-FITC, CD8-PE, CD45-PerCP)
Viability Stain (CD3-FITC, Cd45-PE, CD8-PerCP)

| WBC Count | 48.0 × 10⁶/ml |
|---|---|
| Lymphocyte % | 79.2% |
| Absolute CD3 Conc | 20.66 × 10⁶/ml |
| Viability | 97.58% |

20×10⁶ WBC's (410 µl of cell suspension) were inoculated into the Wilson Wolfe Biopot (GP-40 Bioreactor) along with 2 ml of Human AB serum (GMP German Blood Service) and 20 µl of the IL-4/IL-7 and peptide. The total volume is made up to 20 ml using RPMI (19.6 ml).
The pot was then incubated for 10 days in a 37±2° C., 5±1% $CO_2$, 95% humidity incubator.
Day −10
Cell Washing
On day 10 the pot is removed from the incubator and gently agitated to resuspend the cells from the base of the Wilson Wolfe biopot. A 2 ml sample is removed with 2×250 µL being using for *Mycoplasma* testing. The remaining sample is used in the following in process testing
Manual cell count with Trypan Blue
T Cell Identity CD3-FITC, CD56-PE, CD45-PerCP

| Volume Recovered | 12.5 ml |
|---|---|
| WBC Cell Count | 3.6 × 10⁶ |
| Viability | 97.22% |

A 230 ml bag of 4.5% HAS (BPL) was prepared and the remaining cell suspension was diluted before being spun at 300×'g' for 10 minutes. On completion of the spin the cell pack the supernatant is removed using a plasma press before the cells are resuspended and diluted in a further 230 ml of 4.5% HSA. The cells are given a final spin at 300×'g' for 10 minutes before the supernatant is again removed. The pellet is resuspended in fresh 4.5% HSA.

A 1 ml sample is removed and the following QC and in process testing performed

Intra-cellular gamma stain

| IFN-Gamma + T cells | 17.14% |
|---|---|

Freezing and Shipping 100 ml of 20% DMSO (Cryosure-DMSO, Wak-Chemie) solution IN 4.5% HSA (BPL) was prepared and chilled on ice packs The cell dose required is =$3 \times 10^4$ Tcells/kg Patient Weight=16 kg Therefore Cells Required=480,000 T cells The following volumes were transferred into a suitably sized Cryocyte bag via a Cryocyte manifold set.

| Cell Suspension | 0.13 ml |
|---|---|
| 4.5% HSA | 9.87 ml |
| 20% DMSO in 4.5% HSA | 10.0 ml |

A 3 ml sample was removed from the Cryocyte bag with 2 ml being inoculated into one of each of a set of Bactecs. The remaining 1 ml of sample was stored at −80° C. and sent for Endotoxin testing. The Cryocyte bag containing the cell product was placed within a controlled rate freezer and the cells frozen at a rate of −1° C./min until −30° C. and then reduced at −2° C./min to −100° C. On completion of the freezing cycle the cells were placed with the vapour phase of a temperature monitored $LN_2$ Dewar. The following safety testing results were obtained prior to product release.

| Sterility | No growth detected |
|---|---|
| Mycoplasma | Negative |
| Endotoxin | ≤10 EU/ml |

Once requested by the patients physician the product was released by the QP before being shipped to the relevant stem cell labs within a validated, temperature monitored dry shipper. Upon arrival the cells were stored within the vapour phase of the stem cells labs dewars until infusion.

Example 3

The starting population of cells was cultured in an adapted G-Rex system as shown in the Figures employing RPMI 1640 media in the presence of 10% human serum, IL4, IL7 and an overlapping peptide pool specific for the desired antigen. For CMV specific expansion then the peptide employed was pp65. For adenovirus (ADV) overlapping peptides for the ad 5 hexon were employed. A seed density of 0.5, 1 or $2 \times 10^6/cm^2$ was employed. The results established that $2 \times 10^6/cm^2$ lead to maximal cell expansion see Table 1 Seeding Density for CMV expansion:

|  |  | Day 0 | Day 5 | Day 9 | Day 12 |
|---|---|---|---|---|---|
| Donor I | no cyto | 20000000 | 18300000 | 13500000 | 14100000 |
|  | IL4/7 | 20000000 | 29100000 | 108000000 | 120000000 |
|  | no cyto | 10000000 | 7800000 | 6900000 | 8100000 |
|  | IL4/7 | 10000000 | 13500000 | 43500000 | 81000000 |
|  | no cyto | 5000000 | 1800000 | 2100000 | 1900000 |
|  | IL4/7 | 5000000 | 4200000 | 6400000 | 3900000 |
| Donor II | no cyto | 20000000 | 13500000 | 15000000 | 22800000 |
|  | IL4/7 | 20000000 | 14700000 | 34500000 | 120000000 |
|  | no cyto | 10000000 | 4500000 | 5500000 | 5000000 |
|  | IL4/7 | 10000000 | 12500000 | 32000000 | 75000000 |
|  | no cyto | 5000000 | 4200000 | 2100000 | 2700000 |
|  | IL4/7 | 5000000 | 2700000 | 6300000 | 21000000 |
| Donor III | no cyto | 20000000 | 9900000 | 11100000 | 13500000 |
|  | IL4/7 | 20000000 | 13500000 | 24000000 | 49000000 |
|  | no cyto | 10000000 | 5100000 | 6000000 | 5500000 |
|  | IL4/7 | 10000000 | 10500000 | 12000000 | 24000000 |
|  | no cyto | 5000000 | 2100000 | 3500000 | 3000000 |
|  | IL4/7 | 5000000 | 2500000 | 4200000 | 4500000 |

The melange was cultured for 12 about 12 days at 37° C., without stirring or agitation. Samples were taken daily and analysed or as required.

The total cell count of the expanded population was measured. The results for two donors are shown in FIGS. 4A and 4B The amount of cells specific for CMV which secrete cytokines were tested. The results for two donors are shown in FIGS. 5A and 5B Cell growth rates were measures and results for CMV specific expansions are shown in FIG. 6A and for adeno specific expansions are shown in FIG. 6B.

Adeno and CMV specific cytokine production was measured using elispot and the results are shown in FIG. 7.

FIG. 8 shows a comparison of two expansion protocol, wherein the only cytokine employed is IL2 or IL4.

FIG. 9 show the expansion protocol of Example 7 employing different concentrations of peptides. At around day 9 or 10 the system employing 5 ng/ml (CMV) seems to have improved performance in terms of cell expansion.

FIG. 10 shows IFN-gamma production of the cells cultured using different concentrations of peptide. At around day 9 or 10 the system employing 5 ng/ml (CMV) seems to perform best.

The invention claimed is:

1. An in vitro expansion process for rapid of antigen specific T cells, comprising culturing in a vessel comprising a gas permeable culture surface a population of PBMCs in a culture in the presence of an antigen, wherein the antigen is in the form of a peptide or a peptide mix relevant to a target antigen(s) and wherein the antigen is added to the culture in the range of from 1 to 500 ng per ml; wherein the culturing is performed in the presence of an exogenous cytokine wherein the cytokine is other than exogenous IL-2 and is selected from the group comprising IL-1, IL-4, IL-6, IL-7, IL-12, IL-15 and combinations thereof; wherein antigens, cytokines, media and nutrients are not added or changed after initiation of the expansion process; wherein the expansion to provide the desired population of T cells is 20 days or less; wherein the desired population of cells is a CD56− population; and wherein the peptide or peptide mix is/are not added to the culture presented on dendritic cells.

2. An in vitro process according to claim 1, wherein the exogenous cytokine is selected from the group comprising IL-4, IL-7, IL-15 or a combination thereof.

3. An in vitro process according to claim 2, wherein the exogenous cytokine is a combination of IL-4 and IL-7.

4. An in vitro process according to claim 1, wherein the culture is performed in the presence of a T cell expansion medium.

5. An in vitro process according to claim 1, wherein the peptide mix comprises 2 to 1000 peptides, 2 to 500 peptides, 2 to 400 peptides, 2 to 300 or 2 to 200 peptides.

6. An in vitro process according to claim 5, wherein the peptides overlap by 2, 3, 4, 5, 6, 7, 8, 9, 10, 11, 12 or more amino acids.

7. An in vitro process according to claim 1, wherein the expansion is performed for 18 days or less.

8. An in vitro process according to claim 1, wherein the initial PBMC sample derived from a donor is a mobilised sample or mobilised apheresis sample.

9. An in vitro process according to claim 1, wherein the gas permeable vessel is a GRex system or a derivative or an equivalent system.

10. An in vitro process according to claim 9, wherein the GRex system has been adapted to provide a closed system, suitable for aseptic manufacture.

11. An in vitro process according to claim 1, wherein the process is performed aseptically or in a clean room.

12. An in vitro process according claim 1, further comprising preparing a pharmaceutically acceptable composition by adding a diluent, stabilizer, preservative and/or other pharmaceutically acceptable excipient.

13. An in vitro process according to claim 12, further comprising filling the antigen specific T cell population or a pharmaceutical composition comprising the same into a container such as infusion bag and sealing the container.

14. An in vitro process for rapid expansion of antigen specific T cells, comprising culturing in a gas permeable vessel a population of PBMCs in a culture in the presence of an antigen, wherein the antigen is in the form of a peptide or a peptide mix relevant to a target antigen(s) and wherein the antigen is added to the culture in the range of from 1 to 500 ng per ml; wherein the culturing is performed in the presence of an exogenous cytokine wherein the cytokine is other than exogenous IL-2 and is selected from the group comprising IL-1, IL-4, IL-6, IL-7, IL-12, IL-15 and combinations thereof; wherein the process consists of expanding the antigen-specific T cells for 20, 18, 17, 16, 15, 14, 13, 12, 11, 10, 9, 8, 7 days or less wherein the desired population of cells is a CD56− population, and the peptide or peptide mix is/are not added to the culture presented on dendritic cells; and wherein antigens, cytokines, media and nutrients are not added or changed after initiation of the expansion process.

15. An in vitro process according to claim 1, wherein the target antigen is a CMV-specific antigen.

16. An in vitro process according to claim 1, wherein said population of PBMCs is cultured from a donor sample of 50 to 100 ml.

17. An in vitro process according to claim 1, wherein said desired population of T cells comprises CD3+ T cells.

18. An in vitro process according to claim 17, wherein said desired population of T cells comprises at least 70% CD3+ T cells.

19. An in vitro process according to claim 1, wherein the expanded population of T cells is polyclonal.

20. An in vitro process according to claim 1, wherein the cytokine or cytokine combination does not comprise exogenous G-CSF.

21. An in vitro process according to claim 1, wherein the antigen is in the form of a peptide or a peptide mix relevant to a target antigen(s) added to the cultured in the range of from 4 to 10 ng per ml; wherein the exogenous cytokine is IL-4, IL-7 or a combination thereof; and wherein the expansion is performed for 18 days or less.

22. An in vitro process according to claim 14, wherein the cytokine or cytokine combination does not comprise exogenous G-CSF.

23. An in vitro process according to claim 14, wherein the antigen is in the form of a peptide or a peptide mix relevant to a target antigen(s) added to the cultured in the range of from 4 to 10 ng per ml; wherein the exogenous cytokine is IL-4, IL-7 or a combination thereof; and wherein the expansion is performed for 18, 17, 16, 15, 14, 13, 12, 11 or 10 days.

24. An in vitro process according to claim 1, wherein the expansion is performed for 18, 17, 16, 15, 14, 13, 12, 11 or 10 days.

25. An in vitro process according to claim 1, wherein the step of culturing in a vessel comprising a gas permeable culture surface a population of PBMCs occurs on Day 0.

26. An in vitro process according to claim 14, wherein the step of culturing in a vessel comprising a gas permeable culture surface a population of PBMCs occurs on Day 0.

27. An in vitro process for rapid expansion of antigen specific T cells, comprising culturing in a vessel comprising a gas permeable culture surface a population of PBMCs in a culture in the presence of an antigen, wherein the antigen is in the form of a peptide or a peptide mix relevant to a target antigen(s); wherein the culturing is performed in the presence of an exogenous cytokine wherein the cytokine is other than exogenous IL-2 and is selected from the group comprising IL-1, IL-4, IL-6, IL-7, IL-12, IL-15 and combinations thereof; wherein antigens, cytokines, media and nutrients are not added or changed after initiation of the expansion process; wherein the expansion to provide the desired population of T cells is 20 days or less; wherein the desired population of cells is a CD56− population; and wherein the peptide or peptide mix is/are not added to the culture presented on dendritic cells.

28. The in vitro process of claim 27, wherein the expansion to provide the desired population of T cells is 16 days or less and the exogenous cytokines consist of IL-4 and IL-7.

\* \* \* \* \*

UNITED STATES PATENT AND TRADEMARK OFFICE
CERTIFICATE OF CORRECTION

PATENT NO. : 11,963,979 B2
APPLICATION NO. : 16/016305
DATED : April 23, 2024
INVENTOR(S) : Rainer Ludwig Knaus et al.

It is certified that error appears in the above-identified patent and that said Letters Patent is hereby corrected as shown below:

In the Claims

At Column 135, Claim number 1, Line number 26:
"An in vitro expansion process for rapid of antigen"
Should read:
--An in vitro process for rapid expansion of antigen--

Signed and Sealed this
Twenty-sixth Day of November, 2024

Katherine Kelly Vidal
*Director of the United States Patent and Trademark Office*

SEQUENCE LISTING

```
<160> NUMBER OF SEQ ID NOS: 340

<210> SEQ ID NO 1
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 1
```

Met Ser Asp Glu Gly Pro Gly Thr Gly Pro Asn Gly Leu Gly
1               5                   10                  15

<210> SEQ ID NO 2
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 2

Gly Pro Gly Thr Gly Pro Gly Asn Gly Leu Gly Glu Lys Gly Asp
1               5                   10                  15

<210> SEQ ID NO 3
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 3

Gly Pro Gly Asn Gly Leu Gly Glu Lys Gly Asp Thr Ser Gly Pro
1               5                   10                  15

<210> SEQ ID NO 4
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 4

Gly Leu Gly Glu Lys Gly Asp Thr Ser Gly Pro Glu Gly Ser Gly
1               5                   10                  15

<210> SEQ ID NO 5
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 5

Lys Gly Asp Thr Ser Gly Pro Glu Gly Ser Gly Gly Ser Gly Pro
1               5                   10                  15

<210> SEQ ID NO 6
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 6

Ser Gly Pro Glu Gly Ser Gly Gly Ser Gly Pro Gln Arg Arg Gly
1               5                   10                  15

<210> SEQ ID NO 7
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 7

Gly Ser Gly Gly Ser Gly Pro Gln Arg Arg Gly Gly Asp Asn His

<210> SEQ ID NO 8
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 8

Ser Gly Pro Gln Arg Arg Gly Gly Asp Asn His Gly Arg Gly Arg
1               5                   10                  15

<210> SEQ ID NO 9
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 9

Arg Arg Gly Gly Asp Asn His Gly Arg Gly Arg Gly Arg Gly Arg
1               5                   10                  15

<210> SEQ ID NO 10
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 10

Asp Asn His Gly Arg Gly Arg Gly Arg Gly Arg Gly Arg Gly Gly
1               5                   10                  15

<210> SEQ ID NO 11
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 11

Arg Gly Arg Gly Arg Gly Arg Gly Arg Gly Gly Gly Arg Pro Gly
1               5                   10                  15

<210> SEQ ID NO 12
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 12

Arg Gly Arg Gly Arg Gly Gly Gly Arg Pro Gly Ala Pro Gly Gly
1               5                   10                  15

<210> SEQ ID NO 13
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 13

Arg Gly Gly Gly Arg Pro Gly Ala Pro Gly Gly Ser Gly Ser Gly
1               5                   10                  15

```
<210> SEQ ID NO 14
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 14

Arg Pro Gly Ala Pro Gly Gly Ser Gly Ser Gly Pro Arg His Arg
1               5                   10                  15

<210> SEQ ID NO 15
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 15

Pro Gly Gly Ser Gly Ser Gly Pro Arg His Arg Asp Gly Val Arg
1               5                   10                  15

<210> SEQ ID NO 16
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 16

Gly Ser Gly Pro Arg His Arg Asp Gly Val Arg Arg Pro Gln Lys
1               5                   10                  15

<210> SEQ ID NO 17
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 17

Arg His Arg Asp Gly Val Arg Arg Pro Gln Lys Arg Pro Ser Cys
1               5                   10                  15

<210> SEQ ID NO 18
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 18

Gly Val Arg Arg Pro Gln Lys Arg Pro Ser Cys Ile Gly Cys Lys
1               5                   10                  15

<210> SEQ ID NO 19
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 19

Pro Gln Lys Arg Pro Ser Cys Ile Gly Cys Lys Gly Thr His Gly
1               5                   10                  15
```

```
<210> SEQ ID NO 20
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 20

Pro Ser Cys Ile Gly Cys Lys Gly Thr His Gly Gly Arg Gly Arg
1               5                   10                  15

<210> SEQ ID NO 21
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 21

Gly Cys Lys Gly Thr His Gly Gly Arg Gly Arg Gly Gly Ser Gly
1               5                   10                  15

<210> SEQ ID NO 22
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 22

Thr His Gly Gly Arg Gly Arg Gly Gly Ser Gly Gly Arg Arg Gly
1               5                   10                  15

<210> SEQ ID NO 23
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 23

Arg Gly Arg Gly Gly Ser Gly Gly Arg Arg Gly Arg Gly Arg Glu
1               5                   10                  15

<210> SEQ ID NO 24
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 24

Gly Ser Gly Gly Arg Arg Gly Arg Gly Arg Glu Arg Ala Arg Gly
1               5                   10                  15

<210> SEQ ID NO 25
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 25

Arg Arg Gly Arg Gly Arg Glu Arg Ala Arg Gly Gly Ser Arg Glu
1               5                   10                  15
```

```
<210> SEQ ID NO 26
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 26

Gly Arg Glu Arg Ala Arg Gly Gly Ser Arg Glu Arg Ala Arg Gly
1               5                   10                  15

<210> SEQ ID NO 27
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 27

Ala Arg Gly Gly Ser Arg Glu Arg Ala Arg Gly Arg Gly Arg Gly
1               5                   10                  15

<210> SEQ ID NO 28
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 28

Ser Arg Glu Arg Ala Arg Gly Arg Gly Arg Gly Arg Gly Glu Lys
1               5                   10                  15

<210> SEQ ID NO 29
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 29

Ala Arg Gly Arg Gly Arg Gly Arg Gly Glu Lys Arg Pro Arg Ser
1               5                   10                  15

<210> SEQ ID NO 30
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 30

Gly Arg Gly Arg Gly Glu Lys Arg Pro Arg Ser Pro Ser Ser Gln
1               5                   10                  15

<210> SEQ ID NO 31
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 31

Gly Glu Lys Arg Pro Arg Ser Pro Ser Ser Gln Ser Ser Ser Ser
1               5                   10                  15

<210> SEQ ID NO 32
```

-continued

```
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 32

Pro Arg Ser Pro Ser Ser Gln Ser Ser Ser Ser Gly Ser Pro Pro
1               5                   10                  15

<210> SEQ ID NO 33
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 33

Ser Ser Gln Ser Ser Ser Ser Gly Ser Pro Pro Arg Arg Pro Pro
1               5                   10                  15

<210> SEQ ID NO 34
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 34

Ser Ser Ser Gly Ser Pro Pro Arg Arg Pro Pro Pro Gly Arg Arg
1               5                   10                  15

<210> SEQ ID NO 35
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 35

Ser Pro Pro Arg Arg Pro Pro Pro Gly Arg Arg Pro Phe Phe His
1               5                   10                  15

<210> SEQ ID NO 36
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 36

Arg Pro Pro Pro Gly Arg Arg Pro Phe Phe His Pro Val Gly Glu
1               5                   10                  15

<210> SEQ ID NO 37
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 37

Gly Arg Arg Pro Phe Phe His Pro Val Gly Glu Ala Asp Tyr Phe
1               5                   10                  15

<210> SEQ ID NO 38
<211> LENGTH: 15
```

```
<212> TYPE: PRT
<213> ORGANISM: Virus Herpesviridae
<220> FEATURE:
<223> OTHER INFORMATION: EBV-protein EBNA1 fragment

<400> SEQUENCE: 38

Phe Phe His Pro Val Gly Glu Ala Asp Tyr Phe Glu Tyr His Gln
1               5                   10                  15

<210> SEQ ID NO 39
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 39

Val Gly Glu Ala Asp Tyr Phe Glu Tyr His Gln Glu Gly Gly Pro
1               5                   10                  15

<210> SEQ ID NO 40
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 40

Asp Tyr Phe Glu Tyr His Gln Glu Gly Gly Pro Asp Gly Glu Pro
1               5                   10                  15

<210> SEQ ID NO 41
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 41

Tyr His Gln Glu Gly Gly Pro Asp Gly Glu Pro Asp Val Pro Pro
1               5                   10                  15

<210> SEQ ID NO 42
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 42

Gly Gly Pro Asp Gly Glu Pro Asp Val Pro Pro Gly Ala Ile Glu
1               5                   10                  15

<210> SEQ ID NO 43
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 43

Gly Glu Pro Asp Val Pro Pro Gly Ala Ile Glu Gln Gly Pro Ala
1               5                   10                  15

<210> SEQ ID NO 44
<211> LENGTH: 15
<212> TYPE: PRT
```

<213> ORGANISM: Virus Herpesviridae
<220> FEATURE:
<223> OTHER INFORMATION: EBV-protein EBNA1 fragment

<400> SEQUENCE: 44

```
Val Pro Pro Gly Ala Ile Glu Gln Gly Pro Ala Asp Asp Pro Gly
1               5                   10                  15
```

<210> SEQ ID NO 45
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 45

```
Ala Ile Glu Gln Gly Pro Ala Asp Asp Pro Gly Glu Gly Pro Ser
1               5                   10                  15
```

<210> SEQ ID NO 46
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 46

```
Gly Pro Ala Asp Asp Pro Gly Glu Gly Pro Ser Thr Gly Pro Arg
1               5                   10                  15
```

<210> SEQ ID NO 47
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 47

```
Asp Pro Gly Glu Gly Pro Ser Thr Gly Pro Arg Gly Gln Gly Asp
1               5                   10                  15
```

<210> SEQ ID NO 48
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 48

```
Gly Pro Ser Thr Gly Pro Arg Gly Gln Gly Asp Gly Gly Arg Arg
1               5                   10                  15
```

<210> SEQ ID NO 49
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 49

```
Gly Pro Arg Gly Gln Gly Asp Gly Gly Arg Arg Lys Lys Gly Gly
1               5                   10                  15
```

<210> SEQ ID NO 50
<211> LENGTH: 15
<212> TYPE: PRT
<213> ORGANISM: Virus Herpesviridae -continued

```
<220> FEATURE:
<223> OTHER INFORMATION: EBV-protein EBNA1 fragment

<400> SEQUENCE: 50

Gln Gly Asp Gly Gly Arg Arg Lys Lys Gly Gly Trp Phe Gly Lys
1               5                   10                  15

<210> SEQ ID NO 51
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 51

Gly Arg Arg Lys Lys Gly Gly Trp Phe Gly Lys His Arg Gly Gln
1               5                   10                  15

<210> SEQ ID NO 52
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 52

Lys Gly Gly Trp Phe Gly Lys His Arg Gly Gln Gly Gly Ser Asn
1               5                   10                  15

<210> SEQ ID NO 53
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 53

Phe Gly Lys His Arg Gly Gln Gly Gly Ser Asn Pro Lys Phe Glu
1               5                   10                  15

<210> SEQ ID NO 54
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 54

Arg Gly Gln Gly Gly Ser Asn Pro Lys Phe Glu Asn Ile Ala Glu
1               5                   10                  15

<210> SEQ ID NO 55
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 55

Gly Ser Asn Pro Lys Phe Glu Asn Ile Ala Glu Gly Leu Arg Ala
1               5                   10                  15

<210> SEQ ID NO 56
<211> LENGTH: 15
<212> TYPE: PRT
<213> ORGANISM: Virus Herpesviridae
<220> FEATURE:
```

<223> OTHER INFORMATION: EBV-protein EBNA1 fragment

<400> SEQUENCE: 56

Lys Phe Glu Asn Ile Ala Glu Gly Leu Arg Ala Leu Leu Ala Arg
1               5                   10                  15

<210> SEQ ID NO 57
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 57

Ile Ala Glu Gly Leu Arg Ala Leu Leu Ala Arg Ser His Val Glu
1               5                   10                  15

<210> SEQ ID NO 58
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 58

Leu Arg Ala Leu Leu Ala Arg Ser His Val Glu Arg Thr Thr Asp
1               5                   10                  15

<210> SEQ ID NO 59
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 59

Leu Ala Arg Ser His Val Glu Arg Thr Thr Asp Glu Gly Thr Trp
1               5                   10                  15

<210> SEQ ID NO 60
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 60

His Val Glu Arg Thr Thr Asp Glu Gly Thr Trp Val Ala Gly Val
1               5                   10                  15

<210> SEQ ID NO 61
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 61

Thr Thr Asp Glu Gly Thr Trp Val Ala Gly Val Phe Val Tyr Gly
1               5                   10                  15

<210> SEQ ID NO 62
<211> LENGTH: 15
<212> TYPE: PRT
<213> ORGANISM: Virus Herpesviridae
<220> FEATURE:
<223> OTHER INFORMATION: EBV-protein EBNA1 fragment

```
<400> SEQUENCE: 62

Gly Thr Trp Val Ala Gly Val Phe Val Tyr Gly Gly Ser Lys Thr
1               5                   10                  15

<210> SEQ ID NO 63
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 63

Ala Gly Val Phe Val Tyr Gly Gly Ser Lys Thr Ser Leu Tyr Asn
1               5                   10                  15

<210> SEQ ID NO 64
<211> LENGTH: 15
<212> TYPE: PRT
<213> ORGANISM: Virus Herpesviridae
<220> FEATURE:
<223> OTHER INFORMATION: EBV-protein EBNA1 fragment)

<400> SEQUENCE: 64

Val Tyr Gly Gly Ser Lys Thr Ser Leu Tyr Asn Leu Arg Arg Gly
1               5                   10                  15

<210> SEQ ID NO 65
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 65

Ser Lys Thr Ser Leu Tyr Asn Leu Arg Arg Gly Thr Ala Leu Ala
1               5                   10                  15

<210> SEQ ID NO 66
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 66

Leu Tyr Asn Leu Arg Arg Gly Thr Ala Leu Ala Ile Pro Gln Cys
1               5                   10                  15

<210> SEQ ID NO 67
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 67

Arg Arg Gly Thr Ala Leu Ala Ile Pro Gln Cys Arg Leu Thr Pro
1               5                   10                  15

<210> SEQ ID NO 68
<211> LENGTH: 15
<212> TYPE: PRT
<213> ORGANISM: Virus Herpesviridae
<220> FEATURE:
<223> OTHER INFORMATION: EBV-protein EBNA1 fragment
```

```
<400> SEQUENCE: 68

Ala Leu Ala Ile Pro Gln Cys Arg Leu Thr Pro Leu Ser Arg Leu
1               5                   10                  15

<210> SEQ ID NO 69
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 69

Pro Gln Cys Arg Leu Thr Pro Leu Ser Arg Leu Pro Phe Gly Met
1               5                   10                  15

<210> SEQ ID NO 70
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 70

Leu Thr Pro Leu Ser Arg Leu Pro Phe Gly Met Ala Pro Gly Pro
1               5                   10                  15

<210> SEQ ID NO 71
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 71

Ser Arg Leu Pro Phe Gly Met Ala Pro Gly Pro Gly Pro Gln Pro
1               5                   10                  15

<210> SEQ ID NO 72
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 72

Phe Gly Met Ala Pro Gly Pro Gly Pro Gln Pro Gly Pro Leu Arg
1               5                   10                  15

<210> SEQ ID NO 73
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 73

Pro Gly Pro Gly Pro Gln Pro Gly Pro Leu Arg Glu Ser Ile Val
1               5                   10                  15

<210> SEQ ID NO 74
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 74
```

Pro Gln Pro Gly Pro Leu Arg Glu Ser Ile Val Cys Tyr Phe Met
1               5                   10                  15

<210> SEQ ID NO 75
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 75

Pro Leu Arg Glu Ser Ile Val Cys Tyr Phe Met Val Phe Leu Gln
1               5                   10                  15

<210> SEQ ID NO 76
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 76

Ser Ile Val Cys Tyr Phe Met Val Phe Leu Gln Thr His Ile Phe
1               5                   10                  15

<210> SEQ ID NO 77
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 77

Tyr Phe Met Val Phe Leu Gln Thr His Ile Phe Ala Glu Val Leu
1               5                   10                  15

<210> SEQ ID NO 78
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 78

Phe Leu Gln Thr His Ile Phe Ala Glu Val Leu Lys Asp Ala Ile
1               5                   10                  15

<210> SEQ ID NO 79
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 79

His Ile Phe Ala Glu Val Leu Lys Asp Ala Ile Lys Asp Leu Val
1               5                   10                  15

<210> SEQ ID NO 80
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 80

-continued

Glu Val Leu Lys Asp Ala Ile Lys Asp Leu Val Met Thr Lys Pro
1               5                   10                  15

<210> SEQ ID NO 81
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 81

Asp Ala Ile Lys Asp Leu Val Met Thr Lys Pro Ala Pro Thr Cys
1               5                   10                  15

<210> SEQ ID NO 82
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 82

Asp Leu Val Met Thr Lys Pro Ala Pro Thr Cys Asn Ile Arg Val
1               5                   10                  15

<210> SEQ ID NO 83
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 83

Thr Lys Pro Ala Pro Thr Cys Asn Ile Arg Val Thr Val Cys Ser
1               5                   10                  15

<210> SEQ ID NO 84
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 84

Pro Thr Cys Asn Ile Arg Val Thr Val Cys Ser Phe Asp Asp Gly
1               5                   10                  15

<210> SEQ ID NO 85
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 85

Ile Arg Val Thr Val Cys Ser Phe Asp Asp Gly Val Asp Leu Pro
1               5                   10                  15

<210> SEQ ID NO 86
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 86

Val Cys Ser Phe Asp Asp Gly Val Asp Leu Pro Pro Trp Phe Pro

<210> SEQ ID NO 87
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 87

Asp Asp Gly Val Asp Leu Pro Pro Trp Phe Pro Pro Met Val Glu
1               5                   10                  15

<210> SEQ ID NO 88
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 88

Asp Leu Pro Pro Trp Phe Pro Pro Met Val Glu Gly Ala Ala Ala
1               5                   10                  15

<210> SEQ ID NO 89
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 89

Trp Phe Pro Pro Met Val Glu Gly Ala Ala Ala Glu Gly Asp Asp
1               5                   10                  15

<210> SEQ ID NO 90
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 90

Met Val Glu Gly Ala Ala Ala Glu Gly Asp Asp Gly Asp Asp Gly
1               5                   10                  15

<210> SEQ ID NO 91
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 91

Ala Ala Ala Glu Gly Asp Asp Gly Asp Asp Gly Asp Glu Gly Gly
1               5                   10                  15

<210> SEQ ID NO 92
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 92

Gly Asp Asp Gly Asp Asp Gly Asp Glu Gly Gly Asp Gly Asp Glu
1               5                   10                  15

```
<210> SEQ ID NO 93
<211> LENGTH: 15
<212> TYPE: PRT
<213> ORGANISM: Virus Herpesviridae
<220> FEATURE:
<223> OTHER INFORMATION: EBV-protein EBNA1 fragment

<400> SEQUENCE: 93

Asp Asp Gly Asp Glu Gly Gly Asp Gly Asp Glu Gly Glu Glu Gly
1               5                   10                  15

<210> SEQ ID NO 94
<211> LENGTH: 13
<212> TYPE: PRT
<213> ORGANISM: Virus Herpesviridae
<220> FEATURE:
<223> OTHER INFORMATION: EBV-protein EBNA1 fragment

<400> SEQUENCE: 94

Glu Gly Gly Asp Gly Asp Glu Gly Glu Glu Gly Gln Glu
1               5                   10

<210> SEQ ID NO 95
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 95

Met Glu His Asp Leu Glu Arg Gly Pro Pro Gly Pro Arg Arg Pro
1               5                   10                  15

<210> SEQ ID NO 96
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 96

Leu Glu Arg Gly Pro Pro Gly Pro Arg Arg Pro Pro Arg Gly Pro
1               5                   10                  15

<210> SEQ ID NO 97
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 97

Pro Pro Gly Pro Arg Arg Pro Pro Arg Gly Pro Pro Leu Ser Ser
1               5                   10                  15

<210> SEQ ID NO 98
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 98

Arg Arg Pro Pro Arg Gly Pro Pro Leu Ser Ser Ser Leu Gly Leu
1               5                   10                  15
```

<210> SEQ ID NO 99
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 99

Leu Phe Trp Leu Tyr Ile Val Met Ser Asp Trp Thr Gly Gly Ala
1               5                   10                  15

<210> SEQ ID NO 100
<211> LENGTH: 15
<212> TYPE: PRT
<213> ORGANISM: Virus Herpesviridae
<220> FEATURE:
<223> OTHER INFORMATION: EBV - protein LMP1 fragment

<400> SEQUENCE: 100

Tyr Ile Val Met Ser Asp Trp Thr Gly Gly Ala Leu Leu Val Leu
1               5                   10                  15

<210> SEQ ID NO 101
<211> LENGTH: 15
<212> TYPE: PRT
<213> ORGANISM: Virus Herpesviridae
<220> FEATURE:
<223> OTHER INFORMATION: EBV - protein LMP1 fragment

<400> SEQUENCE: 101

Ser Asp Trp Thr Gly Gly Ala Leu Leu Val Leu Tyr Ser Phe Ala
1               5                   10                  15

<210> SEQ ID NO 102
<211> LENGTH: 15
<212> TYPE: PRT
<213> ORGANISM: Virus Herpesviridae
<220> FEATURE:
<223> OTHER INFORMATION: EBV - protein LMP1 fragment

<400> SEQUENCE: 102

Gly Gly Ala Leu Leu Val Leu Tyr Ser Phe Ala Leu Met Leu Ile
1               5                   10                  15

<210> SEQ ID NO 103
<211> LENGTH: 15
<212> TYPE: PRT
<213> ORGANISM: Virus
<220> FEATURE:
<223> OTHER INFORMATION: EBV - protein LMP1

<400> SEQUENCE: 103

Leu Val Leu Tyr Ser Phe Ala Leu Met Leu Ile Ile Ile Ile Leu
1               5                   10                  15

<210> SEQ ID NO 104
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 104

Ser Phe Ala Leu Met Leu Ile Ile Ile Ile Leu Ile Ile Phe Ile
1               5                   10                  15

```
<210> SEQ ID NO 105
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 105

Met Leu Ile Ile Ile Ile Leu Ile Ile Phe Ile Phe Arg Arg Asp
1               5                   10                  15

<210> SEQ ID NO 106
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 106

Ile Ile Leu Ile Ile Phe Ile Phe Arg Arg Asp Leu Leu Cys Pro
1               5                   10                  15

<210> SEQ ID NO 107
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 107

Ile Phe Ile Phe Arg Arg Asp Leu Leu Cys Pro Leu Gly Ala Leu
1               5                   10                  15

<210> SEQ ID NO 108
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 108

Arg Arg Asp Leu Leu Cys Pro Leu Gly Ala Leu Cys Ile Leu Leu
1               5                   10                  15

<210> SEQ ID NO 109
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 109

Leu Cys Pro Leu Gly Ala Leu Cys Ile Leu Leu Leu Met Ile Thr
1               5                   10                  15

<210> SEQ ID NO 110
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 110

Gly Ala Leu Cys Ile Leu Leu Leu Met Ile Thr Leu Leu Leu Ile
1               5                   10                  15

<210> SEQ ID NO 111
```

```
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 111

Ile Leu Leu Leu Met Ile Thr Leu Leu Leu Ile Ala Leu Trp Asn
1               5                   10                  15

<210> SEQ ID NO 112
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 112

Met Ile Thr Leu Leu Leu Ile Ala Leu Trp Asn Leu His Gly Gln
1               5                   10                  15

<210> SEQ ID NO 113
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 113

Leu Leu Ile Ala Leu Trp Asn Leu His Gly Gln Ala Leu Tyr Leu
1               5                   10                  15

<210> SEQ ID NO 114
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 114

Leu Trp Asn Leu His Gly Gln Ala Leu Tyr Leu Gly Ile Val Leu
1               5                   10                  15

<210> SEQ ID NO 115
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 115

His Gly Gln Ala Leu Tyr Leu Gly Ile Val Leu Phe Ile Phe Gly
1               5                   10                  15

<210> SEQ ID NO 116
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 116

Leu Tyr Leu Gly Ile Val Leu Phe Ile Phe Gly Cys Leu Leu Val
1               5                   10                  15

<210> SEQ ID NO 117
<211> LENGTH: 15
```

```
<212> TYPE: PRT
<213> ORGANISM: Virus Herpesviridae
<220> FEATURE:
<223> OTHER INFORMATION: EBV-protein LMP1 fragment

<400> SEQUENCE: 117

Ile Val Leu Phe Ile Phe Gly Cys Leu Leu Val Leu Gly Leu Trp
1               5                   10                  15

<210> SEQ ID NO 118
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 118

Ile Phe Gly Cys Leu Leu Val Leu Gly Leu Trp Ile Tyr Leu Leu
1               5                   10                  15

<210> SEQ ID NO 119
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 119

Leu Leu Val Leu Gly Leu Trp Ile Tyr Leu Leu Glu Ile Leu Trp
1               5                   10                  15

<210> SEQ ID NO 120
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 120

Gly Leu Trp Ile Tyr Leu Leu Glu Ile Leu Trp Arg Leu Gly Ala
1               5                   10                  15

<210> SEQ ID NO 121
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 121

Tyr Leu Leu Glu Ile Leu Trp Arg Leu Gly Ala Thr Ile Trp Gln
1               5                   10                  15

<210> SEQ ID NO 122
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 122

Ile Leu Trp Arg Leu Gly Ala Thr Ile Trp Gln Leu Leu Ala Phe
1               5                   10                  15

<210> SEQ ID NO 123
<211> LENGTH: 15
<212> TYPE: PRT
```

```
<213> ORGANISM: Virus Herpesviridae
<220> FEATURE:
<223> OTHER INFORMATION: EBV-protein LMP1 fragment

<400> SEQUENCE: 123

Leu Gly Ala Thr Ile Trp Gln Leu Leu Ala Phe Phe Leu Ala Phe
1               5                   10                  15

<210> SEQ ID NO 124
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 124

Ile Trp Gln Leu Leu Ala Phe Phe Leu Ala Phe Phe Leu Asp Leu
1               5                   10                  15

<210> SEQ ID NO 125
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 125

Leu Ala Phe Phe Leu Ala Phe Phe Leu Asp Leu Ile Leu Leu Ile
1               5                   10                  15

<210> SEQ ID NO 126
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 126

Leu Ala Phe Phe Leu Asp Leu Ile Leu Leu Ile Ile Ala Leu Tyr
1               5                   10                  15

<210> SEQ ID NO 127
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 127

Leu Asp Leu Ile Leu Leu Ile Ile Ala Leu Tyr Leu Gln Gln Asn
1               5                   10                  15

<210> SEQ ID NO 128
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 128

Leu Leu Ile Ile Ala Leu Tyr Leu Gln Gln Asn Trp Trp Thr Leu
1               5                   10                  15

<210> SEQ ID NO 129
<211> LENGTH: 15
<212> TYPE: PRT
<213> ORGANISM: Virus Herpesviridae
```

<220> FEATURE:
<223> OTHER INFORMATION: EBV-protein LMP1 fragment

<400> SEQUENCE: 129

Ala Leu Tyr Leu Gln Gln Asn Trp Trp Thr Leu Leu Val Asp Leu
1               5                   10                  15

<210> SEQ ID NO 130
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 130

Gln Gln Asn Trp Trp Thr Leu Leu Val Asp Leu Leu Trp Leu Leu
1               5                   10                  15

<210> SEQ ID NO 131
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 131

Trp Thr Leu Leu Val Asp Leu Leu Trp Leu Leu Leu Phe Leu Ala
1               5                   10                  15

<210> SEQ ID NO 132
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 132

Val Asp Leu Leu Trp Leu Leu Leu Phe Leu Ala Ile Leu Ile Trp
1               5                   10                  15

<210> SEQ ID NO 133
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 133

Trp Leu Leu Leu Phe Leu Ala Ile Leu Ile Trp Met Tyr Tyr His
1               5                   10                  15

<210> SEQ ID NO 134
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 134

Phe Leu Ala Ile Leu Ile Trp Met Tyr Tyr His Gly Gln Arg His
1               5                   10                  15

<210> SEQ ID NO 135
<211> LENGTH: 15
<212> TYPE: PRT
<213> ORGANISM: Virus Herpesviridae
<220> FEATURE:

-continued

<223> OTHER INFORMATION: EBV-protein LMP1 fragment

<400> SEQUENCE: 135

Leu Ile Trp Met Tyr Tyr His Gly Gln Arg His Ser Asp Glu His
1               5                   10                  15

<210> SEQ ID NO 136
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 136

Tyr Tyr His Gly Gln Arg His Ser Asp Glu His His His Asp Asp
1               5                   10                  15

<210> SEQ ID NO 137
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 137

Gln Arg His Ser Asp Glu His His His Asp Asp Ser Leu Pro His
1               5                   10                  15

<210> SEQ ID NO 138
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 138

Asp Glu His His His Asp Asp Ser Leu Pro His Pro Gln Gln Ala
1               5                   10                  15

<210> SEQ ID NO 139
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 139

His Asp Asp Ser Leu Pro His Pro Gln Gln Ala Thr Asp Asp Ser
1               5                   10                  15

<210> SEQ ID NO 140
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 140

Leu Pro His Pro Gln Gln Ala Thr Asp Asp Ser Gly His Glu Ser
1               5                   10                  15

<210> SEQ ID NO 141
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 141

Gln Gln Ala Thr Asp Asp Ser Gly His Glu Ser Asp Ser Asn Ser
1               5                   10                  15

<210> SEQ ID NO 142
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 142

Asp Asp Ser Gly His Glu Ser Asp Ser Asn Ser Asn Glu Gly Arg
1               5                   10                  15

<210> SEQ ID NO 143
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 143

His Glu Ser Asp Ser Asn Ser Asn Glu Gly Arg His His Leu Leu
1               5                   10                  15

<210> SEQ ID NO 144
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 144

Ser Asn Ser Asn Glu Gly Arg His His Leu Leu Val Ser Gly Ala
1               5                   10                  15

<210> SEQ ID NO 145
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 145

Glu Gly Arg His His Leu Leu Val Ser Gly Ala Gly Asp Gly Pro
1               5                   10                  15

<210> SEQ ID NO 146
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 146

His Leu Leu Val Ser Gly Ala Gly Asp Gly Pro Pro Leu Cys Ser
1               5                   10                  15

<210> SEQ ID NO 147
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 147

Ser Gly Ala Gly Asp Gly Pro Pro Leu Cys Ser Gln Asn Leu Gly
1               5                   10                  15

<210> SEQ ID NO 148
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 148

Asp Gly Pro Pro Leu Cys Ser Gln Asn Leu Gly Ala Pro Gly Gly
1               5                   10                  15

<210> SEQ ID NO 149
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 149

Leu Cys Ser Gln Asn Leu Gly Ala Pro Gly Gly Gly Pro Asp Asn
1               5                   10                  15

<210> SEQ ID NO 150
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 150

Asn Leu Gly Ala Pro Gly Gly Gly Pro Asp Asn Gly Pro Gln Asp
1               5                   10                  15

<210> SEQ ID NO 151
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 151

Pro Gly Gly Gly Pro Asp Asn Gly Pro Gln Asp Pro Asp Asn Thr
1               5                   10                  15

<210> SEQ ID NO 152
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 152

Pro Asp Asn Gly Pro Gln Asp Pro Asp Asn Thr Asp Asp Asn Gly
1               5                   10                  15

<210> SEQ ID NO 153
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 153

```
Pro Gln Asp Pro Asp Asn Thr Asp Asp Asn Gly Pro Gln Asp Pro
1               5                   10                  15

<210> SEQ ID NO 154
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 154

Asp Asn Thr Asp Asp Asn Gly Pro Gln Asp Pro Asp Asn Thr Asp
1               5                   10                  15

<210> SEQ ID NO 155
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 155

Asp Asn Gly Pro Gln Asp Pro Asp Asn Thr Asp Asp Asn Gly Pro
1               5                   10                  15

<210> SEQ ID NO 156
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 156

Gln Asp Pro Asp Asn Thr Asp Asp Asn Gly Pro His Asp Pro Leu
1               5                   10                  15

<210> SEQ ID NO 157
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 157

Asn Thr Asp Asp Asn Gly Pro His Asp Pro Leu Pro His Ser Pro
1               5                   10                  15

<210> SEQ ID NO 158
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 158

Asn Gly Pro His Asp Pro Leu Pro His Ser Pro Ser Asp Ser Ala
1               5                   10                  15

<210> SEQ ID NO 159
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 159
```

```
Asp Pro Leu Pro His Ser Pro Ser Asp Ser Ala Gly Asn Asp Gly
1               5                   10                  15

<210> SEQ ID NO 160
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 160

His Ser Pro Ser Asp Ser Ala Gly Asn Asp Gly Gly Pro Pro Gln
1               5                   10                  15

<210> SEQ ID NO 161
<211> LENGTH: 15
<212> TYPE: PRT
<213> ORGANISM: Virus Herpesviridae
<220> FEATURE:
<223> OTHER INFORMATION: EBV - protein LMP1 fragment

<400> SEQUENCE: 161

Asp Ser Ala Gly Asn Asp Gly Gly Pro Pro Gln Leu Thr Glu Glu
1               5                   10                  15

<210> SEQ ID NO 162
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 162

Asn Asp Gly Gly Pro Pro Gln Leu Thr Glu Glu Val Glu Asn Lys
1               5                   10                  15

<210> SEQ ID NO 163
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 163

Pro Pro Gln Leu Thr Glu Glu Val Glu Asn Lys Gly Gly Asp Gln
1               5                   10                  15

<210> SEQ ID NO 164
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 164

Thr Glu Glu Val Glu Asn Lys Gly Gly Asp Gln Gly Pro Pro Leu
1               5                   10                  15

<210> SEQ ID NO 165
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 165

Glu Asn Lys Gly Gly Asp Gln Gly Pro Pro Leu Met Thr Asp Gly
```

<210> SEQ ID NO 166
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 166

Gly Asp Gln Gly Pro Pro Leu Met Thr Asp Gly Gly Gly His
1               5                   10                  15

<210> SEQ ID NO 167
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 167

Pro Pro Leu Met Thr Asp Gly Gly Gly Gly His Ser His Asp Ser
1               5                   10                  15

<210> SEQ ID NO 168
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 168

Thr Asp Gly Gly Gly Gly His Ser His Asp Ser Gly His Gly Gly
1               5                   10                  15

<210> SEQ ID NO 169
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 169

Gly Gly His Ser His Asp Ser Gly His Gly Gly Asp Pro His
1               5                   10                  15

<210> SEQ ID NO 170
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 170

His Asp Ser Gly His Gly Gly Gly Asp Pro His Leu Pro Thr Leu
1               5                   10                  15

<210> SEQ ID NO 171
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 171

His Gly Gly Gly Asp Pro His Leu Pro Thr Leu Leu Leu Gly Ser
1               5                   10                  15

```
<210> SEQ ID NO 172
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 172

Asp Pro His Leu Pro Thr Leu Leu Leu Gly Ser Ser Gly Ser Gly
1               5                   10                  15

<210> SEQ ID NO 173
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 173

Pro Thr Leu Leu Leu Gly Ser Ser Gly Ser Gly Gly Asp Asp Asp
1               5                   10                  15

<210> SEQ ID NO 174
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 174

Leu Gly Ser Ser Gly Ser Gly Gly Asp Asp Asp Asp Pro His Gly
1               5                   10                  15

<210> SEQ ID NO 175
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 175

Gly Ser Gly Gly Asp Asp Asp Asp Pro His Gly Pro Val Gln Leu
1               5                   10                  15

<210> SEQ ID NO 176
<211> LENGTH: 15
<212> TYPE: PRT
<213> ORGANISM: Virus Herpesviridae
<220> FEATURE:
<223> OTHER INFORMATION: EBV-protein LMP1 fragment

<400> SEQUENCE: 176

Asp Asp Asp Asp Pro His Gly Pro Val Gln Leu Ser Tyr Tyr Asp
1               5                   10                  15

<210> SEQ ID NO 177
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 177

Met Gly Ser Leu Glu Met Val Pro Met Gly Ala Gly Pro Pro Ser
1               5                   10                  15
```

<210> SEQ ID NO 178
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 178

Glu Met Val Pro Met Gly Ala Gly Pro Pro Ser Pro Gly Gly Asp
1               5                   10                  15

<210> SEQ ID NO 179
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 179

Met Gly Ala Gly Pro Pro Ser Pro Gly Gly Asp Pro Asp Gly Tyr
1               5                   10                  15

<210> SEQ ID NO 180
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 180

Pro Pro Ser Pro Gly Gly Asp Pro Asp Gly Tyr Asp Gly Gly Asn
1               5                   10                  15

<210> SEQ ID NO 181
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 181

Gly Gly Asp Pro Asp Gly Tyr Asp Gly Gly Asn Asn Ser Gln Tyr
1               5                   10                  15

<210> SEQ ID NO 182
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 182

Asp Gly Tyr Asp Gly Gly Asn Asn Ser Gln Tyr Pro Ser Ala Ser
1               5                   10                  15

<210> SEQ ID NO 183
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 183

Gly Gly Asn Asn Ser Gln Tyr Pro Ser Ala Ser Gly Ser Ser Gly
1               5                   10                  15

<210> SEQ ID NO 184
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 184

Ser Gln Tyr Pro Ser Ala Ser Gly Ser Ser Gly Asn Thr Pro Thr
1               5                   10                  15

<210> SEQ ID NO 185
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 185

Ser Ala Ser Gly Ser Ser Gly Asn Thr Pro Thr Pro Pro Asn Asp
1               5                   10                  15

<210> SEQ ID NO 186
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 186

Ser Ser Gly Asn Thr Pro Thr Pro Pro Asn Asp Glu Glu Arg Glu
1               5                   10                  15

<210> SEQ ID NO 187
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 187

Thr Pro Thr Pro Pro Asn Asp Glu Glu Arg Glu Ser Asn Glu Glu
1               5                   10                  15

<210> SEQ ID NO 188
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 188

Pro Asn Asp Glu Glu Arg Glu Ser Asn Glu Glu Pro Pro Pro Pro
1               5                   10                  15

<210> SEQ ID NO 189
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 189

Glu Arg Glu Ser Asn Glu Glu Pro Pro Pro Pro Tyr Glu Asp Pro
1               5                   10                  15

<210> SEQ ID NO 190

```
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 190

Asn Glu Glu Pro Pro Pro Tyr Glu Asp Pro Tyr Trp Gly Asn
1               5                   10                  15

<210> SEQ ID NO 191
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 191

Pro Pro Pro Tyr Glu Asp Pro Tyr Trp Gly Asn Gly Asp Arg His
1               5                   10                  15

<210> SEQ ID NO 192
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 192

Glu Asp Pro Tyr Trp Gly Asn Gly Asp Arg His Ser Asp Tyr Gln
1               5                   10                  15

<210> SEQ ID NO 193
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 193

Trp Gly Asn Gly Asp Arg His Ser Asp Tyr Gln Pro Leu Gly Thr
1               5                   10                  15

<210> SEQ ID NO 194
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 194

Asp Arg His Ser Asp Tyr Gln Pro Leu Gly Thr Gln Asp Gln Ser
1               5                   10                  15

<210> SEQ ID NO 195
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 195

Asp Tyr Gln Pro Leu Gly Thr Gln Asp Gln Ser Leu Tyr Leu Gly
1               5                   10                  15

<210> SEQ ID NO 196
<211> LENGTH: 15
```

```
<212> TYPE: PRT
<213> ORGANISM: Virus Herpesviridae
<220> FEATURE:
<223> OTHER INFORMATION: EBV-protein LMP2 fragment

<400> SEQUENCE: 196

Leu Gly Thr Gln Asp Gln Ser Leu Tyr Leu Gly Leu Gln His Asp
1               5                   10                  15

<210> SEQ ID NO 197
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 197

Asp Gln Ser Leu Tyr Leu Gly Leu Gln His Asp Gly Asn Asp Gly
1               5                   10                  15

<210> SEQ ID NO 198
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 198

Tyr Leu Gly Leu Gln His Asp Gly Asn Asp Gly Leu Pro Pro Pro
1               5                   10                  15

<210> SEQ ID NO 199
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 199

Gln His Asp Gly Asn Asp Gly Leu Pro Pro Pro Pro Tyr Ser Pro
1               5                   10                  15

<210> SEQ ID NO 200
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 200

Asn Asp Gly Leu Pro Pro Pro Pro Tyr Ser Pro Arg Asp Asp Ser
1               5                   10                  15

<210> SEQ ID NO 201
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 201

Pro Pro Pro Pro Tyr Ser Pro Arg Asp Asp Ser Ser Gln His Ile
1               5                   10                  15

<210> SEQ ID NO 202
<211> LENGTH: 15
<212> TYPE: PRT
```

<213> ORGANISM: Virus Herpesviridae
<220> FEATURE:
<223> OTHER INFORMATION: EBV-protein LMP2 fragment

<400> SEQUENCE: 202

Tyr Ser Pro Arg Asp Asp Ser Ser Gln His Ile Tyr Glu Glu Ala
1               5                   10                  15

<210> SEQ ID NO 203
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 203

Asp Asp Ser Ser Gln His Ile Tyr Glu Glu Ala Gly Arg Gly Ser
1               5                   10                  15

<210> SEQ ID NO 204
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 204

Gln His Ile Tyr Glu Glu Ala Gly Arg Gly Ser Met Asn Pro Val
1               5                   10                  15

<210> SEQ ID NO 205
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 205

Glu Glu Ala Gly Arg Gly Ser Met Asn Pro Val Cys Leu Pro Val
1               5                   10                  15

<210> SEQ ID NO 206
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 206

Arg Gly Ser Met Asn Pro Val Cys Leu Pro Val Ile Val Ala Pro
1               5                   10                  15

<210> SEQ ID NO 207
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 207

Asn Pro Val Cys Leu Pro Val Ile Val Ala Pro Tyr Leu Phe Trp
1               5                   10                  15

<210> SEQ ID NO 208
<211> LENGTH: 15
<212> TYPE: PRT
<213> ORGANISM: Virus Herpesviridae -continued

```
<220> FEATURE:
<223> OTHER INFORMATION: EBV-protein LMP2 fragment

<400> SEQUENCE: 208

Leu Pro Val Ile Val Ala Pro Tyr Leu Phe Trp Leu Ala Ala Ile
1               5                   10                  15

<210> SEQ ID NO 209
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 209

Val Ala Pro Tyr Leu Phe Trp Leu Ala Ala Ile Ala Ala Ser Cys
1               5                   10                  15

<210> SEQ ID NO 210
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 210

Leu Phe Trp Leu Ala Ala Ile Ala Ala Ser Cys Phe Thr Ala Ser
1               5                   10                  15

<210> SEQ ID NO 211
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 211

Ala Ala Ile Ala Ala Ser Cys Phe Thr Ala Ser Val Ser Thr Val
1               5                   10                  15

<210> SEQ ID NO 212
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 212

Ala Ser Cys Phe Thr Ala Ser Val Ser Thr Val Val Thr Ala Thr
1               5                   10                  15

<210> SEQ ID NO 213
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 213

Thr Ala Ser Val Ser Thr Val Val Thr Ala Thr Gly Leu Ala Leu
1               5                   10                  15

<210> SEQ ID NO 214
<211> LENGTH: 15
<212> TYPE: PRT
<213> ORGANISM: Virus Herpesviridae
<220> FEATURE:
```

<223> OTHER INFORMATION: EBV-protein LMP2 fragment

<400> SEQUENCE: 214

Ser Thr Val Val Thr Ala Thr Gly Leu Ala Leu Ser Leu Leu Leu
1               5                   10                  15

<210> SEQ ID NO 215
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 215

Thr Ala Thr Gly Leu Ala Leu Ser Leu Leu Leu Leu Ala Ala Val
1               5                   10                  15

<210> SEQ ID NO 216
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 216

Leu Ala Leu Ser Leu Leu Leu Ala Ala Val Ala Ser Ser Tyr
1               5                   10                  15

<210> SEQ ID NO 217
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 217

Leu Leu Leu Leu Ala Ala Val Ala Ser Ser Tyr Ala Ala Ala Gln
1               5                   10                  15

<210> SEQ ID NO 218
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 218

Ala Ala Val Ala Ser Ser Tyr Ala Ala Ala Gln Arg Lys Leu Leu
1               5                   10                  15

<210> SEQ ID NO 219
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 219

Ser Ser Tyr Ala Ala Ala Gln Arg Lys Leu Leu Thr Pro Val Thr
1               5                   10                  15

<210> SEQ ID NO 220
<211> LENGTH: 15
<212> TYPE: PRT
<213> ORGANISM: Virus Herpesviridae
<220> FEATURE:
<223> OTHER INFORMATION: EBV-protein LMP2 fragment

```
<400> SEQUENCE: 220

Ala Ala Gln Arg Lys Leu Leu Thr Pro Val Thr Val Leu Thr Ala
1               5                   10                  15

<210> SEQ ID NO 221
<211> LENGTH: 15
<212> TYPE: PRT
<213> ORGANISM: Virus Herpesviridae
<220> FEATURE:
<223> OTHER INFORMATION: EBV - protein LMP2 fragment

<400> SEQUENCE: 221

Lys Leu Leu Thr Pro Val Thr Val Leu Thr Ala Val Val Thr Phe
1               5                   10                  15

<210> SEQ ID NO 222
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 222

Pro Val Thr Val Leu Thr Ala Val Val Thr Phe Phe Ala Ile Cys
1               5                   10                  15

<210> SEQ ID NO 223
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 223

Leu Thr Ala Val Val Thr Phe Phe Ala Ile Cys Leu Thr Trp Arg
1               5                   10                  15

<210> SEQ ID NO 224
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 224

Val Thr Phe Phe Ala Ile Cys Leu Thr Trp Arg Ile Glu Asp Pro
1               5                   10                  15

<210> SEQ ID NO 225
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 225

Ala Ile Cys Leu Thr Trp Arg Ile Glu Asp Pro Pro Phe Asn Ser
1               5                   10                  15

<210> SEQ ID NO 226
<211> LENGTH: 15
<212> TYPE: PRT
<213> ORGANISM: Virus Herpesviridae
<220> FEATURE:
<223> OTHER INFORMATION: EBV-protein LMP2 fragment
```

```
<400> SEQUENCE: 226

Thr Trp Arg Ile Glu Asp Pro Pro Phe Asn Ser Leu Leu Phe Ala
1               5                   10                  15

<210> SEQ ID NO 227
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 227

Glu Asp Pro Pro Phe Asn Ser Leu Leu Phe Ala Leu Leu Ala Ala
1               5                   10                  15

<210> SEQ ID NO 228
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 228

Phe Asn Ser Leu Leu Phe Ala Leu Leu Ala Ala Ala Gly Gly Leu
1               5                   10                  15

<210> SEQ ID NO 229
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 229

Leu Phe Ala Leu Leu Ala Ala Ala Gly Gly Leu Gln Gly Ile Tyr
1               5                   10                  15

<210> SEQ ID NO 230
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 230

Leu Ala Ala Ala Gly Gly Leu Gln Gly Ile Tyr Val Leu Val Met
1               5                   10                  15

<210> SEQ ID NO 231
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 231

Gly Gly Leu Gln Gly Ile Tyr Val Leu Val Met Leu Val Leu Leu
1               5                   10                  15

<210> SEQ ID NO 232
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 232
```

Gly Ile Tyr Val Leu Val Met Leu Val Leu Leu Ile Leu Ala Tyr
1               5                   10                  15

<210> SEQ ID NO 233
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 233

Leu Val Met Leu Val Leu Leu Ile Leu Ala Tyr Arg Arg Arg Trp
1               5                   10                  15

<210> SEQ ID NO 234
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 234

Val Leu Leu Ile Leu Ala Tyr Arg Arg Arg Trp Arg Arg Leu Thr
1               5                   10                  15

<210> SEQ ID NO 235
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 235

Leu Ala Tyr Arg Arg Arg Trp Arg Arg Leu Thr Val Cys Gly Gly
1               5                   10                  15

<210> SEQ ID NO 236
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 236

Arg Arg Trp Arg Arg Leu Thr Val Cys Gly Gly Ile Met Phe Leu
1               5                   10                  15

<210> SEQ ID NO 237
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 237

Arg Leu Thr Val Cys Gly Gly Ile Met Phe Leu Ala Cys Val Leu
1               5                   10                  15

<210> SEQ ID NO 238
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 238

-continued

Cys Gly Gly Ile Met Phe Leu Ala Cys Val Leu Val Leu Ile Val
1               5                   10                  15

<210> SEQ ID NO 239
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 239

Met Phe Leu Ala Cys Val Leu Val Leu Ile Val Asp Ala Val Leu
1               5                   10                  15

<210> SEQ ID NO 240
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 240

Cys Val Leu Val Leu Ile Val Asp Ala Val Leu Gln Leu Ser Pro
1               5                   10                  15

<210> SEQ ID NO 241
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 241

Leu Ile Val Asp Ala Val Leu Gln Leu Ser Pro Leu Leu Gly Ala
1               5                   10                  15

<210> SEQ ID NO 242
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 242

Ala Val Leu Gln Leu Ser Pro Leu Leu Gly Ala Val Thr Val Val
1               5                   10                  15

<210> SEQ ID NO 243
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 243

Leu Ser Pro Leu Leu Gly Ala Val Thr Val Val Ser Met Thr Leu
1               5                   10                  15

<210> SEQ ID NO 244
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 244

Leu Gly Ala Val Thr Val Val Ser Met Thr Leu Leu Leu Leu Ala

<210> SEQ ID NO 245
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 245

Thr Val Val Ser Met Thr Leu Leu Leu Ala Phe Val Leu Trp
1               5                   10                  15

<210> SEQ ID NO 246
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 246

Met Thr Leu Leu Leu Leu Ala Phe Val Leu Trp Leu Ser Ser Pro
1               5                   10                  15

<210> SEQ ID NO 247
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 247

Leu Leu Ala Phe Val Leu Trp Leu Ser Ser Pro Gly Gly Leu Gly
1               5                   10                  15

<210> SEQ ID NO 248
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 248

Val Leu Trp Leu Ser Ser Pro Gly Gly Leu Gly Thr Leu Gly Ala
1               5                   10                  15

<210> SEQ ID NO 249
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 249

Ser Ser Pro Gly Gly Leu Gly Thr Leu Gly Ala Ala Leu Leu Thr
1               5                   10                  15

<210> SEQ ID NO 250
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 250

Gly Leu Gly Thr Leu Gly Ala Ala Leu Leu Thr Leu Ala Ala Ala
1               5                   10                  15

<210> SEQ ID NO 251
<211> LENGTH: 15
<212> TYPE: PRT
<213> ORGANISM: Virus Herpesviridae
<220> FEATURE:
<223> OTHER INFORMATION: EBV - protein LMP2 fragment

<400> SEQUENCE: 251

```
Leu Gly Ala Ala Leu Leu Thr Leu Ala Ala Ala Leu Ala Leu Leu
1               5                   10                  15
```

<210> SEQ ID NO 252
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 252

```
Leu Leu Thr Leu Ala Ala Ala Leu Ala Leu Leu Ala Ser Leu Ile
1               5                   10                  15
```

<210> SEQ ID NO 253
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 253

```
Ala Ala Ala Leu Ala Leu Leu Ala Ser Leu Ile Leu Gly Thr Leu
1               5                   10                  15
```

<210> SEQ ID NO 254
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 254

```
Ala Leu Leu Ala Ser Leu Ile Leu Gly Thr Leu Asn Leu Thr Thr
1               5                   10                  15
```

<210> SEQ ID NO 255
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 255

```
Ser Leu Ile Leu Gly Thr Leu Asn Leu Thr Thr Met Phe Leu Leu
1               5                   10                  15
```

<210> SEQ ID NO 256
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 256

```
Gly Thr Leu Asn Leu Thr Thr Met Phe Leu Leu Met Leu Leu Trp
1               5                   10                  15
```

<210> SEQ ID NO 257
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 257

Leu Thr Thr Met Phe Leu Leu Met Leu Leu Trp Thr Leu Val Val
1               5                   10                  15

<210> SEQ ID NO 258
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 258

Phe Leu Leu Met Leu Leu Trp Thr Leu Val Val Leu Leu Ile Cys
1               5                   10                  15

<210> SEQ ID NO 259
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 259

Leu Leu Trp Thr Leu Val Val Leu Leu Ile Cys Ser Ser Cys Ser
1               5                   10                  15

<210> SEQ ID NO 260
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 260

Leu Val Val Leu Leu Ile Cys Ser Ser Cys Ser Ser Cys Pro Leu
1               5                   10                  15

<210> SEQ ID NO 261
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 261

Leu Ile Cys Ser Ser Cys Ser Ser Cys Pro Leu Ser Lys Ile Leu
1               5                   10                  15

<210> SEQ ID NO 262
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 262

Ser Cys Ser Ser Cys Pro Leu Ser Lys Ile Leu Leu Ala Arg Leu
1               5                   10                  15

```
<210> SEQ ID NO 263
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 263

Cys Pro Leu Ser Lys Ile Leu Leu Ala Arg Leu Phe Leu Tyr Ala
1               5                   10                  15

<210> SEQ ID NO 264
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 264

Lys Ile Leu Leu Ala Arg Leu Phe Leu Tyr Ala Leu Ala Leu Leu
1               5                   10                  15

<210> SEQ ID NO 265
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 265

Ala Arg Leu Phe Leu Tyr Ala Leu Ala Leu Leu Leu Leu Ala Ser
1               5                   10                  15

<210> SEQ ID NO 266
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 266

Leu Tyr Ala Leu Ala Leu Leu Leu Leu Ala Ser Ala Leu Ile Ala
1               5                   10                  15

<210> SEQ ID NO 267
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 267

Ala Leu Leu Leu Leu Ala Ser Ala Leu Ile Ala Gly Gly Ser Ile
1               5                   10                  15

<210> SEQ ID NO 268
<211> LENGTH: 15
<212> TYPE: PRT
<213> ORGANISM: Virus
<220> FEATURE:
<223> OTHER INFORMATION: EBV - protein LMP2

<400> SEQUENCE: 268

Leu Ala Ser Ala Leu Ile Ala Gly Gly Ser Ile Leu Gln Thr Asn
1               5                   10                  15

<210> SEQ ID NO 269
```

```
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 269

Leu Ile Ala Gly Gly Ser Ile Leu Gln Thr Asn Phe Lys Ser Leu
1               5                   10                  15

<210> SEQ ID NO 270
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 270

Gly Ser Ile Leu Gln Thr Asn Phe Lys Ser Leu Ser Ser Thr Glu
1               5                   10                  15

<210> SEQ ID NO 271
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 271

Gln Thr Asn Phe Lys Ser Leu Ser Ser Thr Glu Phe Ile Pro Asn
1               5                   10                  15

<210> SEQ ID NO 272
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 272

Lys Ser Leu Ser Ser Thr Glu Phe Ile Pro Asn Leu Phe Cys Met
1               5                   10                  15

<210> SEQ ID NO 273
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 273

Ser Thr Glu Phe Ile Pro Asn Leu Phe Cys Met Leu Leu Leu Ile
1               5                   10                  15

<210> SEQ ID NO 274
<211> LENGTH: 15
<212> TYPE: PRT
<213> ORGANISM: Virus Herpesviridae
<220> FEATURE:
     <223   EBV-protein LMP2 fragment

<400> SEQUENCE: 274

Ile Pro Asn Leu Phe Cys Met Leu Leu Leu Ile Val Ala Gly Ile
1               5                   10                  15

<210> SEQ ID NO 275
<211> LENGTH: 15
```

-continued

```
<212> TYPE: PRT
<213> ORGANISM: Virus Herpesviridae
<220> FEATURE:
<223> OTHER INFORMATION: EBV-protein LMP2 fragment

<400> SEQUENCE: 275

Phe Cys Met Leu Leu Leu Ile Val Ala Gly Ile Leu Phe Ile Leu
1               5                   10                  15

<210> SEQ ID NO 276
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 276

Leu Leu Ile Val Ala Gly Ile Leu Phe Ile Leu Ala Ile Leu Thr
1               5                   10                  15

<210> SEQ ID NO 277
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 277

Ala Gly Ile Leu Phe Ile Leu Ala Ile Leu Thr Glu Trp Gly Ser
1               5                   10                  15

<210> SEQ ID NO 278
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 278

Phe Ile Leu Ala Ile Leu Thr Glu Trp Gly Ser Gly Asn Arg Thr
1               5                   10                  15

<210> SEQ ID NO 279
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 279

Ile Leu Thr Glu Trp Gly Ser Gly Asn Arg Thr Tyr Gly Pro Val
1               5                   10                  15

<210> SEQ ID NO 280
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 280

Trp Gly Ser Gly Asn Arg Thr Tyr Gly Pro Val Phe Met Cys Leu
1               5                   10                  15

<210> SEQ ID NO 281
<211> LENGTH: 15
<212> TYPE: PRT
```

<213> ORGANISM: Virus Herpesviridae
<220> FEATURE:
<223> OTHER INFORMATION: EBV-protein LMP2 fragment

<400> SEQUENCE: 281

Asn Arg Thr Tyr Gly Pro Val Phe Met Cys Leu Gly Gly Leu Leu
1               5                   10                  15

<210> SEQ ID NO 282
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 282

Gly Pro Val Phe Met Cys Leu Gly Gly Leu Leu Thr Met Val Ala
1               5                   10                  15

<210> SEQ ID NO 283
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 283

Met Cys Leu Gly Gly Leu Leu Thr Met Val Ala Gly Ala Val Trp
1               5                   10                  15

<210> SEQ ID NO 284
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 284

Gly Leu Leu Thr Met Val Ala Gly Ala Val Trp Leu Thr Val Met
1               5                   10                  15

<210> SEQ ID NO 285
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 285

Met Val Ala Gly Ala Val Trp Leu Thr Val Met Ser Asn Thr Leu
1               5                   10                  15

<210> SEQ ID NO 286
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 286

Ala Val Trp Leu Thr Val Met Ser Asn Thr Leu Leu Ser Ala Trp
1               5                   10                  15

<210> SEQ ID NO 287
<211> LENGTH: 15
<212> TYPE: PRT
<213> ORGANISM: Virus Herpesviridae

```
<220> FEATURE:
<223> OTHER INFORMATION: EBV-protein LMP2 fragment

<400> SEQUENCE: 287

Thr Val Met Ser Asn Thr Leu Leu Ser Ala Trp Ile Leu Thr Ala
1               5                   10                  15

<210> SEQ ID NO 288
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 288

Asn Thr Leu Leu Ser Ala Trp Ile Leu Thr Ala Gly Phe Leu Ile
1               5                   10                  15

<210> SEQ ID NO 289
<211> LENGTH: 15
<212> TYPE: PRT
<213> ORGANISM: Virus Herpesviridae
<220> FEATURE:
<223> OTHER INFORMATION: EBV-protein LMP2 fragments

<400> SEQUENCE: 289

Ser Ala Trp Ile Leu Thr Ala Gly Phe Leu Ile Phe Leu Ile Gly
1               5                   10                  15

<210> SEQ ID NO 290
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 290

Leu Thr Ala Gly Phe Leu Ile Phe Leu Ile Gly Phe Ala Leu Phe
1               5                   10                  15

<210> SEQ ID NO 291
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 291

Phe Leu Ile Phe Leu Ile Gly Phe Ala Leu Phe Gly Val Ile Arg
1               5                   10                  15

<210> SEQ ID NO 292
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 292

Leu Ile Gly Phe Ala Leu Phe Gly Val Ile Arg Cys Cys Arg Tyr
1               5                   10                  15

<210> SEQ ID NO 293
<211> LENGTH: 15
<212> TYPE: PRT
<213> ORGANISM: Virus Herpesviridae
<220> FEATURE:
```

```
<223> OTHER INFORMATION: EBV-protein LMP2 fragment

<400> SEQUENCE: 293

Ala Leu Phe Gly Val Ile Arg Cys Cys Arg Tyr Cys Cys Tyr Tyr
1               5                   10                  15

<210> SEQ ID NO 294
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 294

Val Ile Arg Cys Cys Arg Tyr Cys Cys Tyr Tyr Cys Leu Thr Leu
1               5                   10                  15

<210> SEQ ID NO 295
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 295

Cys Arg Tyr Cys Cys Tyr Tyr Cys Leu Thr Leu Glu Ser Glu Glu
1               5                   10                  15

<210> SEQ ID NO 296
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 296

Cys Tyr Tyr Cys Leu Thr Leu Glu Ser Glu Glu Arg Pro Pro Thr
1               5                   10                  15

<210> SEQ ID NO 297
<211> LENGTH: 15
<212> TYPE: PRT
<213> ORGANISM: Virus Herpesviridae
<220> FEATURE:
<223> OTHER INFORMATION: EBV-protein LMP2 fragment

<400> SEQUENCE: 297

Leu Thr Leu Glu Ser Glu Glu Arg Pro Pro Thr Pro Tyr Arg Asn
1               5                   10                  15

<210> SEQ ID NO 298
<211> LENGTH: 13
<212> TYPE: PRT
<213> ORGANISM: Virus Herpesviridae
<220> FEATURE:
<223> OTHER INFORMATION: EBV-protein LMP2 fragment

<400> SEQUENCE: 298

Ser Glu Glu Arg Pro Pro Thr Pro Tyr Arg Asn Thr Val
1               5                   10

<210> SEQ ID NO 299
<211> LENGTH: 15
<212> TYPE: PRT
<213> ORGANISM: Virus Herpesviridae
<220> FEATURE:
<223> OTHER INFORMATION: EBV-protein BARF 1 fragment
```

<400> SEQUENCE: 299

Met Ala Arg Phe Ile Ala Gln Leu Leu Leu Ala Ser Cys Val
1               5                   10                  15

<210> SEQ ID NO 300
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 300

Ala Gln Leu Leu Leu Leu Ala Ser Cys Val Ala Ala Gly Gln Ala
1               5                   10                  15

<210> SEQ ID NO 301
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 301

Leu Ala Ser Cys Val Ala Ala Gly Gln Ala Val Thr Ala Phe Leu
1               5                   10                  15

<210> SEQ ID NO 302
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 302

Ala Ala Gly Gln Ala Val Thr Ala Phe Leu Gly Glu Arg Val Thr
1               5                   10                  15

<210> SEQ ID NO 303
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 303

Val Thr Ala Phe Leu Gly Glu Arg Val Thr Leu Thr Ser Tyr Trp
1               5                   10                  15

<210> SEQ ID NO 304
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 304

Gly Glu Arg Val Thr Leu Thr Ser Tyr Trp Arg Arg Val Ser Leu
1               5                   10                  15

<210> SEQ ID NO 305
<211> LENGTH: 15
<212> TYPE: PRT
<213> ORGANISM: Virus
<220> FEATURE:
<223> OTHER INFORMATION: EBV - protein BARF 1

```
<400> SEQUENCE: 305

Leu Thr Ser Tyr Trp Arg Arg Val Ser Leu Gly Pro Glu Ile Glu
1               5                   10                  15

<210> SEQ ID NO 306
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 306

Arg Arg Val Ser Leu Gly Pro Glu Ile Glu Val Ser Trp Phe Lys
1               5                   10                  15

<210> SEQ ID NO 307
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 307

Gly Pro Glu Ile Glu Val Ser Trp Phe Lys Leu Gly Pro Gly Glu
1               5                   10                  15

<210> SEQ ID NO 308
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 308

Val Ser Trp Phe Lys Leu Gly Pro Gly Glu Glu Gln Val Leu Ile
1               5                   10                  15

<210> SEQ ID NO 309
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 309

Leu Gly Pro Gly Glu Glu Gln Val Leu Ile Gly Arg Met His His
1               5                   10                  15

<210> SEQ ID NO 310
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 310

Glu Gln Val Leu Ile Gly Arg Met His His Asp Val Ile Phe Ile
1               5                   10                  15

<210> SEQ ID NO 311
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 311
```

-continued

Gly Arg Met His His Asp Val Ile Phe Ile Glu Trp Pro Phe Arg
1               5                   10                  15

<210> SEQ ID NO 312
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 312

Asp Val Ile Phe Ile Glu Trp Pro Arg Gly Phe Phe Asp Ile
1               5                   10                  15

<210> SEQ ID NO 313
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 313

Glu Trp Pro Phe Arg Gly Phe Phe Asp Ile His Arg Ser Ala Asn
1               5                   10                  15

<210> SEQ ID NO 314
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 314

Gly Phe Phe Asp Ile His Arg Ser Ala Asn Thr Phe Phe Leu Val
1               5                   10                  15

<210> SEQ ID NO 315
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 315

His Arg Ser Ala Asn Thr Phe Phe Leu Val Val Thr Ala Ala Asn
1               5                   10                  15

<210> SEQ ID NO 316
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 316

Thr Phe Phe Leu Val Val Thr Ala Ala Asn Ile Ser His Asp Gly
1               5                   10                  15

<210> SEQ ID NO 317
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 317

```
Val Thr Ala Ala Asn Ile Ser His Asp Gly Asn Tyr Leu Cys Arg
1               5                   10                  15

<210> SEQ ID NO 318
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 318

Ile Ser His Asp Gly Asn Tyr Leu Cys Arg Met Lys Leu Gly Glu
1               5                   10                  15

<210> SEQ ID NO 319
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 319

Asn Tyr Leu Cys Arg Met Lys Leu Gly Glu Thr Glu Val Thr Lys
1               5                   10                  15

<210> SEQ ID NO 320
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 320

Met Lys Leu Gly Glu Thr Glu Val Thr Lys Gln Glu His Leu Ser
1               5                   10                  15

<210> SEQ ID NO 321
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 321

Thr Glu Val Thr Lys Gln Glu His Leu Ser Val Val Lys Pro Leu
1               5                   10                  15

<210> SEQ ID NO 322
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 322

Gln Glu His Leu Ser Val Val Lys Pro Leu Thr Leu Ser Val His
1               5                   10                  15

<210> SEQ ID NO 323
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 323

Val Val Lys Pro Leu Thr Leu Ser Val His Ser Glu Arg Ser Gln
```

```
<210> SEQ ID NO 324
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 324

Thr Leu Ser Val His Ser Glu Arg Ser Gln Phe Pro Asp Phe Ser
1               5                   10                  15

<210> SEQ ID NO 325
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 325

Ser Glu Arg Ser Gln Phe Pro Asp Phe Ser Val Leu Thr Val Thr
1               5                   10                  15

<210> SEQ ID NO 326
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 326

Phe Pro Asp Phe Ser Val Leu Thr Val Thr Cys Thr Val Asn Ala
1               5                   10                  15

<210> SEQ ID NO 327
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 327

Val Leu Thr Val Thr Cys Thr Val Asn Ala Phe Pro His Pro His
1               5                   10                  15

<210> SEQ ID NO 328
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 328

Cys Thr Val Asn Ala Phe Pro His Pro His Val Gln Trp Leu Met
1               5                   10                  15

<210> SEQ ID NO 329
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 329

Phe Pro His Pro His Val Gln Trp Leu Met Pro Glu Gly Val Glu
1               5                   10                  15
```

<210> SEQ ID NO 330
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 330

Val Gln Trp Leu Met Pro Glu Gly Val Glu Pro Ala Pro Thr Ala
1               5                   10                  15

<210> SEQ ID NO 331
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 331

Pro Glu Gly Val Glu Pro Ala Pro Thr Ala Ala Asn Gly Gly Val
1               5                   10                  15

<210> SEQ ID NO 332
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 332

Pro Ala Pro Thr Ala Ala Asn Gly Gly Val Gly Ser Leu Ser Val
1               5                   10                  15

<210> SEQ ID NO 333
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 333

Ala Asn Gly Gly Val Gly Ser Leu Ser Val Ala Val Asp Leu Ser
1               5                   10                  15

<210> SEQ ID NO 334
<211> LENGTH: 15
<212> TYPE: PRT
<213> ORGANISM: Virus Herpesviridae
<220> FEATURE:
<223> OTHER INFORMATION: EBV - protein BARF 1 fragment

<400> SEQUENCE: 334

Gly Ser Leu Ser Val Ala Val Asp Leu Ser Leu Pro Lys Pro Trp
1               5                   10                  15

<210> SEQ ID NO 335
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 335

Ala Val Asp Leu Ser Leu Pro Lys Pro Trp His Leu Pro Val Thr
1               5                   10                  15

<210> SEQ ID NO 336
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 336

```
Leu Pro Lys Pro Trp His Leu Pro Val Thr Cys Val Gly Lys Asn
1               5                   10                  15
```

<210> SEQ ID NO 337
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 337

```
His Leu Pro Val Thr Cys Val Gly Lys Asn Asp Lys Glu Glu Ala
1               5                   10                  15
```

<210> SEQ ID NO 338
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 338

```
Cys Val Gly Lys Asn Asp Lys Glu Glu Ala His Gly Val Tyr Val
1               5                   10                  15
```

<210> SEQ ID NO 339
<211> LENGTH: 15
<212> TYPE: PRT
<213> ORGANISM: Virus Herpesviridae
<220> FEATURE:
<223> OTHER INFORMATION: EBV-protein BARF 1 fragment

<400> SEQUENCE: 339

```
Asp Lys Glu Glu Ala His Gly Val Tyr Val Ser Gly Tyr Leu Ser
1               5                   10                  15
```

<210> SEQ ID NO 340
<211> LENGTH: 220
<212> TYPE: PRT
<213> ORGANISM: Virus Herpesviridae
<220> FEATURE:
<223> OTHER INFORMATION: EBV-protein BHRF 1

<400> SEQUENCE: 340

```
Met Ala Arg Phe Ile Ala Gln Leu Leu Leu Ala Ser Cys Val Ala
1               5                   10                  15

Ala Gly Gln Ala Val Thr Ala Phe Leu Gly Glu Arg Val Thr Leu Thr
                20                  25                  30

Ser Tyr Trp Arg Arg Val Ser Leu Gly Pro Glu Ile Glu Val Ser Trp
                35                  40                  45

Phe Lys Leu Gly Pro Gly Glu Glu Gln Val Leu Ile Gly Arg Met His
        50                  55                  60

His Asp Val Ile Phe Ile Glu Trp Pro Phe Arg Gly Phe Phe Asp Ile
65                  70                  75                  80

His Arg Ser Ala Asn Thr Phe Phe Leu Val Val Thr Ala Ala Asn Ile
                85                  90                  95
```

```
Ser His Asp Gly Asn Tyr Leu Cys Arg Met Lys Leu Gly Glu Thr Glu
            100                 105                 110
Val Thr Lys Gln Glu His Leu Ser Val Val Lys Pro Leu Thr Leu Ser
        115                 120                 125
Val His Ser Glu Arg Ser Gln Phe Pro Asp Phe Ser Val Leu Thr Val
    130                 135                 140
Thr Cys Thr Val Asn Ala Phe Pro His Pro His Val Gln Trp Leu Met
145                 150                 155                 160
Pro Glu Gly Val Glu Pro Ala Pro Thr Ala Ala Asn Gly Gly Val Met
                165                 170                 175
Lys Glu Lys Asp Gly Ser Leu Ser Val Ala Val Asp Leu Ser Leu Pro
            180                 185                 190
Lys Pro Trp His Leu Pro Val Thr Cys Val Gly Lys Asn Asp Lys Glu
        195                 200                 205
Glu Ala His Gly Val Tyr Val Ser Gly Tyr Leu Ser
    210                 215                 220
```